United States Patent
Nieman et al.

(10) Patent No.: US 9,486,481 B2
(45) Date of Patent: Nov. 8, 2016

(54) METHOD OF MODULATING FATTY ACID MOBILIZATION AND OXIDATION

(71) Applicant: Reoxcyn Discoveries Group, Inc., Salt Lake City, UT (US)

(72) Inventors: David Nieman, Weaverville, NC (US); Bristol Sorensen, San Leandro, CA (US)

(73) Assignee: Reoxcyn Discoveries Group, Inc., Salt Lake City, UT (US)

(*) Notice: Subject to any disclaimer, the term of this patent is extended or adjusted under 35 U.S.C. 154(b) by 125 days.

(21) Appl. No.: 14/021,329

(22) Filed: Sep. 9, 2013

(65) Prior Publication Data

US 2014/0056991 A1    Feb. 27, 2014

Related U.S. Application Data

(63) Continuation-in-part of application No. 13/857,225, filed on Apr. 5, 2013, which is a continuation-in-part of application No. 12/592,402, filed on Nov. 24, 2009, now Pat. No. 8,455,010, which is a continuation-in-part of application No. 12/383,212, filed on Mar. 20, 2009, now Pat. No. 8,367,120, which is a continuation-in-part of application No. 12/290,398, filed on Oct. 30, 2008, now abandoned, application No. 14/021,329, which is a continuation-in-part of application No. 13/857,882, filed on Apr. 5, 2013, which is a continuation-in-part of application No. 12/592,402, filed on Nov. 24, 2009, now Pat. No. 8,455,010, which is a continuation-in-part of application No. 12/383,212, filed on Mar. 20, 2009, now Pat. No. 8,367,120, which is a continuation-in-part of application No. 12/290,398, filed on Oct. 30, 2008, now abandoned.

(60) Provisional application No. 61/001,010, filed on Oct. 30, 2007.

(51) Int. Cl.
```
A61K 33/40     (2006.01)
A61K 33/00     (2006.01)
A61K 33/14     (2006.01)
G01N 33/92     (2006.01)
A61K 33/20     (2006.01)
A61K 45/06     (2006.01)
```

(52) U.S. Cl.
CPC ............ *A61K 33/40* (2013.01); *A61K 33/00* (2013.01); *A61K 33/14* (2013.01); *A61K 33/20* (2013.01); *A61K 45/06* (2013.01); *G01N 33/92* (2013.01)

(58) Field of Classification Search
None
See application file for complete search history.

(56) References Cited

U.S. PATENT DOCUMENTS

| | | |
|---|---|---|
| 4,236,992 A | 12/1980 | Themy |
| 4,316,787 A | 2/1982 | Themy |
| 4,810,344 A | 3/1989 | Okazaki |
| 5,334,383 A | 8/1994 | Morrow |
| 5,507,932 A | 4/1996 | Robinson |
| 5,674,537 A | 10/1997 | Morrow |
| 6,007,686 A | 12/1999 | Welch |
| 6,117,285 A | 9/2000 | Welch |
| 6,821,403 B1 * | 11/2004 | Lundquist ................. 204/554 |
| 7,691,249 B2 | 4/2010 | Daly |
| 8,062,501 B2 | 11/2011 | Omasa |
| 8,323,252 B2 | 12/2012 | Alimi |
| 8,367,120 B1 | 2/2013 | Norton |
| 8,455,010 B1 | 6/2013 | Norton |
| 8,663,705 B2 | 3/2014 | Norton |
| 9,255,336 B2 | 2/2016 | Norton |
| 2007/0215489 A1 * | 9/2007 | Omasa ................ C02F 1/34  205/742 |
| 2007/0261950 A1 * | 11/2007 | Sato et al. ............ 204/157.52 |
| 2011/0121110 A1 | 5/2011 | Field |
| 2013/0115307 A1 | 5/2013 | Norton |
| 2013/0236563 A1 | 9/2013 | Samuelson |
| 2013/0243883 A1 | 9/2013 | Norton |
| 2014/0044800 A1 | 2/2014 | Robinson |
| 2014/0050800 A1 | 2/2014 | Nieman |
| 2015/0093451 A1 | 4/2015 | Neiman |
| 2015/0246071 A1 | 9/2015 | Robinson |
| 2015/0246832 A1 | 9/2015 | Robinson |

FOREIGN PATENT DOCUMENTS

EP    0933332 A1 *   1/1999   ............... C02F 1/30

OTHER PUBLICATIONS

Baltch, AJIC Am J Infect Control 2000; 28:251-7.
Sawada, Solid polymer electrolyte water electrolysis systems for hydrogen production based on our newly developed membranes, Part I: Analysis of voltage. Progress in Nuclear Energy, vol. 50, Issues 2-6, Mar.-Aug. 2008, pp. 443-448.
Okada, Theory for water management in membranes for polymer electrolyte fuel cells: Part 1. The effect of impurity ions at the anode side on the membrane performances. Journal of Electroanalytical Chemistry vol. 465, Issue 1, Apr. 6, 1999, pp. 1-17.
Okada, Theory for water management in membranes for polymer electrolyte fuel cells: Part 2. The effect of impurity ions at the cathode side on the membrane performances. Journal of Electroanalytical Chemistry, vol. 465, Issue 1, Apr. 5, 1999, pp. 18-29.

(Continued)

*Primary Examiner* — Abigail Fisher
*Assistant Examiner* — Jessica Kassa
(74) *Attorney, Agent, or Firm* — David R. Conklin; Kirton McConkie

(57) ABSTRACT

Methods of mobilizing fatty acids are disclosed.

3 Claims, 41 Drawing Sheets

(56) References Cited

OTHER PUBLICATIONS

Asawa, Material properties of cation exchange membranes for chloralkali electrolysis, water electrolysis and fuel cells. Journal of Applied Electrochemistry. Jul. 1989, vol. 19, Issue 4, pp. 566-570.
Olsen, Clonality and virulence traits of Escherichia coli associated with haemorrhagic septicaemia in turkeys. Avian Pathology (Dec. 2011) 40(6), 587-595.
Mueller-Dolies, A comparison of the efficacy of different disinfection methods in eliminating Salmonella contamination from turkey houses. Journal of Applied Microbiology 109 (2010) 471-479.
McLaren, Evaluation of commonly-used farm disinfectants in wet and dry models of Salmonella farm contamination. Avian Pathology (Feb. 2011) 40(1), 33-42.
Hayyan, Generation and stability of superoxide ion in tris(pentafluoroethyl) trifluorophosphate anion-based ionic liquids. Journal of Fluorine Chemistry. vol. 142, Oct. 2012, pp. 83-89.
Hayyan, Long term stability of superoxide ion in piperidinium, pyrrolidinium and phosphonium cations-based ionic liquids and its utilization in the destruction of chlorobenzenes. Journal of Electroanalytical Chemistry. vol. 664, Jan. 1, 2012, pp. 26-32.
Kahn, Spin Traps: In Vitro Toxicity and Stability of Radical Adducts. Free Radical Biology & Medicine, vol. 34, No. 11, pp. 1473-1481, 2003.
Alnashef, Electrochemical Generation of Superoxide in Room-Temperature Ionic Liquids. Electrochemical and Solid State Letters, 4 (11) D16-DI8 (2001).
Alnashef, Superoxide Electrochemistry in an Ionic Liquid. Ind. Eng. Chem. Res. 2002, 41, 4475-4478.
Sielski, Reactivity of HO2/O2-Radicals in Aqueous Solution. J. Phys. Chem. Ref. Data, vol. 14, No. 4, 1985.
Konaka, Irradiation of Titanium Dioxide Generates Both Singlet Oxygen and Superoxide Anion. Free Radical Biology & Medicine, vol. 27, Nos. 3/4, pp. 294-300, 1999.
Zhuang, Homogeneous blend membrane made from poly( ether sulphone) and poly(vinylpyrrolidone) and its application to water electrolysis. Journal of Membrane Science. vol. 300, Issues 1-2, Aug. 15, 2007, pp. 205-210.
Okada, Ion and water transport characteristics of Nafion membranes as electrolytes. Electrochimica Acta, vol. 43, Issue 24, Aug. 21, 1998, pp. 3741-3747.
Zoulias, Emmanuel, A review on water electrolysis. TCJST 4.2 (2004): 41-71.
Xu, Ion exchange membranes: state of their development and perspective. Journal of Membrane Science 263 (2005) 1-29.
Kariduraganavar, Ion-exchange membranes: preparative methods for electrodialysis and fuel cell applications. Desalination 197 (2006) 225-246.

\* cited by examiner

| Anode | | | | Cathode | | | |
|---|---|---|---|---|---|---|---|
| + | | e−↑ | | e−↓ | | | − |
| | | | | | | | 1st Generation |
| -1.23 V : $O_2$ : $4H^+$ | 4e ↑ | $2H_2O$ | | $2H^+$ | 2e ↓ | $H_2$ | : -0.00V |
| -0.40V : $O_2$ | 4e ↑ | $4OH^-$ | | $2H_2O$ | 2e ↓ | $H_2$ $2OH^-$ | : -0.83V |
| -.89V : $ClO^-$ : $H_2O$ | 2e ↑ | $2OH^-$ $Cl^-$ | | $2H_2O$ | 2e ↓ | $2H^+$ $H_2O_2$ | : 1.76V |
| -1.36 V : $Cl_2$ | 2e ↑ | $2Cl^-$ | | $Na^+$ | 1e ↓ | $Na_{(s)}$ | : -2.71V |
| | | | | | | | 2nd Generation |
| -1.63V : $2HClO$ : $2H^+$ | 2e ↑ | $Cl_2$ $2H_2O$ | | $O_2$ | 1e ↓ | $O_2^{*-}$ | : -0.33V |
| -1.67V : $HClO_2$ : $2H^+$ | 2e ↑ | $HClO$ $H_2O$ | | $O_2$ $H^+$ | 1e ↓ | $HO_2^*$ | : -0.13V |
| -2.07V : $O_3$ : $2H^+$ | 2e ↑ | $O_2$ $H_2O$ | | $O_2$ $H^+$ | 2e ↓ | $H_2O_2$ | : 0.70V |
| -1.18V : $2ClO_3^-$ : $12H^+$ | 10e ↑ | $ICl_2$ $6H_2O$ | | $2HClO$ $2H^+$ | 2e ↓ | $Cl_2$ $2H_2O$ | : 1.63V |
| | | | | | | | 3rd Generation+ |
| -1.19V : $ClO_2$ : $H^+$ | 1e ↑ | $HClO_2$ $H_2O$ | | $HO_2^*$ | 1e ↓ | $H_2O_2$ | : 1.51V |
| -1.18V : $ClO_3^-$ : $2H^+$ | 1e ↑ | $ClO_2$ $H_2O$ | | $H_2$ | 2e ↓ | $2H^-$ | : -2.25V |

FIG. 2

FIG. 11
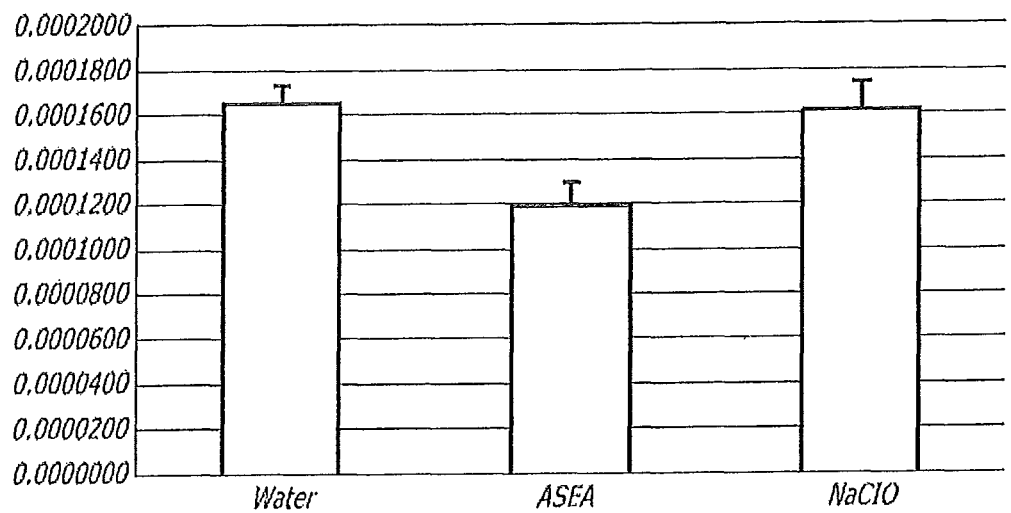
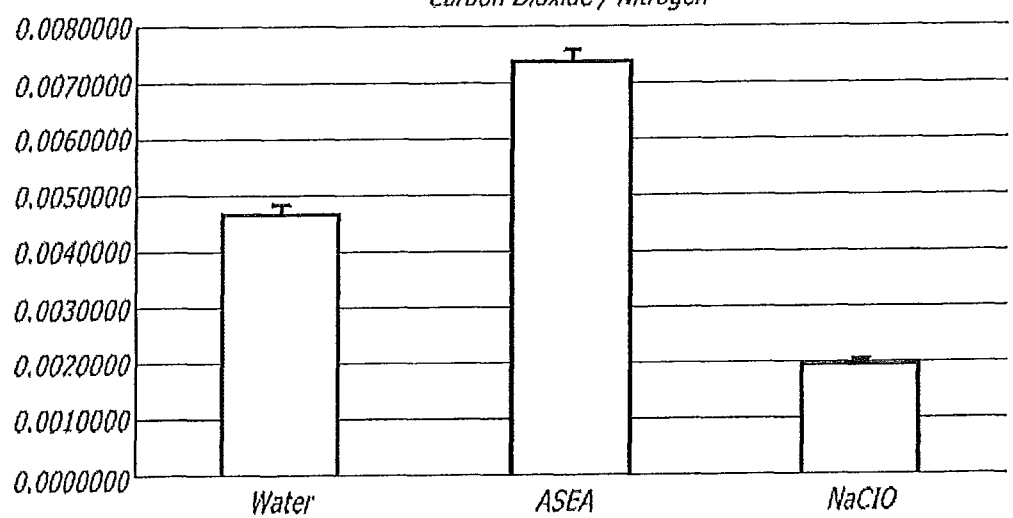
FIG. 12

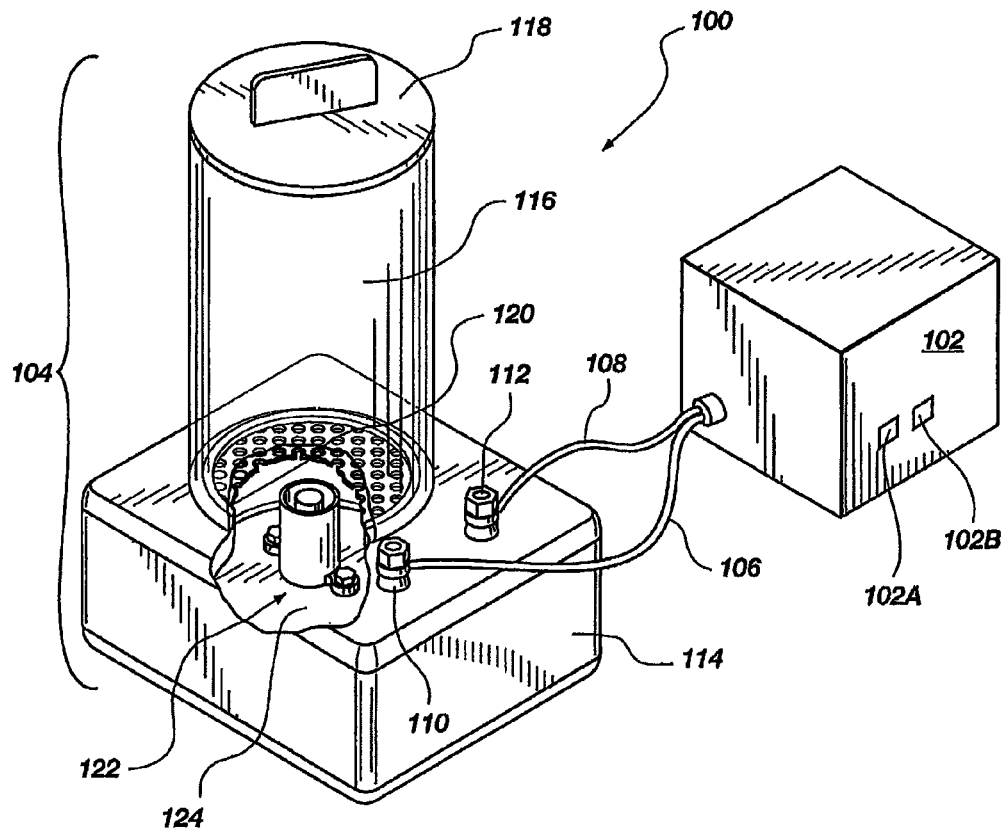
FIG 14
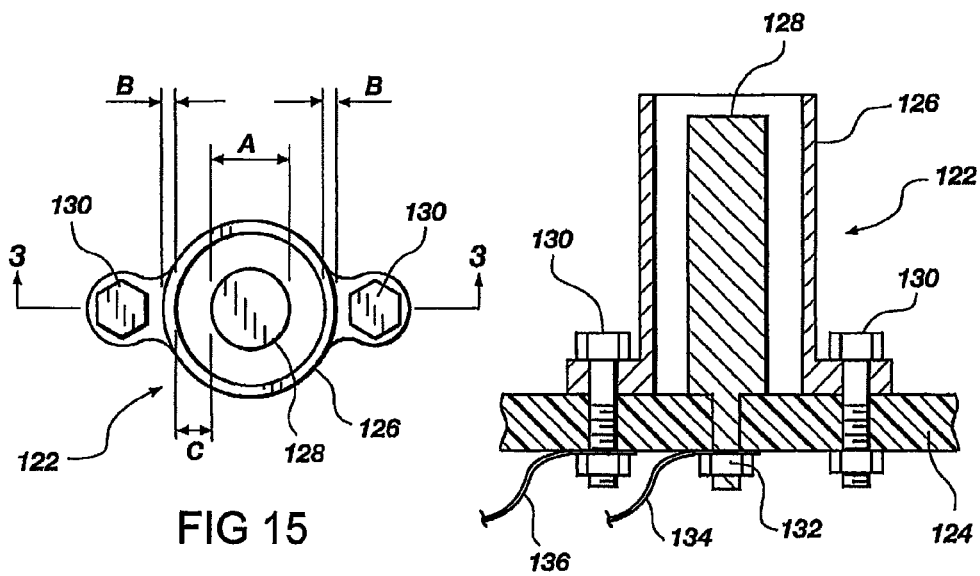
FIG 15
FIG 15a

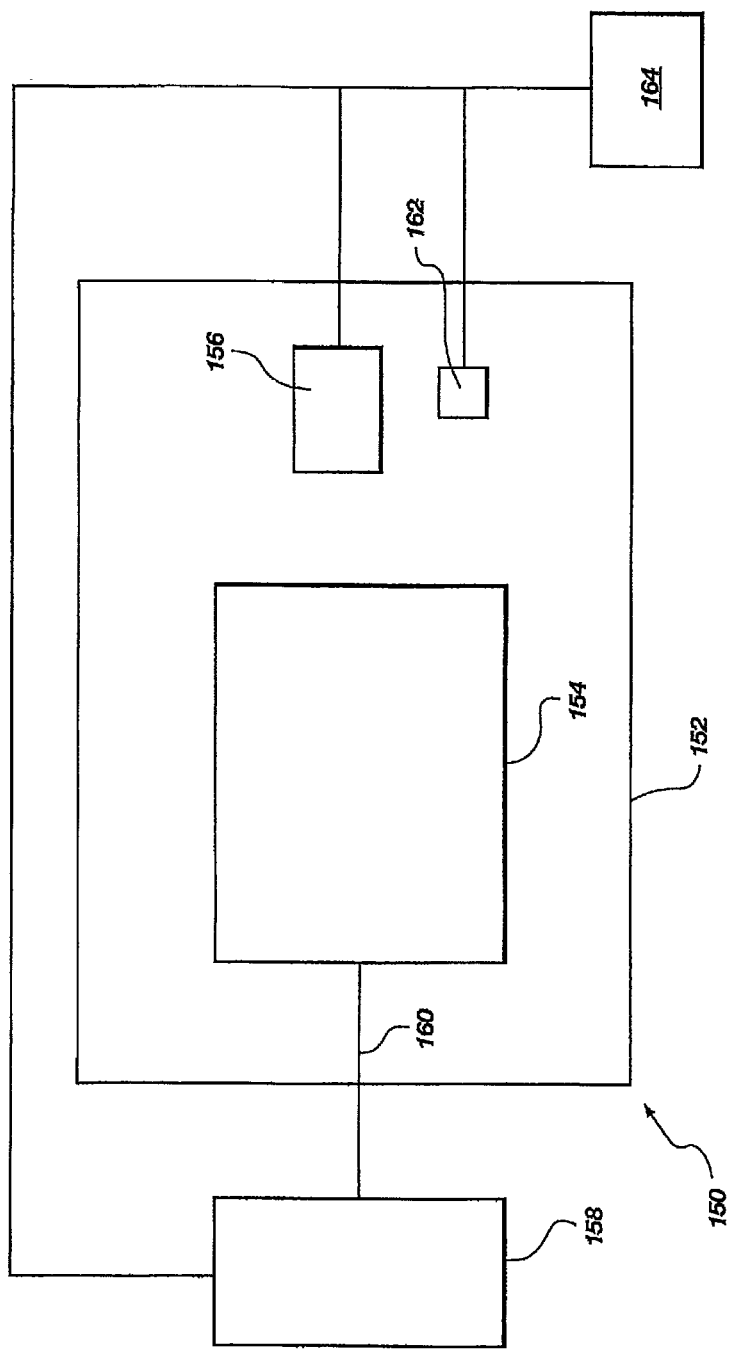

Fig. 29
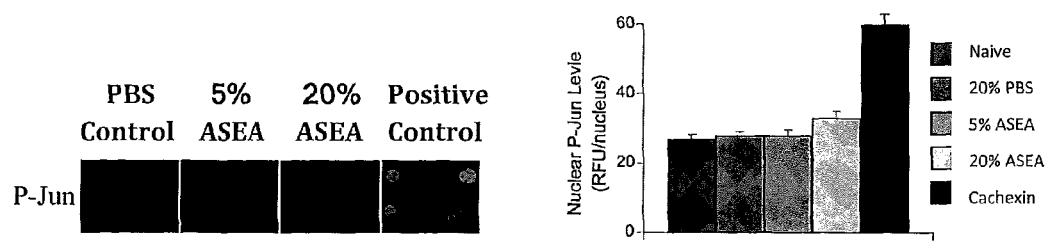
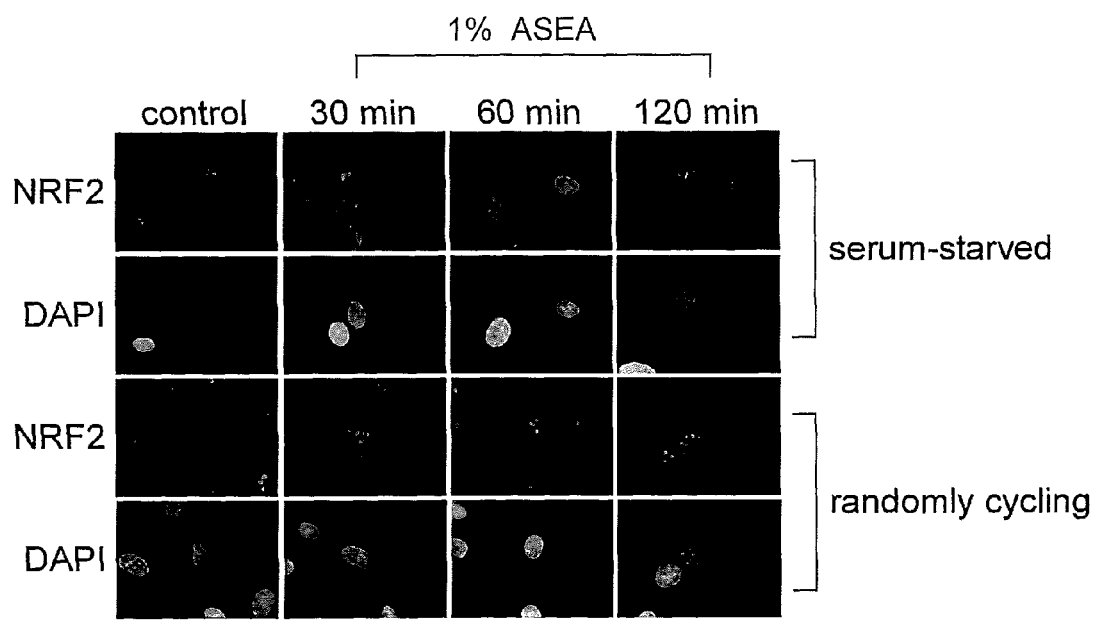
FIG. 30

Fig. 35
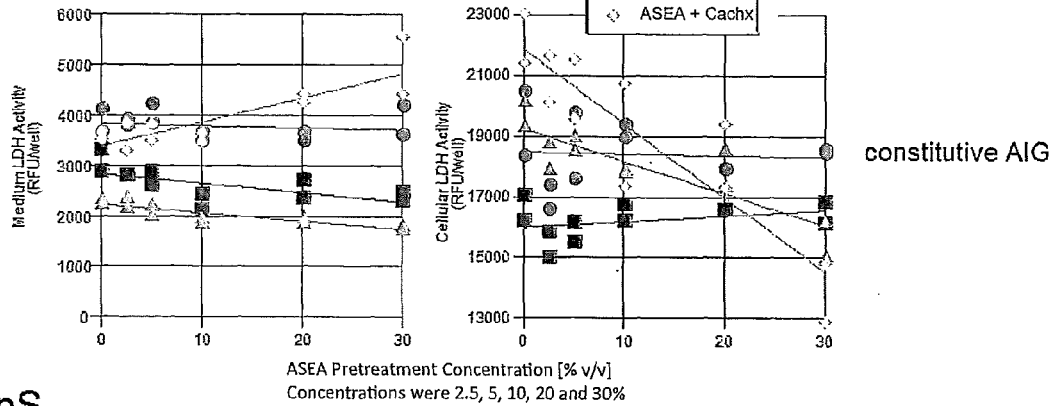
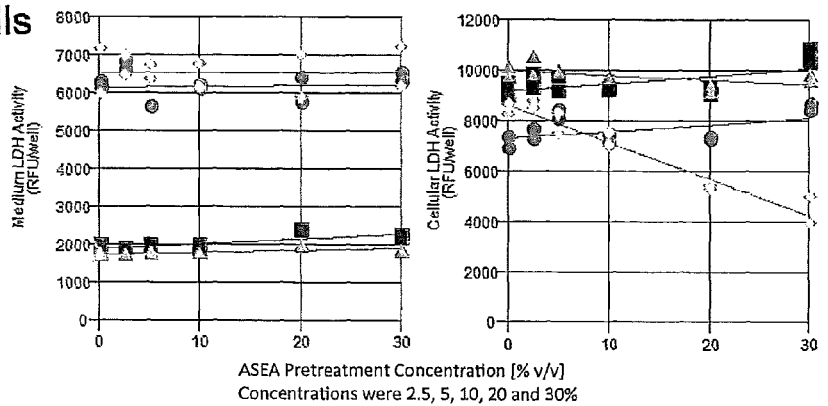
Fig. 36
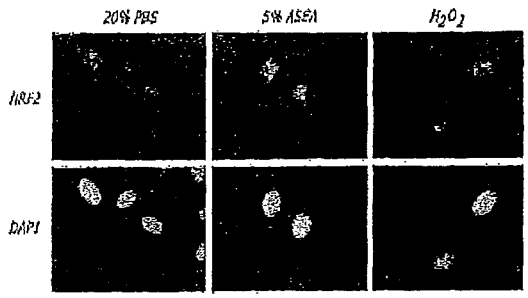

Running Endurance Time to Exhaustion
One Week Placebo or ASEA Ingestion

Note: The decrease was primarily from LDL-cholesterol (bad cholesterol) (P=0.059)

METHOD OF MODULATING FATTY ACID MOBILIZATION AND OXIDATION

CROSS-REFERENCE TO RELATED APPLICATIONS

This application is a Continuation-in-part of, and claims the benefit of, U.S. patent application Ser. No. 13/857,225, filed on Apr. 5, 2013 which is a Continuation-In-Part of U.S. patent application Ser. No. 12/592,402, filed Nov. 24, 2009 now U.S. Pat. No. 8,455,010 B1 which is a Continuation-in-part of U.S. patent application Ser. No. 12/383,212, filed Mar. 20, 2009, now U.S. Pat. No. 8,367,120 B1, which is a Continuation-in-Part of U.S. patent application Ser. No. 12/290,398, filed Oct. 30, 2008, now abandoned, which claims priority to U.S. Provisional Patent Application Ser. No. 61/001,010, filed Oct. 30, 2007, the entire contents all of which are herein incorporated by reference in their entirety.

This application is a Continuation-in-part of, and claims the benefit of, U.S. patent application Ser. No. 13/857,882, filed on Apr. 5, 2013 which is a Continuation-In-Part of U.S. patent application Ser. No. 12/592,402, filed Nov. 24, 2009 now U.S. Pat. No. 8,455,010 B1 which is a Continuation-in-part of U.S. patent application Ser. No. 12/383,212, filed Mar. 20, 2009, now U.S. Pat. No. 8,367,120 B1, which is a Continuation-in-Part of U.S. patent application Ser. No. 12/290,398, filed Oct. 30, 2008, now abandoned, which claims priority to U.S. Provisional Patent Application Ser. No. 61/001,010, filed Oct. 30, 2007, the entire contents all of which are herein incorporated by reference in their entirety.

NAMES OF THE PARTIES TO A JOINT RESEARCH AGREEMENT

The presently claimed invention was made by or on behalf of the below listed parties to a joint research agreement. The joint research agreement was in effect on or before the date the claimed invention was made and the claimed invention was made as a result of activities undertaken within the scope of the joint research agreement. The parties to the joint research agreement are REOXCYN DISCOVERIES GROUP, INC. and Appalachian State University.

BACKGROUND OF THE INVENTION

1. Field of the Invention

The present invention relates generally to methods of increasing resting metabolic rate.

2. Background

Fatty acids are released from adipose cells during times of stress when the body needs energy. For example, during exercise, triglycerides are hydrolyzed into fatty acids as a fuel source (Horowitz J F. Fatty acid mobilization from adipose tissue during exercise. Trends Endocrinol Metab. 2003 October; 14(8):386-92, which is incorporated herein in its entirety). Understanding fatty acid mobilization will provide not only a better understanding of the energy sourcing pathways, but also provide insight into metabolic disorders such as obesity and atherosclerosis (Hodenberg et al. Mobilization of stored triglycerides from macrophages as free fatty acids. Arterioscler Thromb Vasc Biol. 1984; 4:630-635, which is incorporated herein in its entirety).

Some subjects do not have proper mobilization of fatty acids due to health conditions or other reasons. Therefore, there is a need for a composition which can, when administered to a subject, mobilize fatty acids in that subject.

3. Description of Related Art

It has long been known that the electrolysis of fluids can result in useful products. Thus, various apparatus and methods have been proposed for electrolyzing saline solution, however, all of the previously available schemes present one or more drawbacks.

For example U.S. Pat. No. 7,691,249 teaches a method an apparatus for making electrolyzed water comprising an insulating end cap for a cylindrical electrolysis cell and is incorporated herein by reference in its entirety.

For example, U.S. Pat. Nos. 4,236,992 and 4,316,787 to Themy disclose an electrode, method and apparatus for electrolyzing dilute saline solutions to produce effective amounts of disinfecting agents such as chlorine, ozone and hydroxide ions. Both of these references are incorporated herein by reference in their entireties U.S. Pat. No. 5,674,537, U.S. Pat. No. 6,117,285 and U.S. Pat. No. 6,007,686 also teach electrolyzed fluids and are now incorporated herein by reference in their entireties.

U.S. Pat. No. 4,810,344 teaches a water electrolyzing apparatus including a plurality of electrolysis devices, each comprising an electrolysis vessel having a cathode and an anode oppose to each other and an electrolysis diaphragm partitioning the space between both of the electrodes wherein the plurality of devices are connected in a series such that only one of the two ionized water discharge channels of the devices constitutes a water supply channel to the device a the succeeding stage and is incorporated herein by reference in its entirety.

U.S. Pat. No. 7,691,249 is now incorporated herein by reference in its entirety and is directed to a method and apparatus for making electrolyzed water.

Methods for treatment of physiological fluids using electrolyzed solutions are set forth in U.S. Pat. No. 5,334,383 which is now incorporated herein by reference in its entirety teaches an electrolyzed saline solution, properly made and administered in vivo, as effective in the treatment of various infections brought on by invading antigens and particularly viral infections.

U.S. Pat. No. 5,507,932 which is now incorporated herein by reference in its entirety teaches an apparatus for electrolyzing fluids.

Described herein generally are aqueous formulations including at least one stable reactive and/or radical species.

U.S. Pat. No. 8,062,501 B2 is directed to a method for producing neutral electrolytic water containing OH, D2, HD and HDO as active elements and is incorporated herein by reference in its entirety.

There is a need for stabilized or contained superoxides, hydroxyl radicals and/or OOH* in an aqueous medium, without solvents or catalysts, outside the human body. The art teaches that superoxides, hydroxyl radicals and/or OOH* last for a very short amount of time. Even years after the priority date of this application, stabilizing superoxides in particular was proving difficult and inapplicable: Hayyan et al. Generation and stability of superoxide ion in tris(pentafluoroethyl)trifluorophosphate anion-based ionic liquids. Journal of Fluorine Chemistry. Volume 142, October 2012, Pages 83-89 and Hayyan et al. Long term stability of superoxide ion in piperidinium, pyrrolidinium and phosphonium cations-based ionic liquids and its utilization in the destruction of chlorobenzenes. Journal of Electroanalytical Chemistry. Volume 664, 1 Jan. 2012, Pages 26-32.

At the time the priority document was filed, superoxides were known to have a very short lifespan: Kahn et al. SPIN TRAPS: IN VITRO TOXICITY AND STABILITY OF RADICAL ADDUCTS. Free Radical Biology & Medicine, Vol. 34, No. 11, pp. 1473-1481, 2003, AlNashef et al. Electrochemical Generation of Superoxide iN Room-Temperature Ionic Liquids. Electrochemical and Solid State Letters, 4 (11) D16-D18 (2001), AlNashef et al. Superoxide Electrochemistry in an Ionic Liquid. Ind. Eng. Chem. Res. 2002, 41, 4475-4478, Bielski et al. Reactivity of HO2/O2-Radicals in Aqueous Solution. J. Phys. Chem. Ref. Data, Vol. 14, No. 4 1985, Konaka et al. IRRADIATION OF TITANIUM DIOXIDE GENERATES BOTH SINGLET OXYGEN AND SUPEROXIDE ANION. Free Radical Biology & Medicine, Vol. 27, Nos. 3/4, pp. 294-300, 1999.

Typically, in the process of making electrolyzed water, membranes are considered required. Zhuang et al. Homogeneous blend membrane made from poly(ether sulphone) and poly(vinylpyrrolidone) and its application to water electrolysis. Journal of Membrane Science. Volume 300, Issues 1-2, 15 Aug. 2007, Pages 205-210, Sawada et al. Solid polymer electrolyte water electrolysis systems for hydrogen production based on our newly developed membranes, Part I: Analysis of voltage. Progress in Nuclear Energy, Volume 50, Issues 2-6, March-August 2008, Pages 443-448, Okada et al. Theory for water management in membranes for polymer electrolyte fuel cells: Part 1. The effect of impurity ions at the anode side on the membrane performances. Journal of Electroanalytical Chemistry Volume 465, Issue 1, 6 Apr. 1999, Pages 1-17, Okada et al. Theory for water management in membranes for polymer electrolyte fuel cells: Part 2. The effect of impurity ions at the cathode side on the membrane performances. Journal of Electroanalytical Chemistry, Volume 465, Issue 1, 6 Apr. 1999, Pages 18-29, Okada et al. Ion and water transport characteristics of Nafion membranes as electrolytes. Electrochimica Acta, Volume 43, Issue 24, 21 Aug. 1998, Pages 3741-3747, Zoulias et al. A Review on Water Electrolysis last modified 20 Jan. 2006 15:24, http://www.cres.gr/kape/publications/papers/dimosieyseis/ydrogen/A%20REVIEW%20ON%20WATER%20ELECTROLYSIS.pdf, Xu et al. Ion exchange membranes: state of their development and perspective. Journal of Membrane Science 263 (2005) 1-29, Kariduraganavar et al. Ion-exchange membranes: preparative methods for electrodialysis and fuel cell applications. Desalination 197 (2006) 225-246, Asawa et al. Material properties of cation exchange membranes for chlorakali electrolysis, water electrolysis and fuel cells. Journal of Applied Electrochemistry. July 1989, Volume 19, Issue 4, pp 566-570. However, the inventive product and process described herein is done without a separator or separating membrane/diaphragm.

Reactive oxygen species (ROS) are of immense interest in medicine because there is compelling evidence linking them to aging, disease processes and the reduction of oxidative stress. Further, they are employed as microbicidal agents in the home, hospital and other settings. ROS include superoxides. There is a need in the art for a safe, effective, economical way of producing superoxides and employing them in the medical industry. Described herein is a product and a process for making electrolyzed water which contain these and other radicals and methods of using these superoxides and other radicals to mobilize fatty acids.

BRIEF SUMMARY OF THE INVENTION

The invention comprises a method of mobilizing fatty acids in a subject comprising administering to the subject a balanced composition of stabilized redox-signaling molecules that is particularly safe and suited for oral consumption. This composition is similar to that of a target composition of redox-signaling molecules that exists naturally inside a healthy human cell. Such a healthy balance includes a balance of oxidants and antioxidants. The composition acts to enhance proper immune system function, to enhance the efficiency and production of the body's native antioxidants as well as to enhance the performance of intercellular communications involved in the maintenance of healthy tissues.

Redox signaling deals with the action of a set of several simple reactive signaling molecules that are mostly produced by the mitochondria residing inside human cells during the metabolism of sugars. These reactive signaling molecules are categorized into two general groups, Reactive Oxygen Species (ROS), which contain oxidants, and Reduced Species (RS), which contain reductants. These fundamental universal signaling molecules in the body are the simple but extremely important reactive signaling molecules that are formed from combinations of the atoms (Na, Cl, H, O, N) that are readily found in the saline bath that fills the inside of the cells (cytosol). All of the molecular mechanisms inside healthy cells float around in this saline bath and are surrounded by a balanced mixture of such reactive signaling molecules. A few examples of the more than 20 reactive molecules formed from these atoms inside the cell, some of which are discussed herein, are superoxide, hydrogen peroxide, hypochlorous acid and nitric oxide.

Such reactive signaling molecules are chemically broken down by specialized enzymes placed at strategic locations inside the cell. Some of these protective enzymes are classified as antioxidants such as Glutathione Peroxidase and Superoxide Dismutase. In a healthy cell, the mixtures of these reactive signaling molecules are broken down by the antioxidant enzymes at the same rate that they are produced by the mitochondria. As long as this homeostatic balance is maintained, the cell's chemistry is in balance and all is well.

When damage occurs to the cell, for any number of reasons, including bacterial or viral invasion, DNA damage, physical damage or toxins, this homeostatic balance is disturbed and a build-up of oxidants or reductants occurs in the cell. This condition is known as oxidative stress and it acts as a clear signal to the cell that something is wrong. The cell reacts to this signal by producing the enzymes and repair molecules necessary to attempt repairs to the damage and it also can send messengers to activate the immune system to identify and eliminate threats. If oxidative stress persists in the cell for more than a few hours, then the cell's repair attempts are considered unsuccessful and the cell kills and dismantles itself and is replaced by the natural cellular division of healthy neighboring cells.

On a cellular level, this is essentially the healthy tissue maintenance process: damaged cells are detected and repaired or replaced by healthy cells. This cellular repair and regeneration process is constantly taking place, millions of times an hour, in all parts of the body.

In one embodiment, the invention is directed to a method of mobilizing fatty acids in a subject comprising administering to the subject a composition comprising a mixture of reduced species (RS) and reactive oxygen species (ROS) wherein the mixture of reduced species (RS) and reactive oxygen species (ROS) mobilizes the fatty acids in the subject.

In one embodiment, the invention is directed to a method of mobilizing fatty acids in a subject wherein the reactive oxygen species (ROS) comprises at least one superoxide.

In one embodiment, the invention is directed to a method of mobilizing fatty acids in a subject wherein the administration occurs orally and wherein the administration is substantially concurrent with exercise.

In another embodiment, the invention is directed to a method of mobilizing fatty acids in a subject wherein the fatty acids mobilized are selected from the group consisting of 1-palmitoylglycerophosphoethanolamine, 1-oleoylglycerophosphoethanolamine, 1-stearoylglycerophosphoethanolamine, 1-arachidonoylglycerophosphoethanolamine, 1-palmitoylglycerophosphoinositol, 1,3-dipalmitoylglycerol, 1-oleoylglycerophosphoinositol, 2-linoleoylglycerophosphoethanolamine, 1-palmitoylglycerol (1-monopalmitin), 1-stearoylglycerol (1-monostearin), glycerol and combinations thereof.

In a further embodiment, the invention is directed to a method of mobilizing fatty acids in a subject wherein the composition comprises:

a. sodium present at a concentration of 1000 to 1400 ppm wherein the sodium is measured by inductively coupled plasma mass spectrometry (ICP-MS), b. chloride present at a concentration from 1200 to 1600 ppm as wherein the chloride is measured by inductively coupled plasma mass spectrometry (ICP-MS) or chloride is present at a concentration from 0 to 1 ppm wherein the chloride is measured by 35Cl nuclear magnetic resonance (35Cl NMR), c. hypochlorous acid present at a concentration of 16 to 24 ppm wherein the hypochlorous acid is measured by colorimetry or hypochlorous acid present at a concentration of 2300 to 2700 ppm wherein the hypochlorous acid is measured by 25Cl nuclear magnetic resonance (25Cl NMR), d. superoxide radical present at a concentration of 94 uM wherein the superoxide radical is measured by 5-(Diisopropoxyphosphoryl)-5-1-pyrroline-N-oxide nuclear magnetic resonance (DIPPMPO-NMR), and e. hydroxyl radical present at a concentration of 241 uM wherein the hydroxyl radical is measured by DIPPMPO-NMR or hydroxyl radical present at a concentration of 0 to 10 ppm wherein the hydroxyl radical is measured by mass spectrometry (MS).

In one aspect, the invention is directed to a method of mobilizing fatty acids in a subject wherein the composition has a pH between 6 and 9.

In another aspect, the invention is directed to a method of mobilizing fatty acids in a subject wherein the sodium, chloride, hypochlorous acid, superoxide radical and hydroxyl radical are measured less than one year after the composition was made.

In a further aspect, the invention is directed to a method of mobilizing fatty acids in a subject wherein the sodium, chloride, hypochlorous acid, superoxide radical and hydroxyl radical are present in the composition for at least 3 months.

In one embodiment, the invention is directed to a method of mobilizing fatty acids in a subject wherein the sodium, chloride, hypochlorous acid, superoxide radical and hydroxyl radical are present in the composition for at least 6 months.

In another embodiment, the invention is directed to a method of mobilizing fatty acids in a subject, wherein the sodium, chloride, hypochlorous acid, superoxide radical and hydroxyl radical are present in the composition for at least a year.

In a further embodiment, the invention is directed to a method of mobilizing fatty acids in a subject wherein the sodium, chloride, hypochlorous acid, superoxide radical and hydroxyl radical are present at any time within 1 year after the composition was made.

In still another aspect, the invention is directed to a method of mobilizing fatty acids in a subject wherein the sodium, chloride, hypochlorous acid, superoxide and hydroxyl radical are measured at different times.

In one embodiment, the invention is directed to a method of mobilizing fatty acids in a subject wherein the sodium, chloride, hypochlorous acid, superoxide radical and hydroxyl radical are measured at the same time.

In one embodiment, the invention is directed to a method of mobilizing fatty acids in a subject wherein the process of making the composition comprises the steps of purifying water to produce ultra-pure water, combining sodium chloride to the ultra-pure water to create a salinated water, electrolyzing the salinated water at a temperature of 4.5 to 5.8° C. wherein the electrolyzing is accomplished with an anode, cathode and power source such that the power source comprises a transformer and a rectifier and does not comprise a filter capacitor.

In one embodiment, the invention is directed to a method of mobilizing fatty acids in a subject wherein the process includes a pulsating voltage such that the voltage is 0 at least 50 times per second.

In a further embodiment, the invention is directed to a method of mobilizing fatty acids in a subject wherein the composition has an electron paramagnetic resonance (EPR) spectrum as shown in FIG. 13.

BRIEF DESCRIPTION OF THE DRAWINGS

FIG. 2 illustrates an example diagram of the generation of various molecules at the electrodes. The molecules written between the electrodes depict the initial reactants and those on the outside of the electrodes depict the molecules/ions produced at the electrodes and their electrode potentials.

FIG. 11 illustrates ozone/nitrogen ratios for a composition described herein compared to water and NaClO (the composition is labeled "ASEA").

FIG. 12 illustrates the carbon dioxide to nitrogen ratio of a composition as described herein compared to water and NaClO (the composition is labeled "ASEA").

FIG. 14 is a perspective view of a first presently preferred embodiment of an apparatus for making the present invention.

FIG. 15 is a detailed top view of the electrode assembly represented in FIG. 14.

FIG. 15A is a side cross sectional view of the electrode assembly represented in FIG. 15 taken along line 3-3 in FIG. 15.

FIG. 16 is a block diagram of a second presently preferred embodiment of an apparatus for making the present invention.

FIG. 29 illustrates results for P-Jun screen for toxicity (the composition embodiment used in the protocol is referred-to as "ASEA").

FIG. 30 illustrates serum-starved cell cultures exposed to low-concentration ASEA (a composition disclosed herein).

FIG. 35 illustrates results of concentration-dependent response of HMVEC-L cells to Cachexin insult (the composition embodiment used in the protocol is referred-to as "ASEA").

FIG. 36 illustrates results of HMVEC-L Nuclear Accumulation of NRF2.

DETAILED DESCRIPTION OF THE INVENTION

Described herein are compositions including fluids that generally include at least one redox signaling agent (RXN) and methods of using such compositions. RXNs can include, but are not limited to superoxides: $O_2^*-$, $HO_2^*$; hypochlorites: $OCl-$, $HOCl$, $NaOCl$; hypochlorates: $HClO_2$, $ClO_2$, $HClO_3$, $HClO_4$; oxygen derivatives: $O_2$, $O_3$, $O_4^*-$, $1O$; hydrogen derivatives: $H_2$, $H-$; hydrogen peroxide: $H_2O_2$; hydroxyl free Radical: $OH^*-$; ionic compounds: $Na+$, $Cl-$, $H+$, $OH-$, $NaCl$, $HCl$, $NaOH$; chlorine: $Cl_2$; water clusters: $n^*H_2O$-induced dipolar layers around ions and combinations thereof. Some RXNs are electron acceptors (RS) and include $HOCl$, $NaClO$, $O_2$, $H_2$, $H+$, $ClO$, $Cl_2$, $H_2O_2$ and some are electron donors (ROS) and include $O_2-$, $HO_2$, $Cl-$, $H-$, $*OCl$, $O_3$, $*O_2-$ and $OH-$.

Methods of producing the disclosed compositions can include one or more of the steps of (1) preparation of an ultra-pure solution of sodium chloride in water, (2) temperature control and flow regulation through a set of inert catalytic electrodes and (3) a modulated electrolytic process that results in the formation of such stable molecular moieties and complexes; the RS and ROS. In one embodiment, such a process includes all these steps.

A general example of one such method of making therapeutic compositions is described as comprising: electrolyzing salinated water having a salt concentration of about 2.8 g NaCl/L, using a set of electrodes with an amperage of about 3 amps, to form composition, wherein the water is at or below room temperature during 3 minutes of electrolyzing.

Another general example of one such method of making therapeutic compositions is described as comprising: electrolyzing salinated water having a salt concentration of about 9.1 g NaCl/L, using a set of electrodes with an amperage of about 3 amps, to form a composition, wherein the water is at or below room temperature during 3 minutes of electrolyzing.

Figure 1:
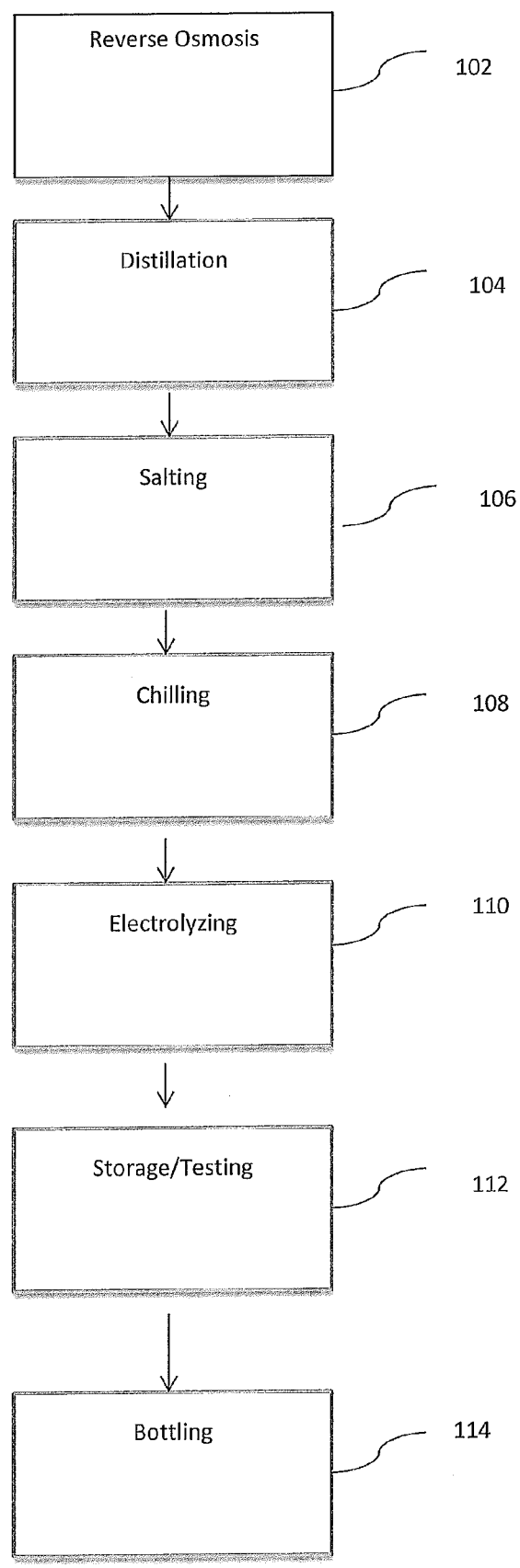
FIG. 1 is a flow chart of a process as described herein.

Water can be supplied from a variety of sources, including but not limited to municipal water, filtered water, nanopure water, or the like. With this in mind, a step in such a process is shown in FIG. 1 wherein the optional reverse osmosis procedure is shown as 102.

In one embodiment, contaminants can be removed from a commercial source of water by the following procedure: water flows through an activated carbon filter to remove the aromatic and volatile contaminants and then undergoes Reverse Osmosis (RO) filtration to remove dissolved solids and most organic and inorganic contaminants. The resulting filtered RO water can contain less than about 8 ppm of dissolved solids. Most of the remaining contaminants can be removed through a distillation process, resulting in dissolved solid measurements less than 1 ppm. In addition to removing contaminants, distillation may also serve to condition the water with the correct structure and Oxidation Reduction Potential (ORP) to facilitate the oxidative and reductive reaction potentials on the platinum electrodes in the subsequent electro-catalytic process.

Ultra-pure refers to the water which has a total dissolved solids count of less than 10 ppm. The total dissolved solids count of less than 10 ppm can be a result of reverse osmosis and/or distillation. Other known processes for water purification can also be used to reduce the amount of total dissolved solids.

The reverse osmosis process can vary, but can provide water having a total dissolved solids content of less than about 10 ppm, about 9 ppm, about 8 ppm, about 7 ppm, about 6 ppm, about 5 ppm, about 4 ppm, about 3 ppm, about 2 ppm, about 1 ppm, or the like.

The reverse osmosis process can be performed at a temperature of about 5° C., about 10° C., about 15° C., about 20° C., about 25° C., about 30° C., about 35° C., or the like. The reverse osmosis step can be repeated as needed to achieve a particular total dissolved solids level. Whether the optional reverse osmosis step is utilized, an optional distillation step 104 can be performed.

Other means of reducing contaminants include filtration and/or purification such as by utilizing deionization, carbon filtration, double-distillation, electrodeionization, resin filtration such as with Milli-Q purification, microfiltration, ultrafiltration, ultraviolet oxidation, electrodialysis, or combinations thereof.

The distillation process can vary, but can provide water having a total dissolved solids content of less than about 5 ppm, about 4 ppm, about 3 ppm, about 2 ppm, about 1 ppm, about 0.9 ppm, about 0.8 ppm, about 0.7 ppm, about 0.6 ppm, about 0.5 ppm, about 0.4 ppm, about 0.3 ppm, about 0.2 ppm, about 0.1 ppm, or the like. The temperature of the distillation process can be performed at a temperature of about 5° C., about 10° C., about 15° C., about 20° C., about 25° C., about 30° C., about 35° C., or the like.

The distillation step can be repeated as needed to achieve a particular total dissolved solids level. After water has been subjected to reverse osmosis, distillation, both, or neither, the level of total dissolved solids in the water can be less than about 5 ppm, about 4 ppm, about 3 ppm, about 2 ppm, about 1 ppm, about 0.9 ppm, about 0.8 ppm, about 0.7 ppm, about 0.6 ppm, about 0.5 ppm, about 0.4 ppm, about 0.3 ppm, about 0.2 ppm, about 0.1 ppm, or the like.

The reverse osmosis, distillation, both, or neither, can be preceded by a carbon filtration step. Purified water can be used directly with the systems and methods described herein.

After water has been subjected to reverse osmosis, distillation, both or neither, or any other purification step as described herein, a salt is added to the water in a salting step 106 of FIG. 1. The salt can be unrefined, refined, caked, de-caked, or the like. In one embodiment, the salt is sodium chloride (NaCl). In some embodiments, the salt can include an additive. Salt additives can include, but are not limited to potassium iodide, sodium iodide, sodium iodate, dextrose, sodium fluoride, sodium ferrocyanide, tricalcium phosphate, calcium carbonate, magnesium carbonate, fatty acids, magnesium oxide, silicone dioxide, calcium silicate, sodium aluminosilicate, calcium aluminosilicate, ferrous fumarate, iron, or folic acid. Any of these additives can be added at this point or at any point during the described process. For example, the above additives can be added just prior to bottling.

The saline generally should be free from contaminants, both organic and inorganic, and homogeneous down to the molecular level. In particular, metal ions can interfere with the electro-catalytic surface reactions, and thus it may be helpful for metals to be avoided. In one embodiment, a brine solution is used to salinate the water. The brine solution can have a NaCl concentration of about 540 g NaCl/gal, such as 537.5 g NaCl/gal.

In another embodiment, the process can be applied to any ionic, soluble salt mixture, especially with those containing chlorides. In addition to NaCl, other non-limiting examples include LiCl, HCl, CuCl2, CuSO4, KCl, MgCl, CaCl2, sulfates and phosphates. For example, strong acids such as sulfuric acid (H2SO4), and strong bases such as potassium hydroxide (KOH), and sodium hydroxide (NaOH) are frequently used as electrolytes due to their strong conducting abilities. Preferably the salt is sodium chloride (NaCl). A brine solution can be used to introduce the salt into the water. The amount of brine or salt needs will be apparent to one of ordinary skill in the art.

Salt can be added to water in the form of a brine solution. To mix the brine solution, a physical mixing apparatus can be used or a circulation or recirculation can be used. In one embodiment, pure pharmaceutical grade sodium chloride is dissolved in the prepared distilled water to form a 15 wt % sub-saturated brine solution and continuously re-circulated and filtered until the salt has completely dissolved and all particles>0.1 microns are removed. This step can take several days. The filtered, dissolved brine solution is then injected into tanks of distilled water in about a 1:352 ratio (salt:water) in order to form a 0.3% saline solution. In one embodiment, a ratio 10.75 g of salt per 1 gallon of water can be used to form the composition. In another embodiment, 10.75 g of salt in about 3-4 g of water, such as 3,787.5 g of water can be used to form the composition. This solution then can be allowed to re-circulate and diffuse until homogeneity at the molecular scale has been achieved. The brine solution can have a NaCl concentration of about 540 g NaCl/gal, such as 537.5 g NaCl/gal.

Brine can then be added to the previously treated water or to fresh untreated water to achieve a NaCl concentration of between about 1 g NaCl/gal water and about 25 g NaCl/gal water, between about 8 g NaCl/gal water and about 12 g NaCl/gal water, or between about 4 g NaCl/gal water and about 16 g NaCl/gal water. In a preferred example, the achieved NaCl concentration is 2.8 g/L of water. In another preferred example, the achieved NaCl concentration is 9.1 g/L of water. Once brine is added to water at an appropriate amount, the solution can be thoroughly mixed. The temperature of the liquid during mixing can be at room temperature or controlled to a desired temperature or temperature range.

To mix the solution, a physical mixing apparatus can be used or a circulation or recirculation can be used. The salt solution can then be chilled in a chilling step 108 of FIG. 1.

For large amounts of composition, various chilling and cooling methods can be employed. For example cryogenic cooling using liquid nitrogen cooling lines can be used. Likewise, the solution can be run through propylene glycol heat exchangers to achieve the desired temperature. The chilling time can vary depending on the amount of liquid, the starting temperature and the desired chilled temperature.

Products from the anodic reactions can be effectively transported to the cathode to provide the reactants necessary to form the stable complexes on the cathode surfaces. Maintaining a high degree of homogeneity in the fluids circulated between the catalytic surfaces can also be helpful. A constant flow of about 2-8 mL/cm2 per sec can be used, with typical mesh electrode distances 2 cm apart in large tanks. This flow can be maintained, in part, by the convective flow of gasses released from the electrodes during electrolysis.

The mixed solution, chilled or not, can then undergo electrochemical processing through the use of at least one electrode in an electrolyzing step 110 of FIG. 1. Each electrode can be or include a conductive metal. Metals can include, but are not limited to copper, aluminum, titanium, rhodium, platinum, silver, gold, iron, a combination thereof or an alloy such as steel or brass. The electrode can be coated or plated with a different metal such as, but not limited to aluminum, gold, platinum or silver. In an embodiment, each electrode is formed of titanium and plated with platinum. The platinum surfaces on the electrodes by themselves can be optimal to catalyze the required reactions. Rough, double layered platinum plating can assure that local "reaction centers" (sharply pointed extrusions) are active and that the reactants not make contact with the underlying electrode titanium substrate.

In one embodiment, rough platinum-plated mesh electrodes in a vertical, coaxial, cylindrical geometry can be optimal, with, for example, not more than 2.5 cm, not more than 5 cm, not more than 10 cm, not more than 20 cm, or not more than 50 cm separation between the anode and cathode. The amperage run through each electrode can be between about 2 amps and about 15 amps, between about 4 amps and about 14 amps, at least about 2 amps, at least about 4 amps, at least about 6 amps, or any range created using any of these values. In one embodiment, 7 amps is used with each electrode. In one example, 1 amp is run through the electrodes. In one example, 2 amps are run through the electrodes. In one example, 3 amps are run through the electrodes. In one example, 4 amps are run through the electrodes. In one example, 5 amps are run through the electrodes. In one example, 6 amps are run through the electrodes. In one example, 7 amps are run through the electrodes. In a preferred example, 3 amps are run through the electrodes.

The amperage can be running through the electrodes for a sufficient time to electrolyze the saline solution. The solution can be chilled during the electrochemical process.

The solution can also be mixed during the electrochemical process. This mixing can be performed to ensure substantially complete electrolysis.

Electric fields between the electrodes can cause movement of ions. Negative ions can move toward the anode and positive ions toward the cathode. This can enable exchange of reactants and products between the electrodes. In some embodiments, no barriers are needed between the electrodes.

After amperage has been run through the solution for a sufficient time, an electrolyzed solution is created. The solution can be stored and or tested for particular properties in storage/testing step 112 of FIG. 1. In one embodiment, the homogenous saline solution is chilled to about 4.8±0.5° C. Temperature regulation during the entire electro-catalytic process is typically required as thermal energy generated from the electrolysis process itself may cause heating. In one embodiment, process temperatures at the electrodes can be constantly cooled and maintained at about 4.8° C. throughout electrolysis.

After amperage has been run through the solution for a sufficient time, an electrolyzed solution is created with beneficial properties, such as antifungal properties. The solution can have a pH of about 7.4. In some embodiments, the pH is greater than 7.3. In some embodiments, the pH is not acidic. In other embodiments, the solution can have a pH less than about 7.5. The pH may not be basic. The solution can be stored and or tested for particular properties in a storage/testing step 112 of FIG. 1.

The end products of this electrolytic process can react within the saline solution to produce many different chemical entities. The compositions and composition described herein can include one or more of these chemical entities, known as redox signaling agents or RXNs.

The chlorine concentration of the electrolyzed solution can be between about 5 ppm and about 34 ppm, between about 10 ppm and about 34 ppm, or between about 15 ppm and about 34 ppm. In one embodiment, the chlorine concentration is about 32 ppm.

The saline concentration in the electrolyzed solution can be, for example, between about 0.10% w/v and about 0.20% w/v, between about 0.11% w/v and about 0.19% w/v, between about 0.12% w/v and about 0.18% w/v, between about 0.13% w/v and about 0.17% w/v, or between about 0.14% w/v and about 0.16% w/v.

The composition can then be bottled in a bottling step 114 of FIG. 1. The composition can be bottled in plastic bottles having volumes of about 4 oz, about 8 oz, about 16 oz, about 32 oz, about 48 oz, about 64 oz, about 80 oz, about 96 oz, about 112 oz, about 128 oz, about 144 oz, about 160 oz, or any range created using any of these values. The plastic bottles can also be plastic squeezable pouches having similar volumes. In one embodiment, plastic squeezable pouches can have one way valves to prevent leakage of the composition, for example, during athletic activity.

During bottling, solution from an approved batch can be pumped through a 10 micron filter (e.g., polypropylene) to remove any larger particles from tanks, dust, hair, etc. that might have found their way into the batch. In other embodiments, this filter need not be used. Then, the solution can be pumped into the bottles, the overflow going back into the batch.

Bottles generally may not contain any dyes, metal specks or chemicals that can be dissolved by acids or oxidating agents. The bottles, caps, bottling filters, valves, lines and heads used can be specifically be rated for acids and oxidating agents. Caps and with organic glues, seals or other components sensitive to oxidation may be avoided, as these could neutralize and weaken the product over time.

The bottles and pouches used herein can aid in preventing decay of free radical species found within the compositions. In other embodiments, the bottles and pouches described do not further the decay process. In other words, the bottles and pouches used can be inert with respect to the radical species in the compositions. In one embodiment, a container (e.g., bottle and/or pouch) can allow less than about 10% decay/month, less than about 9% decay/month, less than about 8% decay/month, less than about 7% decay/month, less than about 6% decay/month, less than about 5% decay/month, less than about 4% decay/month, less than about 3% decay/month, less than about 2% decay/month, less than about 1% decay/month, between about 10% decay/month and about 1% decay/month, between about 5% decay/month and about 1% decay/month, about 10% decay/month, about 9% decay/month, about 8% decay/month, about 7% decay/month, about 6% decay/month, about 5% decay/month, about 4% decay/month, about 3% decay/month, about 2% decay/month, or about 1% decay/month of free radicals in the composition. In one embodiment, a bottle can only result in about 3% decay/month of superoxide. In another embodiment, a pouch can only result in about 4% decay/month of superoxide.

A direct current, DC, power source is used to electrolyze water.

The variables of voltage, amps, frequency, time and current required depend on the compound and/or ion themselves and their respective bond strengths. To that end, the variables of voltage, amps, frequency, time and current are compound and/or ion dependent and are not limiting factors. That notwithstanding, the voltage used can be less than 40V, such as 30V or 20V or 10V or any voltage in between. The voltage can also modulate and at any time vary within a range of from 1 to 40V or from 10 to 30V or from 20 to 30V. In one embodiment, the voltage can range during a single cycle of electrolyzing. The range can be from 1 to 40V or from 10 to 30V or from 20 to 30V. These ranges are non-limiting but are shown as examples.

Waveforms with an AC ripple also referred to as pulse or spiking waveforms include: any positive pulsing currents such as pulsed waves, pulse train, square wave, sawtooth wave, spiked waveforms, pulse-width modulation (PWM), pulse duration modulation (PDM), single phase half wave rectified AC, single phase full wave rectified AC or three phase full wave rectified for example.

A bridge rectifier may be used. Other types of rectifiers can be used such as Single-phase rectifiers, Full-wave rectifiers, Three-phase rectifiers, Twelve-pulse bridge, Voltage-multiplying rectifiers, filter rectifier, a silicon rectifier, an SCR type rectifier, a high-frequency (RF) rectifier, an inverter digital-controller rectifier, vacuum tube diodes, mercury-arc valves, solid-state diodes, silicon-controlled rectifiers and the like. Pulsed waveforms can be made with a transistor regulated power supply, a dropper type power supply, a switching power supply and the like.

A transformer may be used. Examples of transformers that can be used include center tapped transformers, Autotransformer, Capacitor voltage transformer, Distribution transformer, power transformer, Phase angle regulating transformer, Scott-T transformer, Polyphase transformer, Grounding transformer, Leakage transformer, Resonant transformer, Audio transformer, Output transformer, Laminated core Toroidal Autotransformer, Variable autotransformer, Induction regulator, Stray field transformer, Polyphase transformer, Grounding transformer, Leakage transformers, Resonant transformer, Constant voltage transformer, Ferrite core Planar transformer Oil cooled transformer, Cast resin transformer, Isolating transformer, Instrument transformer, Current transformer, Potential transformer Pulse transformer transformer Air-core transformer, Ferrite-core transformer, Transmission-line transformer, Balun Audio transformer, Loudspeaker transformer, Output transformer, Small signal transformer, Interstage coupling transformers, Hedgehog or Variocoupler.

Pulsing potentials in the power supply of the production units can also be built in. Lack of filter capacitors in the rectified power supply can cause the voltages to drop to zero a predetermined amount of times per second. For example, at 60 Hz the voltage can spike 120 times per second, resulting in a hard spike when the alternating current in the house power lines changes polarity. This hard spike, under Fourier transform, can emit a large bandwidth of frequencies. In essence, the voltage is varying from high potential to zero 120 times a second. In other embodiments, the voltage can vary from high potential to zero about 1,000 times a second, about 500 times a second, about 200 times a second, about 150 times a second, about 120 times a second, about 100 times a second, about 80 times a second, about 50 times a second, about 40 times a second, about 20 times a second, between about 200 times a second and about 20 times a second, between about 150 times a second and about 100 times a second, at least about 100 times a second, at least about 50 times a second, or at least about 120 times a second. This power modulation can allow the electrodes sample all voltages and also provides enough frequency bandwidth to excite resonances in the forming molecules themselves. The time at very low voltages can also provide an environment of low electric fields where ions of similar charge can come within close proximity to the electrodes. All of these factors together can provide a possibility for the formation of stable complexes capable of generating and preserving ROS free radicals. In one embodiment, the pulsing potentials can vary based on the desired functional parameters and capabilities of the apparatus and equipment and to that end can vary from very high potentials to low potentials and from very high frequencies to very low frequencies. In one embodiment, the voltage potential must go down to zero periodically. The voltage can go to 0V as many times per second as is physically possible. In some embodiments, the voltage is 0V between 100 and 200 times per second. In a preferred embodiment, the voltage goes down to 0V 120 times per second.

In some embodiments, there is no limit to the how high the voltage potential can go. For example, the voltage potential can pulse from 0V to 40V. In some embodiments, the voltage range can change or be changed so that the range changes as often or as little as desired within any given amount of time.

This pulsing waveform model can be used to stabilize superoxides, hydroxyl radicals and OOH* from many different components and is not limited to any particular variable such as voltage, amps, frequency, flux (current density) or current. The variables are specific to the components used. For example, water and NaCl can be combined which provide molecules and ions in solution. A 60 Hz current can be used, meaning that there are 60 cycles/120 spikes in the voltage (V) per second or 120 times wherein the V is 0 each second. When the V goes down to 0 it is believe that the 0 V allows for ions to drift apart/migrate and reorganize before the next increase in V. It is theorized that this spiking in V allows for and promotes a variable range of frequencies influencing many different types of compounds and/or ions so that this process occurs.

In one embodiment, periodic moments of 0 volts are required. Again, when the V goes down to 0 it is believe that the 0 V allows for ions to drift apart/migrate and reorganize before the next increase in V. Therefore, without being bound to theory, it is believed that this migration of ions facilitates the $1^{st}$, $2^{nd}$, and $3^{rd}$ generations of species as shown in FIG. 2. Stabilized superoxides, such as $O_2^{*-}$, are produced by this method.

In another embodiment, the V is always either 0 V or a positive potential.

Diodes may also be used. The V may drop to 0 as many times per second as the frequency is adjusted. As the frequency is increased the number of times the V drops is increased.

When the ions are affected by the electricity from the electrodes, they change. Without being bound by theory, it is believed that the electricity alters the state of some of the ions/compounds. This alteration results in the pushing of electrons out of their original orbit and/or spin state into a higher energy state and/or a single spin state. This electrolysis provides the energy to form free radicals which are ultimately formed during a multi-generational cycling of reactants and products during the electrolysis process. In other words, compounds and/or ions are initially electrolyzed so that the products that are formed are then themselves reacted with other compounds and/or ions and/or gas to form a second generation of reactants and products. This generational process then happens again so that the products from the second generation react with other compounds and/or ions in solution when the voltage spikes again.

The redox potential can be about 840 mV.

The frequency can be from 1 Hz to infinity or to 100 MHz. Preferably, the frequency is from 20 Hz to 100 Hz. More preferably, the frequency is from 40 Hz to 80 Hz. Most preferably, the frequency is 60 Hz.

In another embodiment, the frequency changes during the course of the electrolyzing process. For example, the frequency at any given moment is in the range from 20 Hz to 100 Hz. In another more preferred embodiment, the frequency at any given moment is in the range from 40 Hz to 80 Hz.

Again referencing FIG. 2, FIG. 2 illustrates an example diagram of the generation of various molecules at the electrodes, the molecules written between the electrodes depict the initial reactants and those on the outside of the electrodes depict the molecules/ions produced at the electrodes and their electrode potentials. The diagram is broken into generations where each generation relies on the products of the subsequent generations.

The end products of this electrolytic process can react within the saline solution to produce many different chemical entities. The compositions described herein can include one or more of these chemical entities. These end products can include, but are not limited to superoxides: $O_2^{*-}$, $HO_2^{*}$; hypochlorites: $OCl-$, $HOCl$, $NaOCl$; hypochlorates: $HClO_2$, $ClO_2$, $HClO_3$, $HClO_4$; oxygen derivatives: $O_2$, $O_3$, $O_4^{*-}$, $1O$; hydrogen derivatives: $H_2$, $H-$; hydrogen peroxide: $H_2O_2$; hydroxyl free Radical: $OH^{*-}$; ionic compounds: $Na+$, $Cl-$, $H+$, $OH-$, $NaCl$, $HCl$, $NaOH$; chlorine: $Cl_2$; and water clusters: $n*H_2O$-induced dipolar layers around ions, several variations.

In one embodiment, the composition can include at least one species such as $O_2$, $H_2$, $Cl_2$, $OCl-$, $HOCl$, $NaOCl$, $HClO_2$, $ClO_2$, $HClO_3$, $HClO_4$, $H_2O_2$, $Na+$, $Cl-$, $H+$, H, OH—, O3, O4*, 1O, OH*-, HOCl—O2*-, HOCl—O3, O2*, HO2*, NaCl, HCl, NaOH, water clusters, or a combination thereof.

In one embodiment, the composition can include at least one species such as H2, Cl2, OCl—, HOCl, NaOCl, HClO2, ClO2, HClO3, HClO4, H2O2, O3, O4*, 1O2, OH*-, HOCl—$O_2$*-, HOCl—O3, O2*, HO2*, water clusters, or a combination thereof.

In one embodiment, the composition can include at least one species such as HClO3, HClO4, H2O2, O3, O4*, 1O2, OH*-, HOCl—O2*-, HOCl—O3, O2*, HO2*, water clusters, or a combination thereof.

In one embodiment, the composition can include at least O2*- and HOCl.

In one embodiment, the composition can include O2. In one embodiment, the composition can include H2. In one embodiment, the composition can include Cl2. In one embodiment, the composition can include OCl—. In one embodiment, the composition can include HOCl. In one embodiment, the composition can include NaOCl. In one embodiment, the composition can include HClO2. In one embodiment, the composition can include ClO2. In one embodiment, the composition can include HClO3. In one embodiment, the composition can include HClO4. In one embodiment, the composition can include H2O2. In one embodiment, the composition can include Na+. In one embodiment, the composition can include Cl—. In one embodiment, the composition can include H+. In one embodiment, the composition can include H. In one embodiment, the composition can include OH—. In one embodiment, the composition can include O3. In one embodiment, the composition can include O4*. In one embodiment, the composition can include 1O2. In one embodiment, the composition can include OH*-. In one embodiment, the composition can include HOCl—O2*-. In one embodiment, the composition can include HOCl—O3. In one embodiment, the composition can include O2*-. In one embodiment, the composition can include HO2*. In one embodiment, the composition can include NaCl. In one embodiment, the composition can include HCl. In one embodiment, the composition can include NaOH. In one embodiment, the composition can include water clusters. Embodiments can include combinations thereof.

In some embodiments, hydroxyl radicals can be stabilized in the composition by the formation of radical complexes. The radical complexes can be held together by hydrogen bonding. Another radical that can be present in the composition is an OOH* radical. Still other radical complexes can include a nitroxyl-peroxide radical (HNO—HOO*) and/or a hypochlorite-peroxide radical (HOCl—HOO*).

The composition is stable which means, among other things, that the active agents are present, measurable or detected throughout the lifespan of the composition. In one embodiment, the active agent(s) or active ingredient(s) are superoxides and/or hydroxyl radicals. For example, the invention may be expressed as a composition wherein at least some percentage of the active ingredient(s) is present in the composition after a certain number of years, such as wherein at least 95% of the active ingredient(s) is present in the composition after 2 years, wherein at least 90% of the active ingredient(s) is present in the composition after 3 years, wherein at least 85% of the active ingredient(s) is present in the composition after 4 years, wherein at least 80% of the active ingredient(s) is present in the composition after 5 years, wherein at least 75% of the active ingredient(s) is present in the composition after 6 years, wherein at least 70% of the active ingredient(s) is present in the composition after 7 years, wherein at least 65% of the active ingredient(s) is present in the composition after 8 years, wherein at least 60% of the active ingredient(s) is present in the composition after 9 years, wherein at least 55% of the active ingredient(s) is present in the composition after 10 years and the like.

Stable oxygen radicals can remain stable for about 3 months, about 6 months, about 9 months, about 12 months, about 15 months, about 18 months, about 21 months, between about 9 months and about 15 months, between about 12 months and about 18 months, at least about 9 months, at least about 12 months, at least about 15 months, at least about 18 months, about 24 months, about 30 months, about 50 months, about 100 months, about 200 months, about 300 months, about 400 months, about 500 months, about 1000 months, about 2000 months, or longer.

Stable oxygen radicals can be substantially stable. Substantially stable can mean that the stable oxygen radical can remain at a concentration greater than about 75% relative to the concentration on day 1 (day 1 meaning on the day or at the time it was produced), greater than about 80%, greater than about 85%, greater than about 90%, greater than about 95%, greater than about 96%, greater than about 97%, greater than about 98%, or greater than about 99% over a given time period as described above. For example, in one embodiment, the stable oxygen is at a concentration greater than about 95% relative to day 1 for at least 1 year. In another embodiment, the at least one oxygen radical is at a concentration greater than about 98% for at least 1 year.

Stable can mean that the stable oxygen radical can remain at a concentration greater than about 75% relative to the concentration on day 1 or the day is was produced, greater than about 80% relative to the concentration on day 1 or the day is was produced, greater than about 85% relative to the concentration on day 1 or the day is was produced, greater than about 90% relative to the concentration on day 1 or the day is was produced, greater than about 95% relative to the concentration on day 1 or the day is was produced, greater than about 96% relative to the concentration on day 1 or the day is was produced, greater than about 97% relative to the concentration on day 1 or the day is was produced, greater than about 98% relative to the concentration on day 1 or the day is was produced, or greater than about 99% relative to the concentration on day 1 or the day is was produced over a given time period as described above. For example, in one embodiment, the stable oxygen is at a concentration greater than about 95% relative to day 1 for at least 1 year. In another embodiment, the at least one oxygen radical is at a concentration greater than about 98% for at least 1 year.

Stability as used herein can also refer to the amount of a particular specie when compared to a reference sample. In some embodiments, the reference sample can be made in 1 L vessels with 0.9% isotonic solution electrolyzed with 3 Amps at 40° F., for 3 mins. In another embodiment, the reference sample can be made according to a process as otherwise described herein. The reference standard can also be bottled directly off the processing line as a "fresh" sample.

In other embodiments, the at least one oxygen radical is greater than about 86% stable for at least 4 years, greater than about 79% stable for at least 6 years, greater than about 72% stable for at least 8 years, greater than about 65% stable for at least 10 years, or 100% stable for at least 20 years.

In still other embodiments, the at least one oxygen radical is greater than about 95% stable for at least 2 years, at least 3 years, at least 4 years, at least 5 years, at least 6 years, at least 7 years, at least 8 years, at least 9 years, at least 10 years, at least 15 years, or at least 20 years. In still other embodiments, the at least one oxygen radical is greater than about 96% stable for at least 2 years, at least 3 years, at least 4 years, at least 5 years, at least 6 years, at least 7 years, at least 8 years, at least 9 years, at least 10 years, at least 15 years, or at least 20 years. In still other embodiments, the at least one oxygen radical is greater than about 97% stable for at least 2 years, at least 3 years, at least 4 years, at least 5 years, at least 6 years, at least 7 years, at least 8 years, at least 9 years, at least 10 years, at least 15 years, or at least 20 years. In still other embodiments, the at least one oxygen radical is greater than about 98% stable for at least 2 years, at least 3 years, at least 4 years, at least 5 years, at least 6 years, at least 7 years, at least 8 years, at least 9 years, at least 10 years, at least 15 years, or at least 20 years. In still other embodiments, the at least one oxygen radical is greater than about 99% stable for at least 2 years, at least 3 years, at least 4 years, at least 5 years, at least 6 years, at least 7 years, at least 8 years, at least 9 years, at least 10 years, at least 15 years, or at least 20 years. In still other embodiments, the at least one oxygen radical is 100% stable for at least 2 years, at least 3 years, at least 4 years, at least 5 years, at least 6 years, at least 7 years, at least 8 years, at least 9 years, at least 10 years, at least 15 years, or at least 20 years.

The stability of oxygen radicals can also be stated as a decay rate over time. Decay of superoxides is described in Ong, Ta-Chung, "Detailed Mechanistic and Optimization of the Photochemical Production Method of Superoxide" (2007). Honors Theses. Paper 267. http://digitalcommons.colby.edu/honorstheses/267 Retrieved 14 Aug. 2013 which is incorporated herein in its entirety. Substantially stable can mean a decay rate less than 1% per month, less than 2% per month, less than 3% per month, less than 4% per month, less than 5% per month, less than 6% per month, less than 10% per month, less than 3% per year, less than 4% per year, less than 5% per year, less than 6% per year, less than 7% per year, less than 8% per year, less than 9% per year, less than 10% per year, less than 15% per year, less than 20% per year, less than 25% per year, between less than 3% per month and less than 7% per year.

In other embodiments, stability can be expressed as a half-life. A half-life of the stable oxygen radical can be about 6 months, about 1 year, about 2 years, about 3 years, about 4 years, about 5 years, about 10 years, about 15 years, about 20 years, about 24 years, about 30 years, about 40 years, about 50 years, greater than about 1 year, greater than about 2 years, greater than about 10 years, greater than about 20 years, greater than about 24 years, between about 1 year and about 30 years, between about 6 years and about 24 years, or between about 12 years and about 30 years.

Reactive species' concentrations in the life enhancing solutions, detected by fluorescence photo spectroscopy, may not significantly decrease in time. Mathematical models show that bound HOCl—*O2— complexes are possible at room temperature. Molecular complexes can preserve volatile components of reactive species. For example, reactive species concentrations in whole blood as a result of molecular complexes may prevent reactive species degradation over time.

Reactive species can be further divided into "reduced species" (RS) and "reactive oxygen species" (ROS). Reactive species can be formed from water molecules and sodium chloride ions when restructured through a process of forced electron donation. Electrons from lower molecular energy configurations in the salinated water may be forced into higher, more reactive molecular configurations. The species from which the electron was taken can be "electron hungry" and is called the RS and can readily become an electron acceptor (or proton donor) under the right conditions. The species that obtains the high-energy electron can be an electron donor and is called the ROS and may energetically release these electrons under the right conditions.

When an energetic electron in ROS is unpaired it is called a "radical". ROS and RS can recombine to neutralize each other by the use of a catalytic enzyme. Three elements, (1) enzymes, (2) electron acceptors, and (3) electron donors can all be present at the same time and location for neutralization to occur.

Depending on the parameters used to produce the composition, different components can be present at different concentrations. In one embodiment, the composition can include about 0.1 ppt, about 0.5 ppt, about 1 ppt, about 1.5 ppt, about 2 ppt, about 2.5 ppt, about 3 ppt, about 3.5 ppt, about 4 ppt, about 4.5 ppt, about 5 ppt, about 6 ppt, about 7 ppt, about 8 ppt, about 9 ppt, about 10 ppt, about 20 ppt, about 50 ppt, about 100 ppt, about 200 ppt, about 400 ppt, about 1,000 ppt, between about 0.1 ppt and about 1,000 ppt, between about 0.1 ppt and about 100 ppt, between about 0.1 ppt and about 10 ppt, between about 2 ppt and about 4 ppt, at least about 0.1 ppt, at least about 2 ppt, at least about 3 ppt, at most about 10 ppt, or at most about 100 ppt of OCl—. In some embodiments, OCl— can be present at 3 ppt. In other embodiments, OCl— can be present at 1 to 100 ppm or from 10 to 30 ppm or from 16 to 24 ppm. In particular embodiments, OCl— is present at 16 ppm, 17 ppm, 18 ppm, 19 ppm, 20 ppm, 21 ppm, 22 ppm, 23 pm, 24 ppm or 25 ppm. In other embodiments, OCl— can be the predominant chlorine containing species in the composition.

In order to determine the relative concentrations and rates of production of each of these during electrolysis, certain general chemical principles can be helpful:

1) A certain amount of Gibbs free energy is required for construction of the molecules; Gibbs free energy is proportional to the differences in electrode potentials listed in FIG. 2. Reactions with large energy requirements are less likely to happen, for example an electrode potential of −2.71V (compared to Hydrogen reduction at 0.00V) is required to make sodium metal:

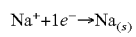

$Na^+ + 1e^- \rightarrow Na_{(s)}$

Such a large energy difference requirement makes this reaction less likely to happen compared to other reactions with smaller energy requirements. Electron(s) from the electrodes may be preferentially used in the reactions that require lesser amounts of energy, such as the production of hydrogen gas.

2) Electrons and reactants are required to be at the same micro-locality on the electrodes. Reactions that require several reactants may be less likely to happen, for example:

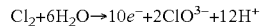

$Cl_2 + 6H_2O \rightarrow 10e^- + 2ClO_3^- + 12H^+$ requires that 6 water molecules and a Cl2 molecule to be at the electrode at the same point at the same time and a release of 10 electrons to simultaneously occur. The probability of this happening generally is smaller than other reactions requiring fewer and more concentrated reactants to coincide, but such a reaction may still occur.

3) Reactants generated in preceding generations can be transported or diffuse to the electrode where reactions happen. For example, dissolved oxygen (O2) produced on the anode from the first generation can be transported to the cathode in order to produce superoxides and hydrogen peroxide in the second generation. Ions can be more readily transported: they can be pulled along by the electric field due to their electric charge. In order for chlorates, to be generated, for example, HClO2 can first be produced to start the cascade, restrictions for HClO2 production can also restrict any subsequent chlorate production. Lower temperatures can prevent HClO2 production.

Stability and concentration of the above products can depend, in some cases substantially, on the surrounding environment. The formation of complexes and water clusters can affect the lifetime of the moieties, especially the free radicals.

In a pH-neutral aqueous solution (pH around 7.0) at room temperature, superoxide free radicals ($O_2^{*-}$) have a half-life of 10's of milliseconds and dissolved ozone ($O_3$) has a half-life of about 20 min. Hydrogen peroxide ($H_2O_2$) is relatively long-lived in neutral aqueous environments, but this can depend on redox potentials and UV light. Other entities such as HCl and NaOH rely on acidic or basic environments, respectively, in order to survive. In pH-neutral solutions, H+ and OH— ions have concentrations of approximately 1 part in 10,000,000 in the bulk aqueous solution away from the electrodes. H— and 1O can react quickly. The stability of most of these moieties mentioned above can depend on their microenvironment.

Superoxides and ozone can form stable Van de Waals molecular complexes with hypochlorites. Clustering of polarized water clusters around charged ions can also have the effect of preserving hypochlorite-superoxide and hypochlorite-ozone complexes. Such complexes can be built through electrolysis on the molecular level on catalytic substrates, and may not occur spontaneously by mixing together components. Hypochlorites can also be produced spontaneously by the reaction of dissolved chlorine gas ($Cl_2$) and water. As such, in a neutral saline solution the formation of on or more of the stable molecules and complexes may exist: dissolved gases: $O_2$, $H_2$, $Cl_2$; hypochlorites: OCl—, HOCl, NaOCl; hypochlorates: $HClO_2$, $ClO_2$, $HClO_3$, $HClO_4$; hydrogen peroxide: $H_2O_2$; ions: Na+, Cl—, H+, H—, OH—; ozone: $O_3$, $O_4^{*-}$; singlet oxygen: 1O; hydroxyl free radical: $OH^*-$; superoxide complexes: HOCl—$O_2^*-$; and ozone complexes: HOCl—$O_3$. One or more of the above molecules can be found within the compositions and composition described herein.

A complete quantum chemical theory can be helpful because production is complicated by the fact that different temperatures, electrode geometries, flows and ion transport mechanisms and electrical current modulations can materially change the relative/absolute concentrations of these components, which could result in producing different distinct compositions. As such, the selection of production parameters can be critical. The amount of time it would take to check all the variations experimentally may be prohibitive.

The chlorine concentration of the electrolyzed solution can be about 5 ppm, about 10 ppm, about 15 ppm, about 20 ppm, about 21 ppm, about 22 ppm, about 23 ppm, about 24 ppm, about 25 ppm, about 26 ppm, about 27 ppm, about 28 ppm, about 29 ppm, about 30 ppm, about 31 ppm, about 32 ppm, about 33 ppm, about 34 ppm, about 35 ppm, about 36 ppm, about 37 ppm, about 38 ppm, less than about 38 ppm, less than about 35 ppm, less than about 32 ppm, less than about 28 ppm, less than about 24 ppm, less than about 20 ppm, less than about 16 ppm, less than about 12 ppm, less than about 5 ppm, between about 30 ppm and about 34 ppm, between about 28 ppm and about 36 ppm, between about 26 ppm and about 38 ppm, between about 20 ppm and about 38 ppm, between about 5 ppm and about 34 ppm, between about 10 ppm and about 34 ppm, or between about 15 ppm and about 34 ppm. In one embodiment, the chlorine concentration is about 32 ppm. In another embodiment, the chlorine concentration is less than about 41 ppm.

In some embodiments, the chloride species can be present from 1400 to 1650 ppm. In a particular embodiment, the chloride species can be present from 1400 to 1500 ppm or from 1500 to 1600 ppm or from 1600 to 1650 ppm. In other embodiments, the chloride anion can be present in an amount that is predetermined based on the amount of NaCl added to the initial solution.

In some embodiments, the sodium species can be present from 1000 to 1400 ppm. In a particular embodiment, the sodium species can be present from 1100 to 1200 ppm or from 1200 to 1300 ppm or from 1300 to 1400 ppm. For example, the sodium species can be present at 1200 ppm. In other embodiments, the sodium anion can be present in an amount that is predetermined based on the amount of NaCl added to the initial solution.

The saline concentration in the electrolyzed solution can be about 0.10% w/v, about 0.11% w/v, about 0.12% w/v, about 0.13% w/v, about 0.14% w/v, about 0.15% w/v, about 0.16% w/v, about 0.17% w/v, about 0.18% w/v, about 0.19% w/v, about 0.20% w/v, about 0.30% w/v, about 0.40% w/v, about 0.50% w/v, about 0.60% w/v, about 0.70% w/v, between about 0.10% w/v and about 0.20% w/v, between about 0.11% w/v and about 0.19% w/v, between about 0.12% w/v and about 0.18% w/v, between about 0.13% w/v and about 0.17% w/v, or between about 0.14% w/v and about 0.16% w/v.

The composition generally can include electrolytic and/or catalytic products of pure saline that mimic redox signaling molecular compositions of the native salt water compounds found in and around human cells. The composition can be fine-tuned to mimic or mirror molecular compositions of different biological media. The composition can have reactive species other than chlorine present. As described, species present in the compositions and compositions described herein can include, but are not limited to $O_2$, $H_2$, $Cl_2$, OCl—, HOCl, NaOCl, $HClO_2$, $ClO_2$, $HClO_3$, $HClO_4$, $H_2O_2$, Na+, Cl—, H+, H—, OH—, $O_3$, $O_4^*-$, 1O, $OH^*-$, HOCl—$O_2^*-$, HOCl—$O_3$, $O_2^*$, $HO_2^*$, NaCl, HCl, NaOH, and water clusters: n*$H_2O$-induced dipolar layers around ions, several variations.

In some embodiments, substantially no organic material is present in the compositions described. Substantially no organic material can be less than about 0.1 ppt, less than about 0.01 ppt, less than about 0.001 ppt or less than about 0.0001 ppt of total organic material.

The composition can be stored and bottled as needed to ship to consumers. The composition can have a shelf life of about 5 days, about 30 days, about 3 months, about 6 months, about 9 months, about 1 year, about 1.5 years, about 2 years, about 3 years, about 5 years, about 10 years, at least about 5 days, at least about 30 days, at least about 3 months, at least about 6 months, at least about 9 months, at least about 1 year, at least about 1.5 years, at least about 2 years, at least about 3 years, at least about 5 years, at least about 10 years, between about 5 days and about 1 year, between about 5 days and about 2 years, between about 1 year and about 5 years, between about 90 days and about 3 years, between about 90 days and about 5 year, or between about 1 year and about 3 years.

Quality Assurance testing can be done on every batch before the batch can be approved for bottling or can be performed during or after bottling. A 16 oz. sample bottle can be taken from each complete batch and analyzed. Determinations for presence of contaminants such as heavy metals or chlorates can be performed. Then pH, Free and Total Chlorine concentrations and reactive molecule concentrations of the active ingredients can be analyzed by fluorospectroscopy methods. These results can be compared to those of a standard solution which is also tested along side every sample. If the results for the batch fall within a certain range relative to the standard solution, it can be approved. A chemical chromospectroscopic MS analysis can also be run on random samples to determine if contaminants from the production process are present.

The composition can be consumed by ingestion. In other embodiments, the composition can be provided as a solution for injection. In some embodiments, injection can be subcutaneous, intra-luminal, site specific, or intramuscular. Intravenous injection can also be desirable. Most preferably, the composition is used topically. The composition can be packaged in plastic medical solution pouches having volumes of about 4 oz, about 8 oz, about 16 oz, about 32 oz, about 48 oz, about 64 oz, about 80 oz, about 96 oz, about 112 oz, about 128 oz, about 144 oz, about 160 oz, or any range created using any of these values, and these pouches can be used with common intravenous administration systems.

When administered, it can be administered once, twice, three times, four times or more a day. Each administration can be about 1 oz, about 2 oz, about 3 oz, about 4 oz, about 5 oz, about 6 oz, about 7 oz, about 8 oz, about 9 oz, about 10 oz, about 11 oz, about 12 oz, about 16 oz, about 20 oz, about 24 oz, about 28 oz, about 32 oz, about 34 oz, about 36 oz, about 38 oz, about 40 oz, about 46 oz, between about 1 oz and about 32 oz, between about 1 oz and about 16 oz, between about 1 oz and about 8 oz, at least about 2 oz, at least about 4 oz, or at least about 8 oz. In one embodiment, the composition can be administered at a rate of about 4 oz twice a day.

In other embodiments, the administration can be acute or long term. For example, the composition can be administered for a day, a week, a month, a year or longer. In other embodiments, the composition can simply be taken as needed.

Compositions of the invention can be formulated into any suitable aspect, such as, for example, aerosols, liquids, elixirs, syrups, tinctures and the like.

When administered as a liquid composition, it can be administered once, twice, three times, four times or more a day. Each administration can be about 1 oz, about 2 oz, about 3 oz, about 4 oz, about 5 oz, about 6 oz, about 7 oz, about 8 oz, about 9 oz, about 10 oz, about 11 oz, about 12 oz, about 16 oz, about 20 oz, about 24 oz, about 28 oz, about 32 oz, about 34 oz, about 36 oz, about 38 oz, about 40 oz, about 46 oz, between about 1 oz and about 32 oz, between about 1 oz and about 16 oz, between about 1 oz and about 8 oz, at least about 2 oz, at least about 4 oz, or at least about 8 oz. In one embodiment, the composition can be administered at a rate of about 4 oz twice a day.

In other embodiments, the administration can be acute or long term. For example, the composition can be administered for a day, a week, a month, a year or longer.

Example 1

Figure 3:
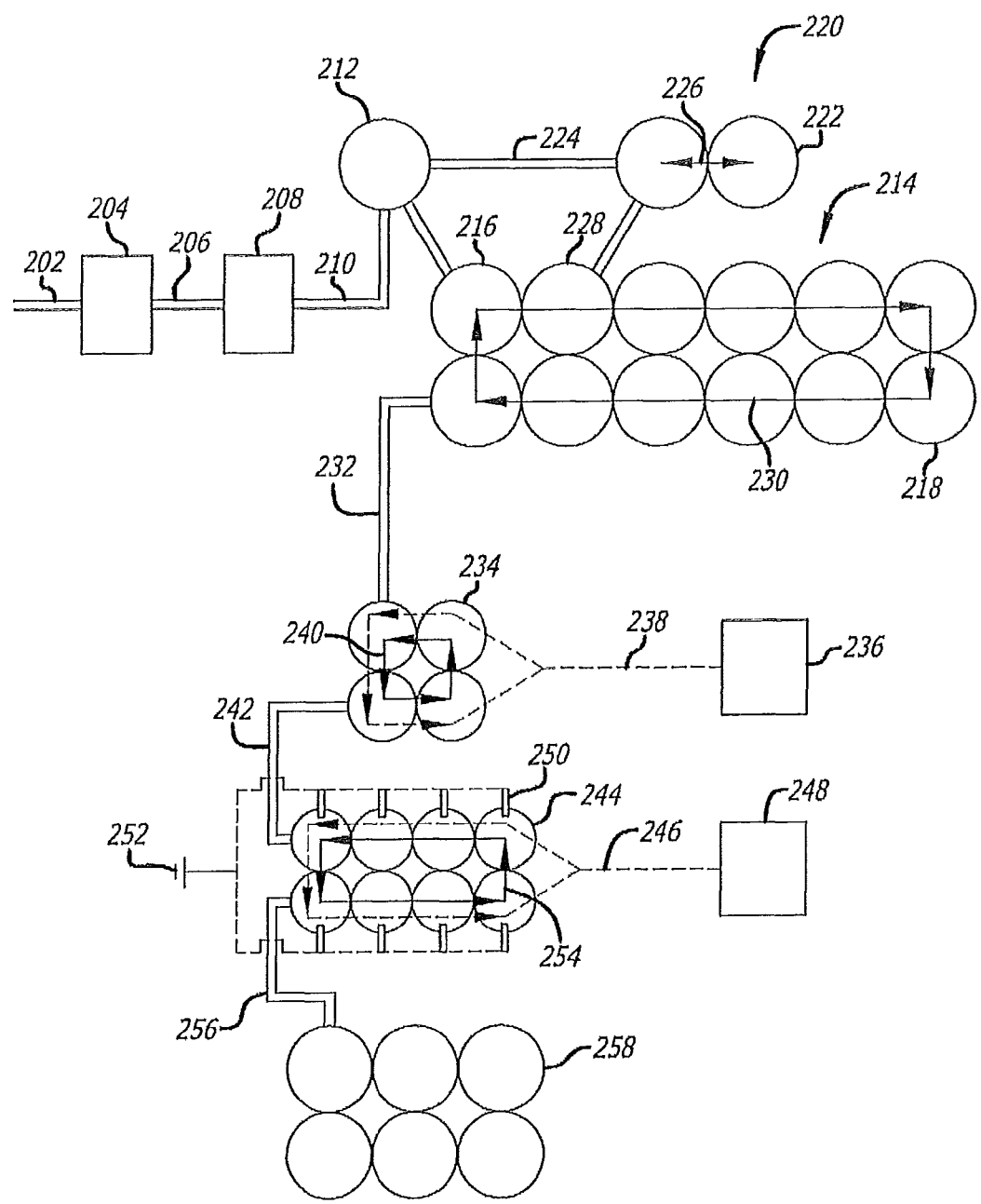
FIG. 3 illustrates a plan view of a process and system for producing a composition according to the present description.

FIG. 3 illustrates a plan view of a process and system for producing a composition according to the present description. One skilled in the art understands that changes can be made to the system to alter the composition, and these changes are within the scope of the present description.

Incoming water 202 can be subjected to reverse osmosis system 204 at a temperature of about 15-20° C. to achieve purified water 206 with about 8 ppm of total dissolved solids. Purified water 206, is then fed at a temperature of about 15-20° C. into distiller 208 and processed to achieve distilled water 210 with about 0.5 ppm of total dissolved solids. Distilled water 210 can then be stored in tank 212.

Figure 4:
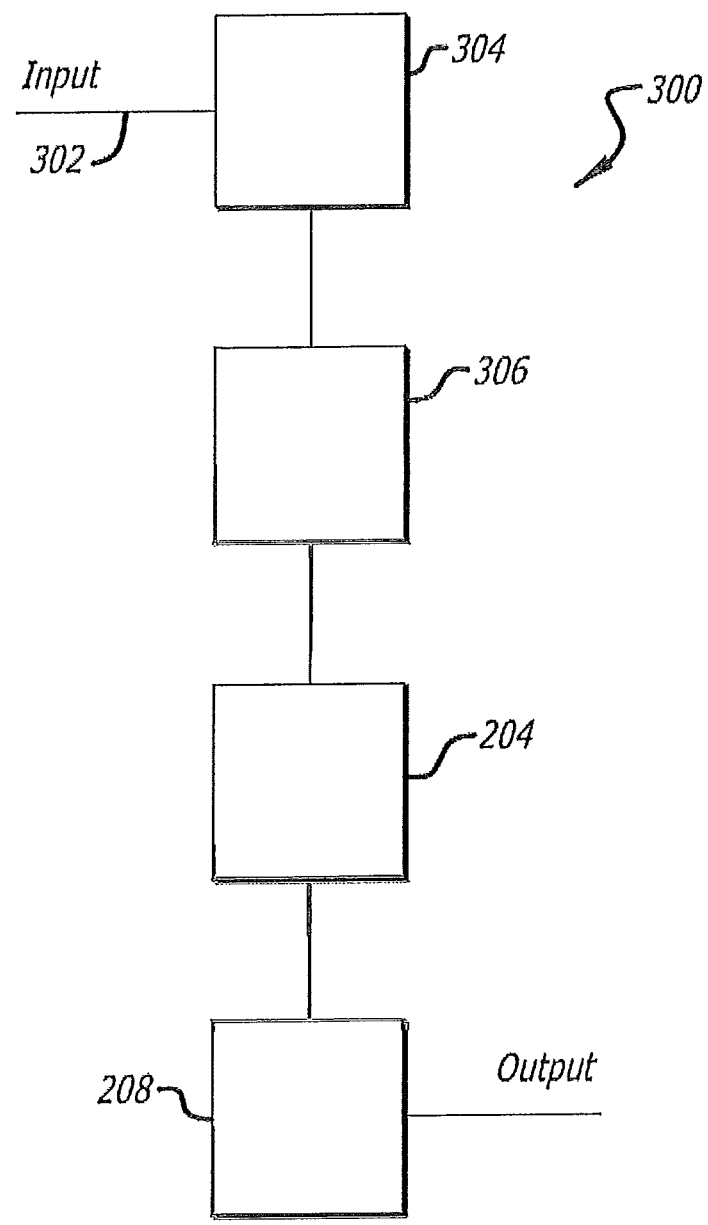
FIG. 4 illustrates an example system for preparing water for further processing into a composition described herein.

FIG. 4 illustrates an example system for preparing water for further processing into a therapeutic composition. System 300 can include a water source 302 which can feed directly into a carbon filter 304. After oils, alcohols, and other volatile chemical residuals and particulates are removed by carbon filter 304, the water can be directed to resin beds within a water softener 306 which can remove dissolved minerals. Then, as described above, the water can pass through reverse osmosis system 204 and distiller 208.

Referring again to FIG. 3, distilled water 210 can be gravity fed as needed from tank 212 into saline storage tank cluster 214 using line 216. Saline storage tank cluster 214 in one embodiment can include twelve tanks 218. Each tank 218 can be filled to about 1,300 gallons with distilled water 210. A handheld meter can be used to test distilled water 210 for salinity.

Saline storage tank cluster 214 is then salted using a brine system 220. Brine system 220 can include two brine tanks 222. Each tank can have a capacity of about 500 gallons. Brine tanks 222 are filled to 475 gallons with distilled water 210 using line 224 and then NaCl is added to the brine tanks 222 at a ratio of about 537.5 g/gal of liquid. At this point, the water is circulated 226 in the brine tanks 222 at a rate of about 2,000 gal/hr for about 4 days.

Prior to addition of brine to tanks 218, the salinity of the water in tanks 218 can be tested using a handheld conductivity meter such as an YSI ECOSENSE® ecp300 (YSI Inc., Yellow Springs, Ohio). Any corrections based on the salinity measurements can be made at this point. Brine solution 228 is then added to tanks 218 to achieve a salt concentration of about 10.75 g/gal. The salted water is circulated 230 in tanks 218 at a rate of about 2,000 gal/hr for no less than about 72 hours. This circulation is performed at room temperature. A handheld probe can again be used to test salinity of the salinated solution. In one embodiment, the salinity is about 2.8 ppth.

In one method for filling and mixing the salt water in the brine holding tanks, the amount of liquid remaining in the tanks is measured. The amount of liquid remaining in a tank is measured by recording the height that the liquid level is from the floor that sustains the tank, in centimeters, and referencing the number of gallons this height represents. This can be done from the outside of the tank if the tank is semi-transparent. The initial liquid height in both tied tanks can also be measured. Then, after ensuring that the output valve is closed, distilled water can be pumped in. The amount of distilled water that is being pumped into a holding tank can then be calculated by measuring the rise in liquid level: subtracting the initial height from the filled height and then multiplying this difference by a known factor.

The amount of salt to be added to the tank is then calculated by multiplying 11 grams of salt for every gallon of distilled water that has been added to the tank. The salt can be carefully weighed out and dumped into the tank.

The tank is then agitated by turning on the recirculation pump and then opening the top and bottom valves on the tank. Liquid is pumped from the bottom of the tank to the top. The tank can be agitated for three days before it may be ready to be processed.

After agitating the tank for more than 6 hours, the salinity is checked with a salinity meter by taking a sample from the tank and testing it. Salt or water can be added to adjust the salinity within the tanks. If either more water or more salt is added then the tanks are agitated for 6 more hours and tested again. After about three days of agitation, the tank is ready to be processed.

Salinated water 232 is then transferred to cold saline tanks 234. In one embodiment, four 250 gal tanks are used. The amount of salinated water 232 moved is about 1,000 gal. A chiller 236 such as a 16 ton chiller is used to cool heat exchangers 238 to about 0-5° C. The salinated water is circulated 240 through the heat exchangers which are circulated with propylene glycol until the temperature of the salinated water is about 4.5-5.8° C. Chilling the 1,000 gal of salinated water generally takes about 6-8 hr.

Cold salinated water 242 is then transferred to processing tanks 244. In one embodiment, eight tanks are used and each can have a capacity of about 180 gal. Each processing tank 244 is filled to about 125 gal for a total of 1,000 gal. Heat exchangers 246 are again used to chill the cold salinated water 242 added to processing tanks 244. Each processing tank can include a cylinder of chilling tubes and propylene glycol can be circulated. The heat exchangers can be powered by a 4-5 ton chiller 248. The temperature of cold salinated water 242 can remain at 4.5-5.8° C. during processing.

Prior to transferring aged salt water to processing tanks, the aged salt water can be agitated for about 30 minutes to sufficiently mix the aged salt water. Then, the recirculation valves can then be closed, the appropriate inlet valve on the production tank is opened, and the tank filled so that the salt water covers the cooling coils and comes up to the fill mark (approximately 125 gallons).

Once the aged salt water has reached production temperature, the pump is turned off but the chiller left on. The tank should be adequately agitated or re-circulated during the whole duration of electrochemical processing and the temperature should remain constant throughout.

Each processing tank 244 includes electrode 250. Electrodes 250 can be 3 inches tall circular structures formed of titanium and plated with platinum. Electrochemical processing of the cold salinated water can be run for 8 hr. A power supply 252 is used to power the eight electrodes (one in each processing tank 244) to 7 amps each for a total of 56 amps. The cold salinated water is circulated 254 during electrochemical processing at a rate of about 1,000 gal/hr.

An independent current meter can be used to set the current to around 7.0 Amps. Attention can be paid to ensure that the voltage does not exceed 12V and does not go lower than 9V. Normal operation can be about 10V. Alternatively, normal operation can be at 1V, 2V, 3V, 4V, 5V, 6V, 7V, 8V, 9V, 10V, 11V or 12V.

A run timer can be set for a prescribed time (about 4.5 to 5 hours). Each production tank can have its own timer and/or power supply. Electrodes should be turned off after the timer has expired.

The production tanks can be checked periodically. The temperature and/or electrical current can be kept substantially constant. At the beginning, the electrodes can be visible from the top, emitting visible bubbles. After about 3 hours, small bubbles of un-dissolved oxygen can start building up in the tank as oxygen saturation occurs, obscuring the view of the electrodes. A slight chlorine smell can be normal.

After the 8 hour electrochemical processing is complete, life enhancing water 256 has been created with a pH of about 6.8-8.2 and 32 ppm of chlorine. The composition 256 is transferred to storage tanks 258. The product ASEA can be made by this process. Preferably, the product ASEA is made by the process of this Example 1.

Example 2

Characterization of a Solution Produced as Described in Example 1

A composition produced as described in Example 1 was analyzed using a variety of different characterization techniques. ICP/MS and 35Cl NMR were used to analyze and quantify chlorine content. Headspace mass spectrometry analysis was used to analyze adsorbed gas content in the composition. 1H NMR was used to verify the organic matter content in the composition. 31P NMR and EPR experiments utilizing spin trap molecules were used to explore the composition for free radicals.

The composition was received and stored at about 4° C. when not being used.

Chlorine NMR

Sodium hypochlorite solutions were prepared at different pH values. 5% sodium hypochlorite solution had a pH of 12.48. Concentrated nitric acid was added to 5% sodium hypochlorite solution to create solutions that were at pH of 9.99, 6.99, 5.32, and 3.28. These solutions were then analyzed by NMR spectroscopy. The composition had a measured pH of 8.01 and was analyzed directly by NMR with no dilutions.

NMR spectroscopy experiments were performed using a 400 MHz Bruker spectrometer equipped with a BBO probe. 35Cl NMR experiments were performed at a frequency of 39.2 MHz using single pulse experiments. A recycle delay of 10 seconds was used, and 128 scans were acquired per sample. A solution of NaCl in water was used as an external chemical shift reference. All experiments were performed at room temperature.

Figure 5:
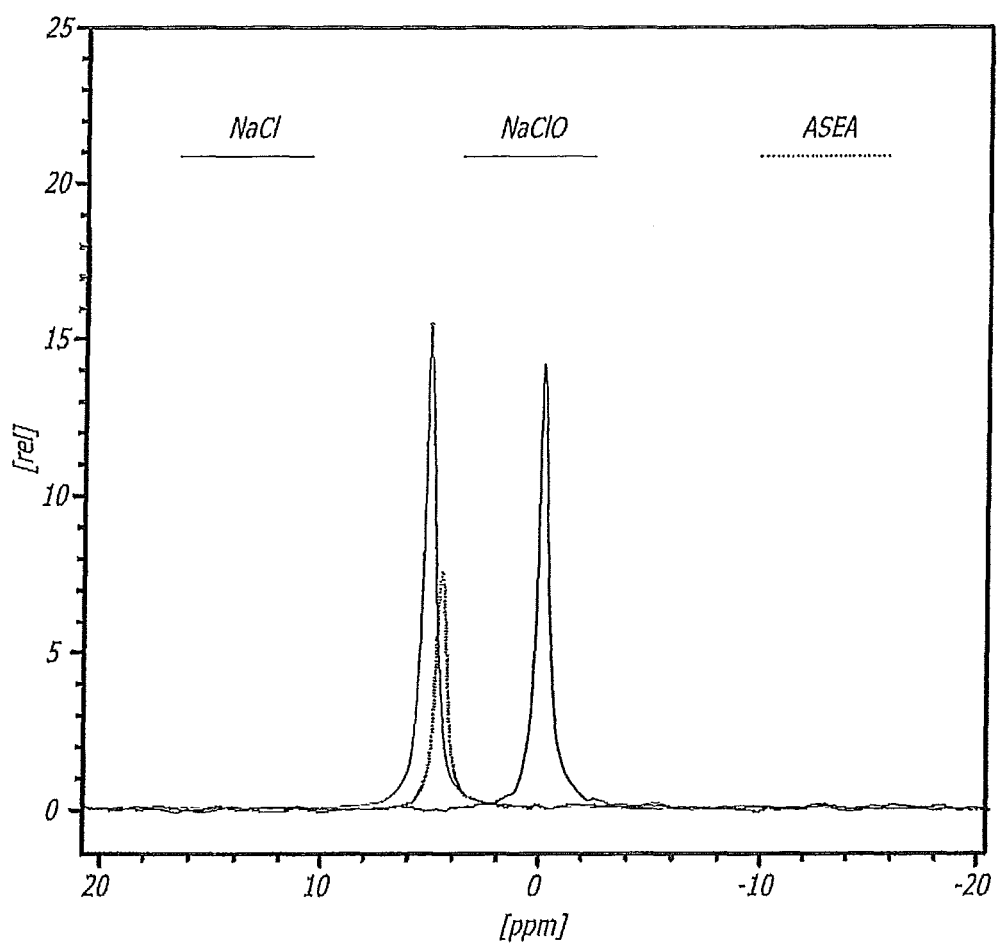
FIG. 5 illustrates a Cl35 spectrum of NaCl, NaClO solution at a pH of 12.48, and a composition described herein (the composition is labeled "ASEA").

35Cl NMR spectra were collected for NaCl solution, NaClO solutions adjusted to different pH values, and the composition. FIG. 5 illustrates a Cl35 spectrum of NaCl, NaClO solution at a pH of 12.48, and the composition. The chemical shift scale was referenced by setting the Cl— peak to 0 ppm. NaClO solutions above a pH=7 had identical spectra with a peak at approximately 5.1 ppm. Below pH of 7.0, the ClO— peak disappeared and was replaced by much broader, less easily identifiable peaks. The composition was presented with one peak at approximately 4.7 ppm, from ClO— in the composition. This peak was integrated to estimate the concentration of ClO— in the composition, which was determined to be 2.99 ppt or 0.17 M of ClO— in the composition.

Proton NMR

An ASEA sample was prepared by adding 550 μL of ASEA and 50 μL of D2O (Cambridge Isotope Laboratories) to an NMR tube and vortexing the sample for 10 seconds. 1H NMR experiments were performed on a 700 MHz Bruker spectrometer equipped with a QNP cryogenically cooled probe. Experiments used a single pulse with presaturation on the water resonance experiment. A total of 1024 scans were taken. All experiments were performed at room temperature.

Figure 6:
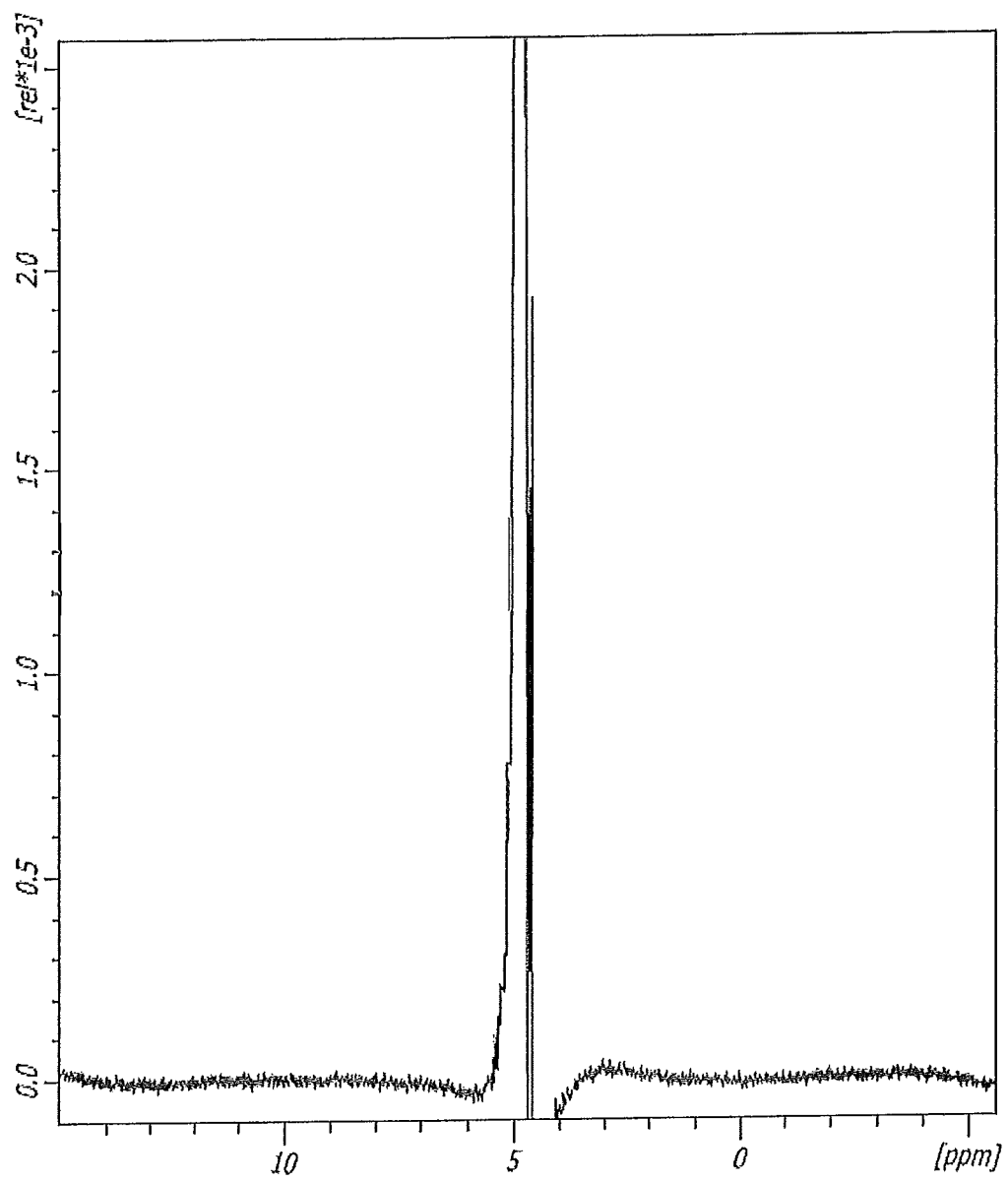
FIG. 6 illustrates a 1H NMR spectrum of a composition of the present disclosure.

A 1H NMR spectrum of the composition was determined and is presented in FIG. 6. Only peaks associated with water were able to be distinguished from this spectrum. This spectrum show that very little if any organic material can be detected in the composition using this method.

Phosphorous NMR and Mass Spectrometry

DIPPMPO (5-(Diisopropoxyphosphoryl)-5-1-pyrroline-N-oxide) (VWR) samples were prepared by measuring about 5 mg of DIPPMPO into a 2 mL centrifuge tube. This tube then had 550 μL of either the composition or water added to it, followed by 50 μL of D2O. A solution was also prepared with the composition but without DIPPMPO. These solutions were vortexed and transferred to NMR tubes for analysis. Samples for mass spectrometry analysis were prepared by dissolving about 5 mg of DIPPMPO in 600 μL of the composition and vortexing, then diluting the sample by adding 100 μL of sample and 900 μL of water to a vial and vortexing.

NMR experiments were performed using a 700 MHz Bruker spectrometer equipped with a QNP cryogenically cooled probe. Experiments performed were a single 30° pulse at a 31P frequency of 283.4 MHz. A recycle delay of 2.5 seconds and 16384 scans were used. Phosphoric acid was used as an external standard. All experiments were performed at room temperature.

Mass spectrometry experiments were performed by directly injecting the ASEA/DIPPMPO sample into a Waters/Synapt Time of Flight mass spectrometer. The sample was directly injected into the mass spectrometer, bypassing the LC, and monitored in both positive and negative ion mode.

Figure 7:
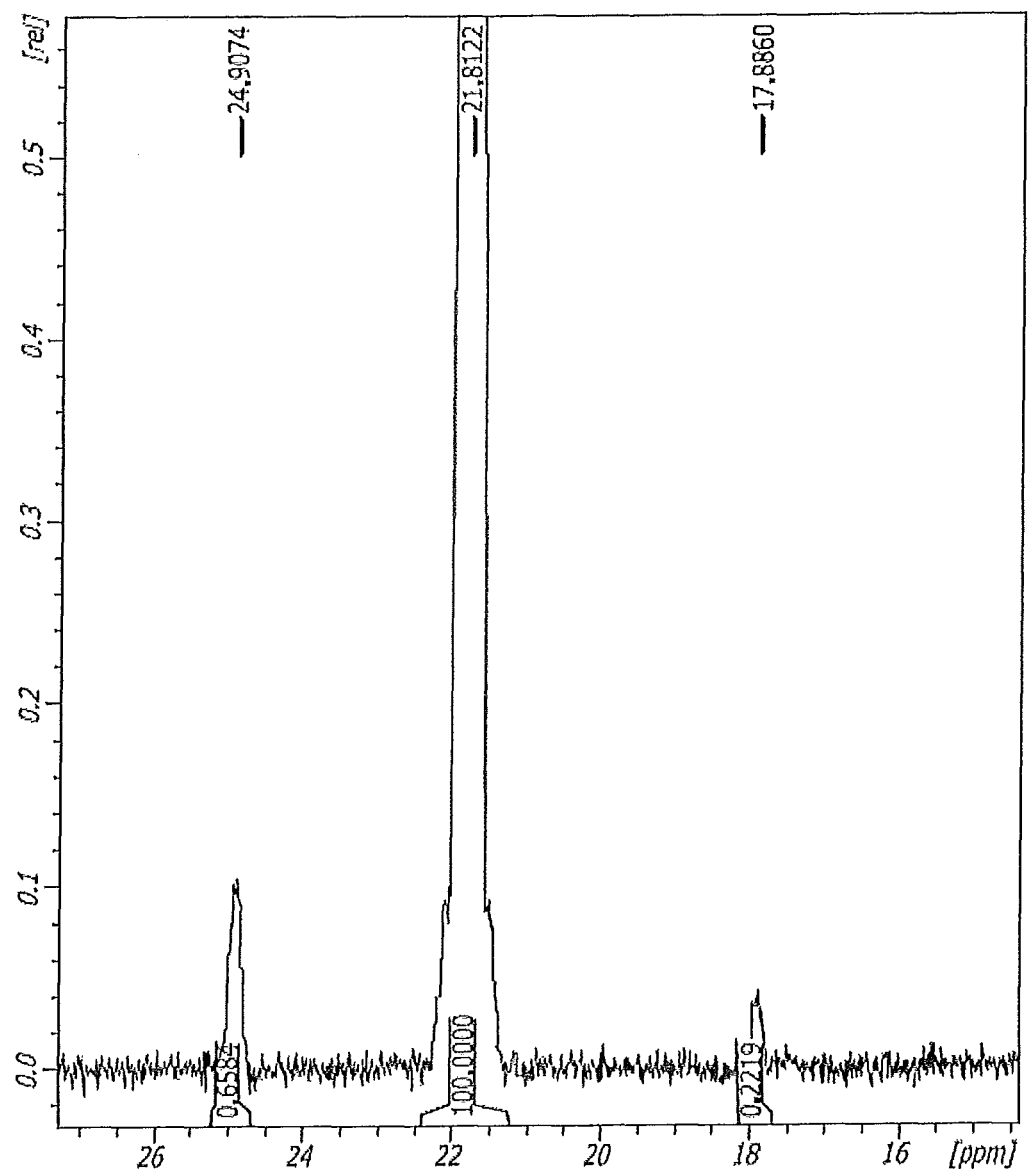
FIG. 7 illustrates a 31P NMR spectrum of DIPPMPO combined with a composition described herein.

31P NMR spectra were collected for DIPPMPO in water, the composition alone, and the composition with DIPPMPO added to it. An external reference of phosphoric acid was used as a chemical shift reference. FIG. 7 illustrates a 31P NMR spectrum of DIPPMPO combined with the composition. The peak at 21.8 ppm was determined to be DIPPMPO and is seen in both the spectrum of DIPPMPO with the composition (FIG. 7) and without the composition (not pictured). The peak at 24.9 ppm is most probably DIPPMPO/OH. as determined in other DIPPMPO studies. This peak may be seen in DIPPMPO mixtures both with and without the composition, but is detected at a much greater concentration in the solution with the composition. In the DIPPMPO mixture with the composition, there is another peak at 17.9 ppm. This peak may be from another radical species in the composition such as OOH. or possibly a different radical complex. The approximate concentrations of spin trap complexes in the composition/DIPPMPO solution are as follows:

| Solution | Concentration |
| --- | --- |
| DIPPMPO | 36.6 mM |
| DIPPMPO/OH• | 241 μM |
| DIPPMPO/radical | 94 μM |

Figure 8:
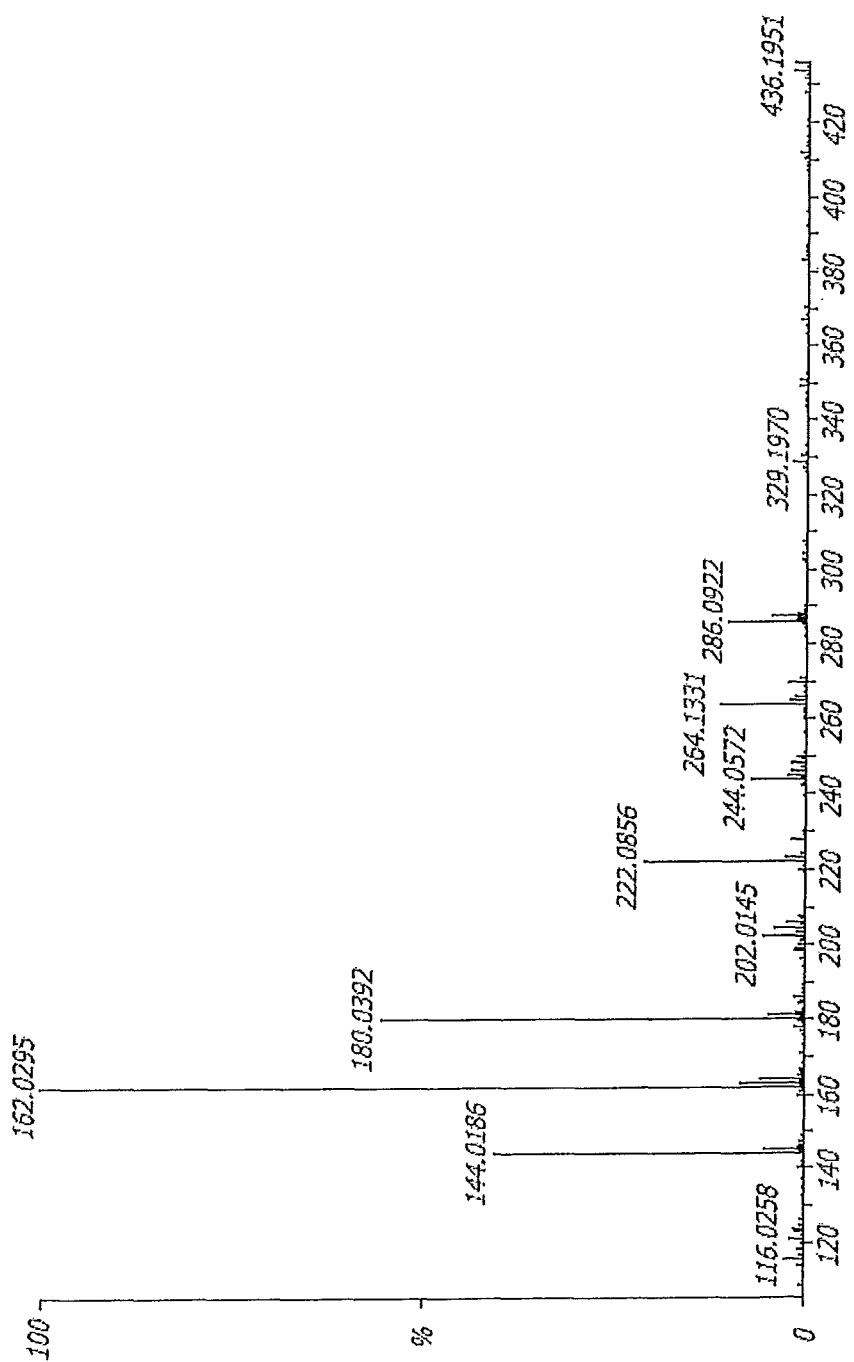
FIG. 8 illustrates a positive ion mode mass spectrum showing a parent peak and fragmentation pattern for DIPPMPO with m/z peaks at 264, 222, and 180.

Mass spectral data was collected in an attempt to determine the composition of the unidentified radical species. The mass spectrum shows a parent peak and fragmentation pattern for DIPPMPO with m/z peaks at 264, 222, and 180, as seen in FIG. 8. FIG. 8 also shows peaks for the DIPPMPO/Na adduct and subsequent fragments at 286, 244, and 202 m/z. Finally, FIG. 8 demonstrates peaks for one DIPPMPO/radical complex with m/z of 329. The negative ion mode mass spectrum also had a corresponding peak at m/z of 327. There are additional peaks at 349, 367, and 302 at a lower intensity as presented in FIG. 8. None of these peaks could be positively confirmed. However, there are possible structures that would result in these mass patterns. One possibility for the peak generated at 329 could be a structure formed from a radical combining with DIPPMPO. Possibilities of this radical species include a nitroxyl-peroxide radical (HNO—HOO.) that may have formed in the composition as a result of reaction with nitrogen from the air. Another peak at 349 could also be a result of a DIPPMPO/radical combination. Here, a possibility for the radical may be hypochlorite-peroxide (HOCl—HO.). However, the small intensity of this peak and small intensity of the corresponding peak of 347 in the negative ion mode mass spectrum indicate this could be a very low concentration impurity and not a compound present in the ASEA composition.

ICP/MS Analysis

Samples were analyzed on an Agilent 7500 series inductively-coupled plasma mass spectrometer (ICP-MS) in order to confirm the hypochlorite concentration that was determined by NMR. A stock solution of 5% sodium hypochlorite was used to prepare a series of dilutions consisting of 300 ppb, 150 ppb, 75 ppb, 37.5 ppb, 18.75 ppb, 9.375 ppb, 4.6875 ppb, 2.34375 ppb, and 1.171875 ppb in deionized Milli-Q water. These standards were used to establish a standard curve.

Based on NMR hypochlorite concentration data, a series of dilutions was prepared consisting of 164.9835 ppb, 82.49175 ppb, 41.245875 ppb, 20.622937 ppb, 10.311468 ppb, and 5.155734 ppb. These theoretical values were then compared with the values determined by ICP-MS analysis. The instrument parameters were as follows:

| | Elements analyzed $^{35}Cl$, $^{37}Cl$ |
| --- | --- |
| # of points per mass | 20 |
| # of repetitions | 5 |
| Total acquisition time | 68.8 s |
| Uptake speed | 0.50 rps |
| Uptake time | 33 s |
| Stabilization time | 40 s |
| Tune | No Gas |
| Nebulizer flow rate | 1 mL/min |
| Torch power | 1500 W |

The results of the ICP-MS analysis are as follows:

| Dilution | Measured Concentration (ppb) | Concentration by NMR (ppb) |
| --- | --- | --- |
| 1 | 81 | 82 |
| 2 | 28 | 41 |
| 3 | 24 | 21 |
| 4 | 13 | 10 |
| 5 | 8 | 5 |

Dilutions were compared graphically to the ICP-MS signals and fit to a linear equation (R2=0.9522). Assuming linear behavior of the ICP-MS signal, the concentration of hypochlorite in the composition was measured to be 3.02 ppt. Concentration values were determined by calculating the concentration of dilutions of the initial composition and estimating the initial composition hypochlorite concentration to be 3 ppt (as determined from 35Cl NMR analysis). The ICP-MS data correlate well with the 35Cl NMR data, confirming a hypochlorite concentration of roughly ⅓% (3 ppt). It should be noted that ICP-MS analysis is capable of measuring total chlorine atom concentration in solution, but not specific chlorine species. The NMR data indicate that chlorine predominantly exists as ClO— in the composition.

Gas Phase Quadrupole MS

Sample Prep

Three sample groups were prepared in triplicate for the analysis: 1) Milli-Q deionized water 2) the composition, and 3) 5% sodium hypochlorite standard solution. The vials used were 20 mL headspace vials with magnetic crimp caps (GERSTEL). A small stir bar was placed in each vial (VWR)

along with 10 mL of sample. The vials were capped, and then placed in a Branson model 5510 sonicator for one hour at 60° C.

The sonicator was set to degas which allowed for any dissolved gasses to be released from the sample into the headspace. After degassing, the samples were placed on a CTC PAL autosampler equipped with a heated agitator and headspace syringe. The agitator was set to 750 rpm and 95° C. and the syringe was set to 75° C. Each vial was placed in the agitator for 20 min prior to injection into the instrument. A headspace volume of 2.5 mL was collected from the vial and injected into the instrument.

Instrument Parameters

The instrument used was an Agilent 7890A GC system coupled to an Agilent 5975C EI/CI single quadrupole mass selective detector (MSD) set up for electron ionization. The GC oven was set to 40° C. with the front inlet and the transfer lines being set to 150° C. and 155° C. respectively. The carrier gas used was helium and it was set to a pressure of 15 PSI.

The MSD was set to single ion mode (SIM) in order to detect the following analytes:

| Analyte | Mass |
| --- | --- |
| Water | 18 |
| Nitrogen | 28 |
| Oxygen | 32 |
| Argon | 40 |
| Carbon Dioxide | 44 |
| Chlorine | 70 |
| Ozone | 48 |

The ionization source temperature was set to 230° C. and the quadrupole temperature was set to 150° C. The electron energy was set to 15 V.

Mass spectrometry data was obtained from analysis of the gas phase headspace of the water, the composition, and hypochlorite solution. The raw area counts obtained from the mass spectrometer were normalized to the area counts of nitrogen in order to eliminate any systematic instrument variation. Both nitrogen and water were used as standards because they were present in equal volumes in the vial with nitrogen occupying the headspace and water being the solvent. It was assumed that the overall volume of water and nitrogen would be the same for each sample after degassing. In order for this assumption to be correct, the ratio of nitrogen to water should be the same for each sample. A cutoff value for the percent relative standard deviation (% RSD) of 5% was used. Across all nine samples, a % RSD of 4.2 was observed. Of note, sample NaClO-3 appears to be an outlier, thus, when removed, the % RSD drops to 3.4%.

Figure 9:
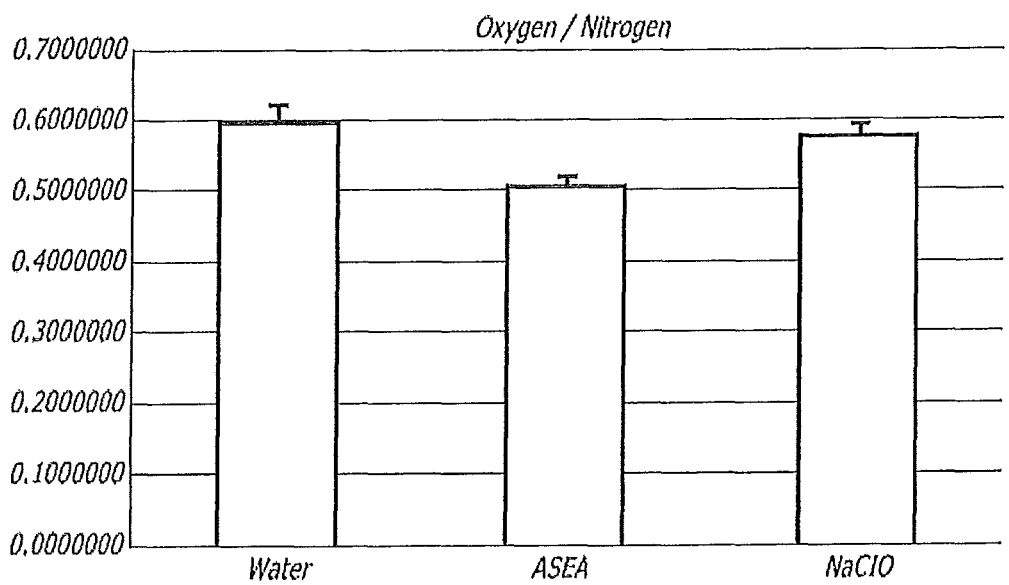
FIG. 9 illustrates oxygen/nitrogen ratios for a composition described herein compared to water and NaClO (the composition is labeled "ASEA").
Figure 10:
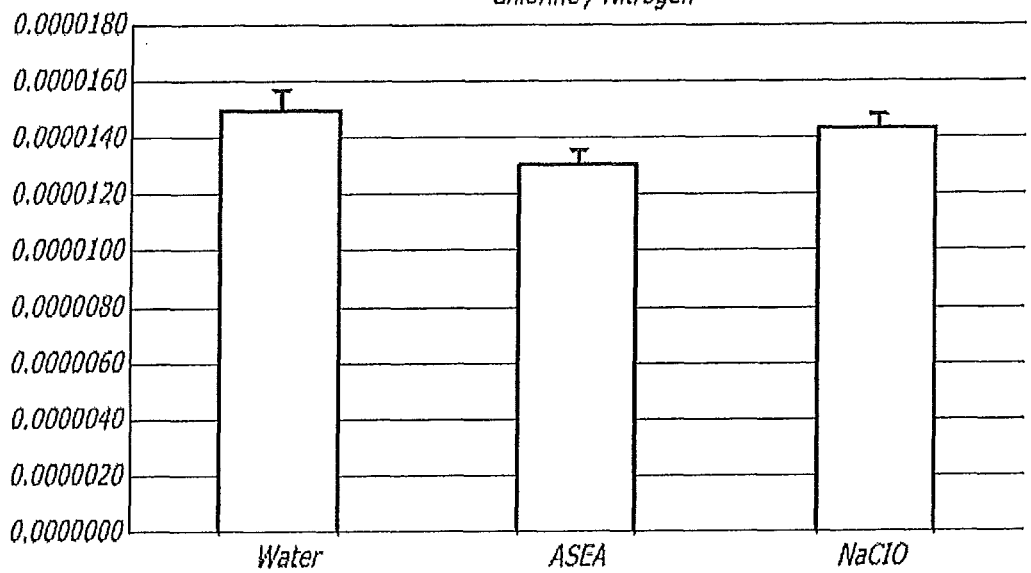
FIG. 10 illustrates chlorine/nitrogen ratios for a composition described herein compared to water and NaClO (the composition is labeled "ASEA").

FIGS. 9-11 illustrate oxygen/nitrogen, chlorine/nitrogen, and ozone/nitrogen ratios. It appears that there were less of these gases released from the composition than from either water or nitrogen. It should be noted that the signals for both ozone and chlorine were very weak. Thus, there is a possibility that these signals may be due to instrument noise and not from the target analytes.

FIG. 12 illustrates the carbon dioxide to nitrogen ratio. It appears that there may have been more carbon dioxide released from the composition than oxygen. However, it is possible that this may be due to background contamination from the atmosphere.

Based on the above, more oxygen was released from both water and sodium hypochlorite than the composition.

EPR

Two different composition samples were prepared for EPR analysis. The composition with nothing added was one sample. The other sample was prepared by adding 31 mg of DIPPMPO to 20 mL of the composition (5.9 mM), vortexing, and placing the sample in a 4° C. refrigerator overnight. Both samples were placed in a small capillary tube which was then inserted into a normal 5 mm EPR tube for analysis.

EPR experiments were performed on a Bruker EMX 10/12 EPR spectrometer. EPR experiments were performed at 9.8 GHz with a centerfield position of 3500 Gauss and a sweepwidth of 100 Gauss. A 20 mW energy pulse was used with modulation frequency of 100 kHz and modulation amplitude of 1 G. Experiments used 100 scans. All experiments were performed at room temperature.

Figure 13:
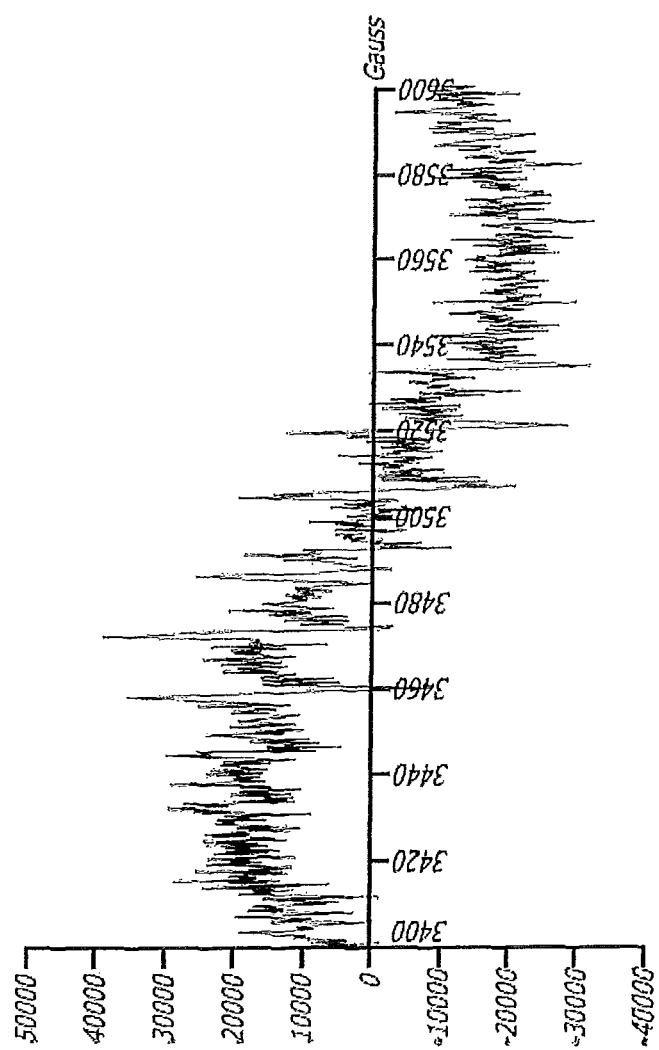
FIG. 13 illustrates an EPR splitting pattern of DIPPMOP/ASEA mixture (the composition in a certain embodiment is "ASEA").

EPR analysis was performed on the composition with and without DIPPMPO mixed into the solution. FIG. 13 shows the EPR spectrum generated from DIPPMPO mixed with the composition. The composition alone showed no EPR signal after 100 scans (not presented). FIG. 13 illustrates an EPR splitting pattern for a free electron. This electron appears to be split by three different nuclei. The data indicate that this is a characteristic splitting pattern of OH. radical interacting with DMPO (similar to DIPPMPO). This pattern can be described by 14N splitting the peak into three equal peaks and 1H three bonds away splitting that pattern into two equal triplets. If these splittings are the same, it leads to a quartet splitting where the two middle peaks are twice as large as the outer peaks. This pattern may be seen in FIG. 13 twice, with the larger peaks at 3457 and 3471 for one quartet and 3504 and 3518 for the other quartet. In this case, the 14N splitting and the 1H splitting are both roughly 14 G, similar to an OH* radical attaching to DMPO. The two quartet patterns in FIG. 13 are created by an additional splitting of 47 G. This splitting is most likely from coupling to 31P, and similar patterns have been seen previously. The EPR spectrum in FIG. 13 indicates that there is a DIPPMPO/OH. radical species in the solution.

Example 3

The electrolyzed fluid can be made in different types of vessels as long as the proper power sourced is used. One example of an apparatus that was used to make electrolyzed solution for treating fungal infections is that referred to in FIGS. 14-18.

Referring first to FIG. 14, which is a perspective view of a first presently preferred embodiment of the present invention generally represented at 100, includes a power supply 102 and a fluid receptacle represented at 104. The fluid receptacle 104 includes a base 114 upon which is attached a fluid vessel 116. The base 114 can preferably be fabricated from an insulative plastic material. The fluid vessel 116 is preferably fabricated from an inert clear plastic material which is compatible with biological processes as available in the art.

A lid 118 is provided to cover the fluid vessel 116 and keep contaminants out of the fluid vessel 116. A screen 120 is positioned to prevent foreign objects, which might accidentally fall into the fluid vessel 116, from falling to the bottom of the fluid vessel 116. The saline solution which is to be treated is placed into the fluid vessel 116, and the lid 118 placed, for the necessary period of time after which the electrolyzed saline solution can be withdrawn from the fluid vessel 116, for example into a syringe, for use. The fluid vessel 116 is sealed at its bottom by a floor 124 which is attached to the interior of the base 114.

An electrode assembly, generally represented at 122, is attached to the floor 124 so that any fluid in the fluid vessel is exposed to the electrode assembly 122. The electrode assembly 122 is electrically connected to the power supply 102 via terminals 110 and 112 and cables 106 and 108, respectively. The power supply 102 should deliver a controlled voltage and current to the electrode assembly 122 when fluid is placed into the fluid vessel 116. The voltage and current applied to the electrode assembly 122 will vary according to the fluid being electrolyzed. A control for setting and measuring the voltage 102A and a control for setting and measuring the current 102B is provided in the power supply. In accordance with the present invention, a low voltage of less than about 30 volts DC is used. Exemplary voltage and current values, and the advantages which accrue when using the preferred voltage and current values, will be explained shortly.

FIG. 15 is a top view of the electrode assembly 122 represented in FIG. 14. The electrode assembly 122 preferably comprises a cylindrical inner electrode 128 and a cylindrical outer electrode 126. The inner electrode 128 is preferably solid or any hollow in the inner electrode is sealed so that fluid does not enter any such hollow. The cylindrical shape of the inner electrode 128 and the outer electrode 126 is preferred and results in better performance than obtained with electrodes of other shapes, e.g., elongated flat panels.

The diameter A of the inner electrode 128 is preferably about one-half inch but the diameter A of the inner electrode can be selected by those skilled in the art in accordance with the particular application for the electrode using the information contained herein. The outer electrode 126 should be of a generally cylindrical shape and preferably be fabricated from titanium or niobium having a thickness (indicated at B in FIG. 15) which ensures that the inner electrode is shielded from potentially physical damage. As will be appreciated, titanium and niobium provide the advantage of resistance against corrosion which further prevents the introduction of harmful substances into the fluid being electrolyzed.

Still referring to FIG. 15, the space, indicated at C, between the inner electrode 128 and the outer electrode 126 does not exceed a maximum value. In contrast to previously available devices which separate the electrodes by greater distances and then utilize higher voltages to obtain the desired electrolyzation, the present invention keeps the electrode spacing small and obtains improved performance over other schemes. It is preferred that the space between the inner electrode 128 and the outer electrode 126 be not more than about one-half (½) inch; it is more preferred that the space between the inner electrode 128 and the outer electrode 126 be not more than about three-eights (⅜) inch; and, it is most preferred that the space between the inner electrode 128 and the outer electrode 126 be not more than about one-quarter (¼) inch.

Reference will next be made to FIG. 15A which is a side cross sectional view of the electrode assembly taken along line 3-3 in FIG. 15. As seen in FIG. 15A, the outer electrode 126 extends above the inner electrode 128 to provide improved electrical performance and physical protection. The outer electrode 126 is attached to the floor 124 by way of bolts 130, which extend through bores provided in the floor 124, and accompanying nuts. An electrical connection is made to the outer electrode 126 by a lead 136 attached to the bolt and nut. The lead 136 is attached to one of the terminals 110 or 112. Similarly, an electrical connection is made to the inner electrode 128 by a lead 134 which is held in place by a nut attached to a threaded stud extending from the bottom of the inner electrode and through a bore provided in the floor 124. The lead 134 is attached to the remaining one of the terminals 110 or 112. The leads 134 and 136 are kept insulated from any fluid which is present in the fluid vessel 116.

It is preferred that the inner electrode 128 function as the anode while the outer electrode function as the cathode when electrolyzing fluids and the power supply 102 and the terminals 110 and 112 should be properly arranged to carry this out.

It is recognized in the art that the anode is subject to destructive forces during electrolysis. In the prior art, the anode of an electrode assembly may dissolve to the point of being inoperative and may need to be replaced very often. Critically, as the anode of an electrode assembly dissolves, the metallic components of the anode are dispersed into the fluid. If the fluid is a saline solution which will be used to treat physiological fluids, toxic substances dispersed into the solution, such as the materials comprising the anode, may be harmful or dangerous to the person who expects to be benefitted from the treatment.

Of all the possible materials for fabrication of the anode, the art recognizes that platinum is the least likely to be dissolved when used as an anode. Unfortunately, the cost of platinum precludes the use of an anode which consists entirely of platinum. Thus, it is common in the art to utilize another metal as a base for the anode with a layer of platinum being placed on surfaces which contact the fluid to be electrolyzed.

The present invention advantageously utilizes an inner electrode 128, i.e., an anode, which includes a base of titanium, and even more preferably niobium (also known as columbium), upon which a layer of platinum is provided wherever fluid contacts the anode. Significantly, niobium is a relatively good electrical conductor having a conductivity which is about three times greater than the conductivity of titanium. Moreover, if the base metal is exposed to the fluid, such as if a pinhole defect develops, toxic products are not produced by the contact between niobium and the fluid. Moreover, the high breakdown voltage in saline solution of the oxide which forms when a niobium base receives a layer of platinum provides further advantages of the present invention.

Upon a base of niobium, a layer of platinum is formed on the anode. The layer of platinum is preferably formed using a technique referred to in the art as brush electrodeposition which can be carried out by those skilled in the art using the information set forth herein. Other techniques can also be used to form the platinum layer, such as tank (immersion) electrodeposition, vapor deposition, and roll bonding, but brush electrodeposition is preferred because of its superior adhesion and resulting less porosity than other economically comparable techniques.

The thickness of the platinum layer is preferably greater than about 0.02 mils and is most preferably greater than about 0.06 mils, and up to about 0.20 mils. The combination of using niobium as a base for the anode of the electrode assembly and utilizing brush electrodeposition provides that the platinum layer can be much thinner than otherwise possible and still provide economical and reliable operation. It will be appreciated by those skilled in the art, that even with an anode fabricated in accordance with the present invention replacement of the anode, which preferably comprises the inner electrode 128 represented in FIG. 15A, may be necessary after a period of use. The construction of the embodiments of the present invention facilitate replacement of the inner electrode 128 and the outer electrode 126 when it becomes necessary.

Represented in FIG. 16 is a block diagram of a second presently preferred embodiment, generally represented at 150, of the present invention. The embodiment represented in FIG. 16 is particularly adapted for treating large quantities of saline solution. Represented in FIG. 16 is a tank 152 in which the saline solution is electrolyzed. An electrode assembly 154 is provided in the tank and is preferably immersed into the solution. A power supply 158, capable of providing sufficient current at the proper voltage, is connected to the electrode assembly via a cable 160.

Also represented in FIG. 16 is a circulation device 156 which optionally functions to circulate the solution within the tank 152. A sensor 162 is also optionally provided to measure the progress of the electrolyzation of the solution in the tank 152, for example by measuring the pH of the solution. The sensor may preferably be an ion selective electrode which can be chosen from those available in the art. Other sensors, for example chlorine, ozone, and temperature sensors, may also be included within the scope of the present invention. A control unit 164 is optionally provided to coordinate the operation of the power supply 158, the circulation device 156, and the sensor 162 in order to obtain the most efficient operation of the apparatus 150.

It will be appreciated that devices such as power supply 158, circulation device 158, sensor 162, and control unit 164 can be readily obtained from sources in the industry and adapted for use with embodiments of the present invention by those skilled in the art using the information contained herein. In particular, the control unit 164 is preferably a digital microprocessor based device accompanied by appropriate interfaces all allowing for accurate control of the operation of the apparatus 150. It is also within the scope of the present invention to include structures to prevent contamination of the treated solution by contact with nonsterile surfaces and by airborne pathogens both during treatment and while the fluid is being transferred to the apparatus and being withdrawn from the apparatus.

Figure 17:
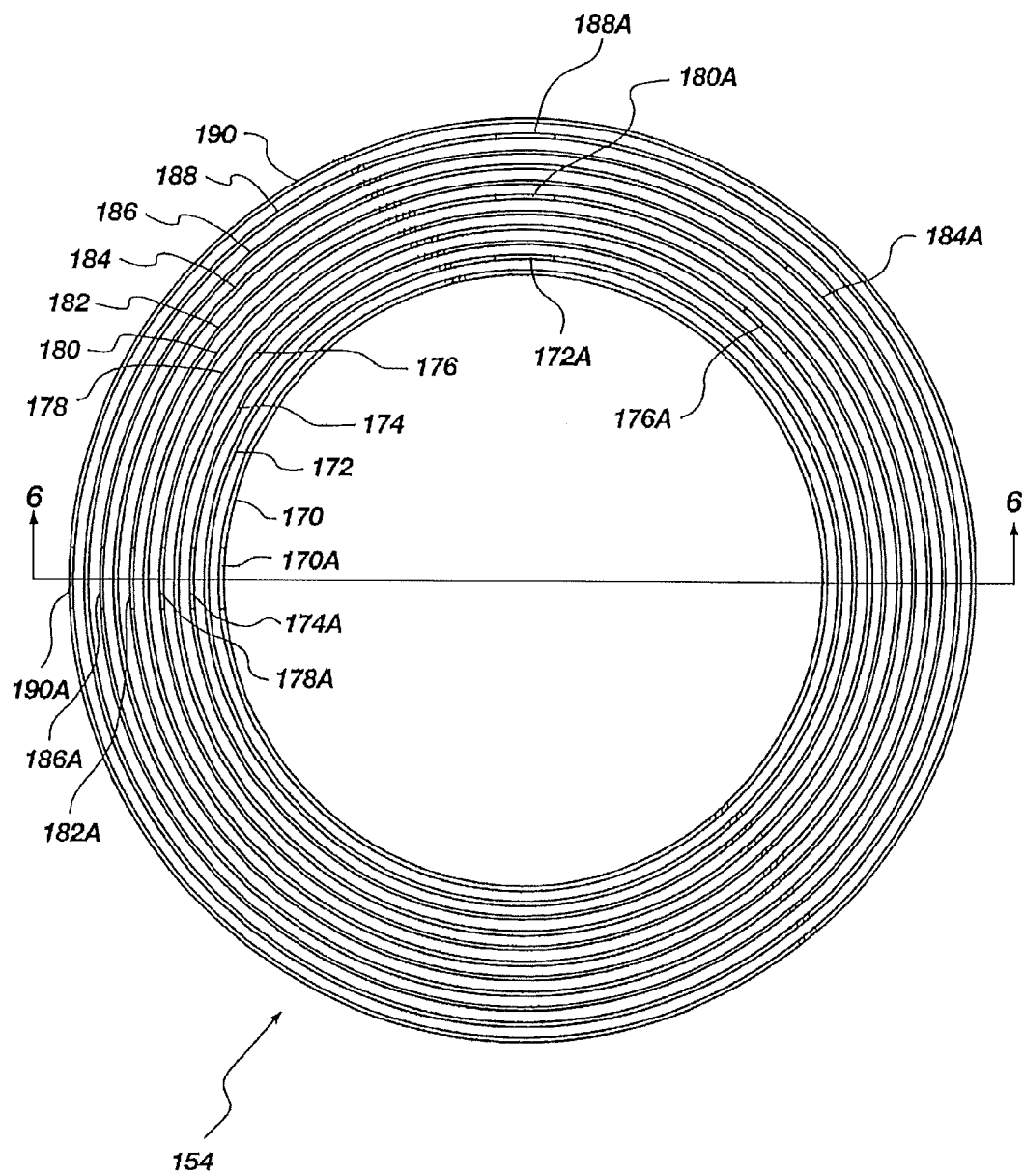
FIG. 17 is a top view of an electrode assembly preferred for use in the apparatus represented in FIG. 16.
Figure 18:
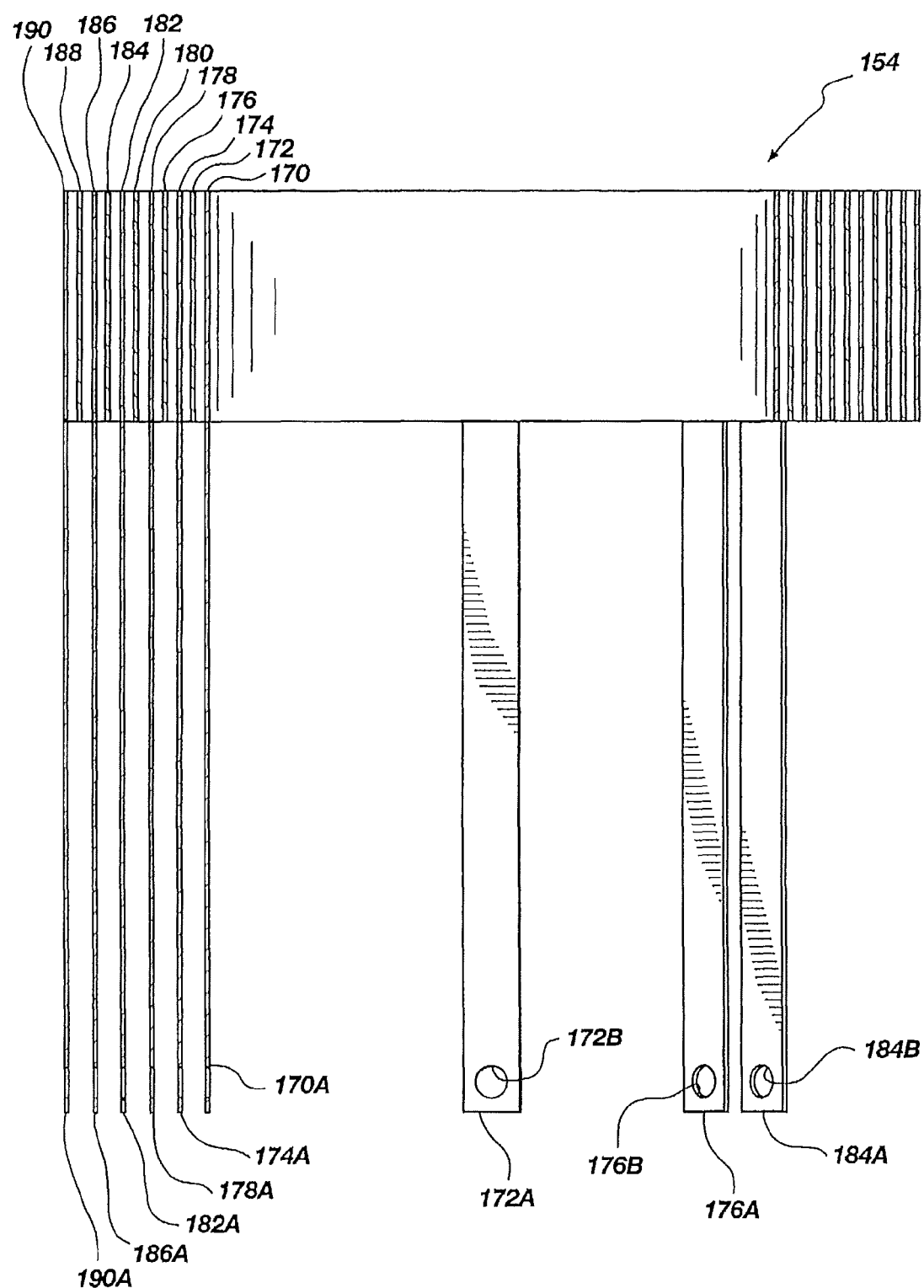
FIG. 18 is a cross sectional view taken along line 6-6 of FIG. 17.

Reference will next be made to FIGS. 17 and 18 which are a top view and cross sectional view, respectively, of an electrode assembly, generally represented at 154, which is preferred for use in the apparatus represented in FIG. 16. As can be seen best in FIG. 17, the electrode assembly 154 includes a plurality of concentrically arranged anodes and cathodes. The cylindrical shape and concentric arrangement of the electrodes represented in FIG. 17 provides for the most efficient operation. The number of electrodes which are included can be selected according to the application of the apparatus. For example, the number of electrodes may be six, seven, eight, the eleven represented in FIGS. 17 and 18, or more.

In FIG. 17, electrodes 170, 174, 178, 182, 186, and 190 preferably function as cathodes and are preferably fabricated in accordance with the principles set forth above in connection with the outer electrode represented at 126 in FIGS. 14-15A. Furthermore, in FIG. 17 electrodes 172, 176, 180, 184, and 188 function as anodes and are preferably fabricated in accordance with the principles set forth above in connection with the inner electrode represented at 128 in FIGS. 14-15A.

In the cross sectional side view of FIG. 18 a plurality of tabs extend from the cylindrical electrodes 170, 172, 174, 176, 178, 180, 182, 184, 186, and 190 to facilitate making an electrical connection thereto. Provided below in the following Table are the relationship between the tabs illustrated in FIG. 18 and the electrodes.

| Relationship between the tabs illustrated in FIG. 18 | | |
|---|---|---|
| Electrode | Tab | Function |
| 170 | 170A | Cathode |
| 172 | 172A | Anode |
| 174 | 174A | Cathode |
| 176 | 176A | Anode |
| 178 | 178A | Cathode |
| 180 | 180A (Not illustrated in FIG. 18) | Anode |
| 182 | 182A | Cathode |
| 184 | 184A | Anode |
| 186 | 186A | Cathode |
| 188 | 188A | Anode |
| 190 | 190A (Not illustrated in FIG. 18) | Cathode |

Using the tabs 170A, 172A, 174A, 176A, 178A, 180A, 182A, 184A, 186A, 188A, and 190A, those skilled in the art can provide the necessary electrical connections to the electrodes 170, 172, 174, 176, 178, 180, 182, 184, 186, and 190 and can also provide numerous structures to prevent contact between the tabs and the fluid to be treated. Each of the tabs illustrated in FIG. 18 are provided with an aperture, such as those represented at 172B, 176B, and 184B, which receive a wiring connector.

While the apparatus described in Example 3 herein has many uses, the most preferred use of the apparatus described herein is subjecting sterile saline solution to electrolysis. The electrolyzed saline solution can then be used to treat a patient. The saline solution preferably has an initial concentration in the range from about 0.25% to about 1.0% NaCl which is about one-fourth to full strength of normal or isotonic saline solution. According to Taber's Cyclopedic Medical Dictionary, E. A. Davis, Co. 1985 Ed., an "isotonic saline" is defined as a 0.16 M NaCl solution or one containing approximately 0.95% NaCl; a "physiological salt solution" is defined as a sterile solution containing 0.85% NaCl and is considered isotonic to body fluids and a "normal saline solution;" a 0.9% NaCl solution which is considered isotonic to the body. Therefore, the terms "isotonic," "normal saline," "balanced saline," or "physiological fluid" are considered to be a saline solution containing in the range from about 0.85% to about 0.95% NaCl. Moreover, in accordance with the present invention, a saline solution may be subjected to electrolysis at concentrations in the range from about 0.15% to about 1.0%.

It is preferred that one of the above described saline solutions be diluted with sterile distilled water to the desired concentration, preferably in the range from about 0.15% to about 0.35% prior to treatment in accordance with the present invention. This dilute saline solution is subjected to electrolysis using the embodiments of the present invention at a voltage, current, and time to produce an appropriately electrolyzed solution as will be described shortly. It is presently preferred to carry out the electrolysis reaction at ambient temperatures. In a more preferred embodiment the saline solution used with the apparatus of Example 3 is 9.1 gNaCl/1 L of water. In another preferred embodiment the saline solution used with the apparatus of Example 3 is 2.8 gNaCl/1 L of water.

The voltage and current values provided herein are merely exemplary and the voltage and current values which are used, and the time the saline solution is subject to electrolysis, is determined by many variables, e.g., the surface area and efficiency of the particular electrode assembly and the volume and/or concentration of saline solution being electrolyzed. For electrode assemblies having a different surface area, greater volumes of saline solution, or higher concentrations of saline solutions the voltage, current, or time may be higher and/or longer than those exemplary values provided herein. In accordance with the present invention, it is the generation of the desired concentration of ozone and active chlorine species which is important. Electrolyzation of the saline solution also results in other products of the electrolysis reaction including members selected from the group consisting of hydrogen, sodium and hydroxide ions. It will be appreciated that the interaction of the electrolysis products results in a solution containing bioactive atoms, radicals or ions selected from the group consisting of chlorine, ozone, hydroxide, hypochlorous acid, hypochlorite, peroxide, oxygen and perhaps others along with corresponding amounts of molecular hydrogen and sodium and hydrogen ions.

In order to arrive at the preferred end product, electrolyzed saline solution using the apparatus illustrated in FIGS. 14-15A, about a 0.33% (about one third physiologically normal) saline solution is placed in the fluid vessel 116 (FIG. 14) and the apparatus is operated for about 5 to 15 minutes with a voltage between the electrodes being maintained in the range from about 10 volts to about 20 volts with a current flow maintained in the range from about 5 to about 20 amps.

In one example, the cell described in Example 3 operated for 1 hour at 40 C using 3 Amps with a saline solution of less than 0.35% saline.

In one example, the cell described in Example 3 operated for 1 hour at 40 C using 3 Amps with a saline solution of less than 1.0% saline.

In one example, the cell described in Example 3 operated for 3 minutes at 23 C using 3 Amps with a saline solution of less than 0.35% saline.

In one example, the cell described in Example 3 operated for 3 minutes at 23 C using 3 Amps with a saline solution of less than 1.0% saline.

As one example of the use of the embodiment of FIGS. 14-15A, a 0.225% saline solution is subjected to a current of 3 amperes at 20 volts (DC) for a period of three minutes. A 17 ml portion of this electrolyzed solution is aseptically diluted with 3 mls of a sterile 5% saline resulting in a finished isotonic electrolyzed saline having an active ozone content of 12.+−0.2 mg/L and an active chlorine species content of 60.+−0.4 ppm at a pH of 7.4.

It will be appreciated that the low voltages used in accordance with the present invention are preferably not greater than forty (40) volts DC or an equivalent value if other than direct current is used. More preferably, the voltages used in accordance with the present invention is not more than about thirty (30) volts DC. The use of low voltages avoids the problem of production of undesirable products in the fluid which can result when higher voltages are used. In accordance with the present invention, the close spacing of the electrodes facilitates the use of low voltages.

In another example, to show that the embodiment of FIGS. 14-15 can be used to effectively carry out electrolysis in saline solutions up to about 1% in concentration, the electrolysis reaction is carried out at saline concentrations of 0.3, 0.6 and 0.9%, respectively. The active chlorine species $Cl_2$ and ozone $O_3$ contents were measured and are provided in the table below:

| $Cl_2$ and $O_3$ Content from Salines at Varying Concentrations | | |
|---|---|---|
| Saline Concentration (% NaCl) | $Cl_2$ Concentration (ppm) | $O_3$ Concentration (mg/mL) |
| 0.3 | 129 | 21.8 |
| 0.6 | 161 | 26.6 |
| 0.9 | 168 | 28.0 |

As can be seen from the above table, the resulting electrolyzed saline solution includes active components which are within the parameters required for effective treatment.

It will be appreciated that the features of the present invention, including the close electrode spacing, the low voltages used, and the materials used to fabricate the electrodes, result in an apparatus which provides unexpectedly better results than the previously available devices and schemes.

Example 4

A saline solution was made with the apparatus of Example 3 wherein the solution was electrolyzed for 3 min at 3 amps and such that the solution being electrolyzed had 9.1 g NaCl/L of purified water. The product made accordingly is called RXN-1. The RXN-1 product was tested for superoxides and hypochlorites as described herein. Specifically, the presence of superoxides was tested with the Nanodrop 3300 and R-phycoerytherin (R-PE) as the reagent and the presence of hypochlorites was tested with the Nanodrop 3300 and aminophenyl fluorescein (APF) as the reagent. The tests revealed the presence of both superoxides as well as hypochlorites. The superoxides were tested as an amount relative to the amount of superoxides that are present in a sample made according to Example 1. That is, superoxides were tested as an amount relative to the amount of superoxides when a total of 1,000 gallons of salinated water was electrolyzed with a total of 56 amps running through the electrodes and further wherein the electrolyzing occurred at 4.5-5.8° C. The amount of superoxides present in the RXN-1 product was 130% of the amount of superoxides present in a sample made according to Example 1. Similarly, the hypochlorites were tested as an amount relative to the amount of hypochlorites that are present in a sample made according to Example 1. That is, hypochlorites were tested as an amount relative to the amount of hypochlorites when a total of 1,000 gallons of salinated water was electrolyzed with a total of 56 amps running through the electrodes and further wherein the electrolyzing occurred at 4.5-5.8° C. The amount of hypochlorites present in the RXN-1 product was 82% of the amount of hypochlorites present in a sample made according to Example 1.

Example 5

A saline solution was made with the apparatus of Example 3 wherein the solution was electrolyzed for 3 min at 3 amps and such that the solution being electrolyzed had 2.8 g NaCl/L of purified water. The product made accordingly is called RXN-2. The RXN-2 product was tested for superoxides and hypochlorites as described herein. Specifically, the presence of superoxides was tested with the Nanodrop 3300 and R-phycoerytherin (R-PE) as the reagent and the presence of hypochlorites was tested with the Nanodrop 3300 and aminophenyl fluorescein (APF) as the reagent. The tests revealed the presence of both superoxides as well as hypochlorites. The superoxides were tested as an amount relative to the amount of superoxides that are present in a sample made according to Example 1. That is, superoxides were tested as an amount relative to the amount of superoxides when a total of 1,000 gallons of salinated water was electrolyzed with a total of 56 amps running through the electrodes and further wherein the electrolyzing occurred at 4.5-5.8° C. The amount of superoxides present in the RXN-2 product was 120% of the amount of superoxides present in a sample made according to Example 1. Similarly, the hypochlorites were tested as an amount relative to the amount of hypochlorites that are present in a sample made according to Example 1. That is, hypochlorites were tested as an amount relative to the amount of hypochlorites when a total of 1,000 gallons of salinated water was electrolyzed with a total of 56 amps running through the electrodes and further wherein the electrolyzing occurred at 4.5-5.8° C. The amount of hypochlorites present in the RXN-2 product was 80% of the amount of hypochlorites present in a sample made according to Example 1.

Power Sources

As described in detail above, a DC (direct current) is used to electrolyze water. To prepare a direct current for electrolyzation, readily available electricity, such as that which comes from a wall socket, is brought to a terminal strip. This terminal strip, also known as a terminal block, acts like a surge protector allowing a number of electrical connections from the strip to other devices. For example, the terminal strip can be an interface for electrical circuits. The terminal strip can be connected to a ground and/or a current transformer. A transformer can be used to measure electric currents. The terminal strip can also be connected to a potentiometer. The potentiometer measures voltage across an electrical system and can be used to aid in adjusting the voltage. For example a dial can be connected to the potentiometer so that the operator may adjust the voltage as desired.

Another transformer can be connected to the potentiometer, which can then be operably connected to a rectifier. Rectifiers in general convert alternating current (AC) to direct current (DC). One specific type of rectifier which suits the invention well is a bridge rectifier. Converting the waveform into one with a constant polarity increases the voltage output. This waveform is called a full wave rectified signal. Once the waveform and voltage are configured as desired, the DC shunt can provide a means for bringing electricity to different devices such as the electrodes, monitors and other operational instruments.

Figure 19:
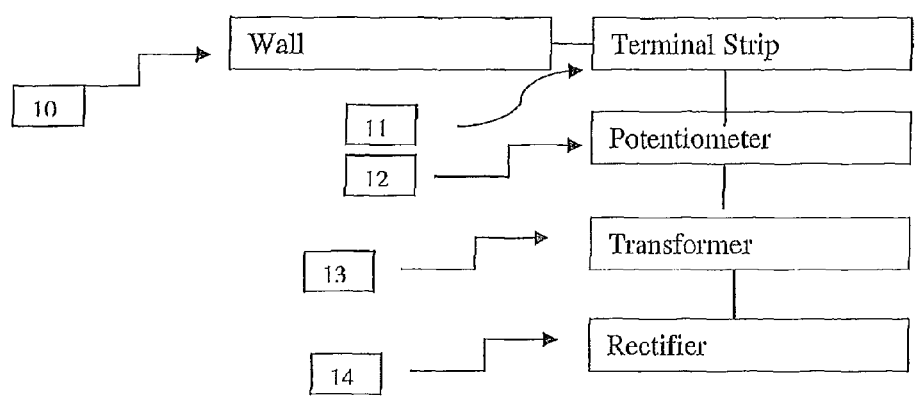
FIG. 19 Illustrates a block diagram of a power source.

FIG. 19 diagrams an example of a power source which can be used in the invention. Electricity comes in from the wall 10 and is met by a terminal strip 11. Terminal strip 11 is in operable communication with a potentiometer 12, and a current transformer 13. Potentiometer 12 is in operable communication with the transformer 13. The transformer 13 is in operable communication with a rectifier 14.

Figure 20:
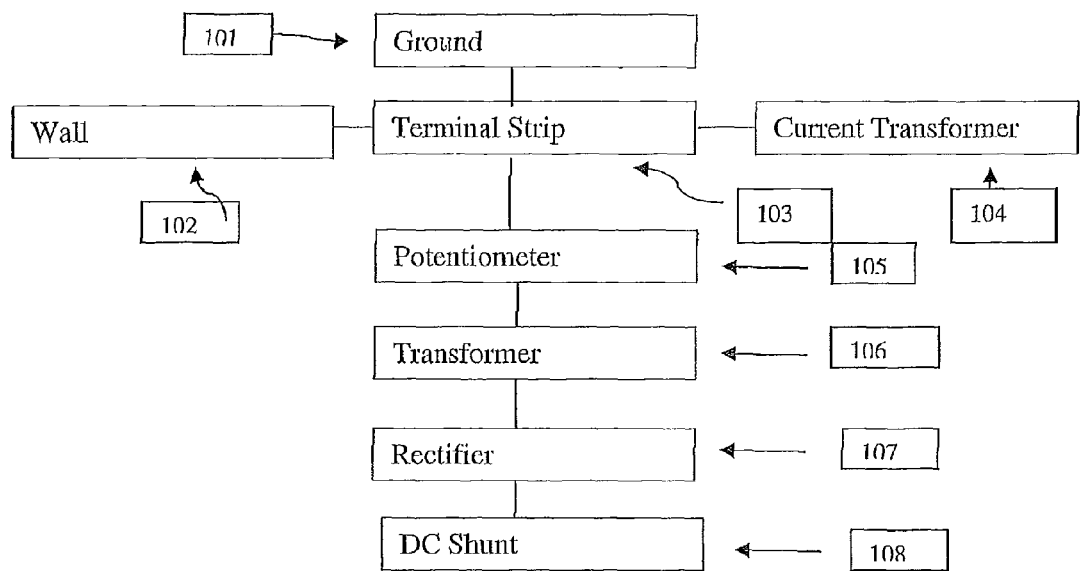
FIG. 20 Illustrates a block diagram of another power source.
Figure 21:
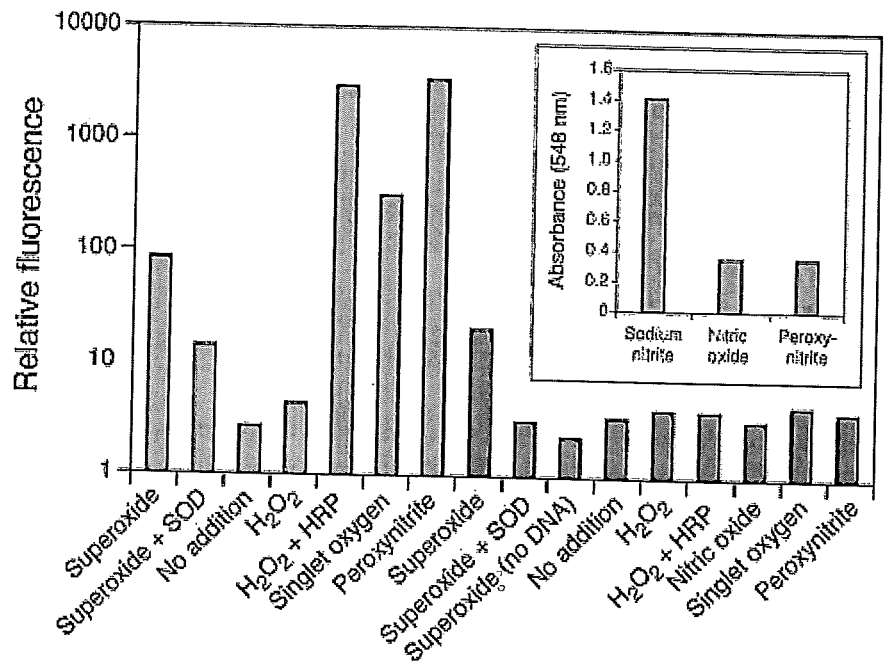
FIG. 21 is a chart of the relative fluorescence of various compositions.

FIG. 20 diagrams an example of a power source which can be used in the invention. Electricity comes in from the wall 102 and is met by a terminal strip 103. Terminal strip 103 is in operable communication with a potentiometer 105, a grounding means 101 and a current transformer 104. Potentiometer 105 is in operable communication with the transformer 106. The transformer 106 is in operable communication with a rectifier 107. Rectifier 107 is in operable communication with a DC shunt 108.

Determination of ROS Levels Against a Known Standard

The measurement of concentrations of ROS, particularly a superoxide, inside the solutions has been done by means of a fluoro spectrometer, Nanodrop 3300, and three varieties of fluorescent dyes, R-Phycoerytherin (R-PE), Hydroxyphenyl fluorescein (HPF) and Aminophenyl fluorescein (APF), that are commonly used to determine relative ROS concentrations inside active biological systems and cells. The molecules in these dyes change shape, and therefore fluoresce only when exposed to molecular components in ROS. The resulting change in fluorescence can then be detected by the fluoro spectrometer and can be related to the concentration of ROS present. ROS concentrations in electrolyzed saline solutions (ESS) solutions are verified and detected by either APF or R-PE fluorescent dyes, both of which produce entirely consistent measurements of relative concentrations of ROS in various concentrations and dilutions of ESS solutions. ROS measurements in ESS solutions have been linked using R-PE fluorescent dye, to the reaction of this dye to regulated concentrations of 2/2'-Axobis(2-methylpropionamide)dihidrochloride, a molecule that produces known amounts of ROS. This is not an absolute measurement, but it relates ROS in ESS to amounts of a known producer of ROS.

These fluorescent dyes are often used in combination with a fluorescence microscope to create high-resolution images of the build-up of ROS (oxidative stress) inside individual living cells. These dyes have been shown to specifically be sensitive to concentrations of ROS regardless of complex surrounding chemical environments.

Although APF and R-PE dyes are capable of measuring relative ROS concentrations in ESS solutions, no known absolute standard concentration for stabilized ROS in pure saline solutions exists. Furthermore, discrepancies in the decay time of these fluorescent dyes make measuring standardized amounts of ROS in other solutions incompatible with measuring those found in ESS. This may be due, in part, to the molecular complexes in ESS solutions that keep the ROS concentration stable, effectively shielding the free radicals from readily reacting with the dyes. The standard for ROS concentration in ESS solutions is therefore measured relative to the ROS concentration in a standardized solution that has been used in all of the antimicrobial and toxicity studies to date, both published and unpublished. Methods to measure absolute ROS concentrations in ESS solutions are actively being pursued.

The regulated amounts of ROS, thus measured, inside a variety of the ESS solutions produced by various embodiments of this invention have been shown to be stable, consistent and predictable, sufficient for therapeutic applications.

The development of a phycobiliprotein fluorescence quenching assay for the routine determination of ROS content in ASEA has been successful and is used routinely to monitor production quality for ROS levels. The assay has the following characteristics: ease of use, sensitivity, and quantitation. The assay is linear over a 2 log 10 range of ROS concentrations. For a compositions comprising RXNs, the starting saline was used as a negative control, AAPH (2,2'-Azobis(2-amidinopropane)dihydrochloride which is a standard ROS generating compound) served as a positive control and allowed the generation of a standard curve, and the compositions comprising RXNs or other samples comprised the unknowns.

Figure 24:
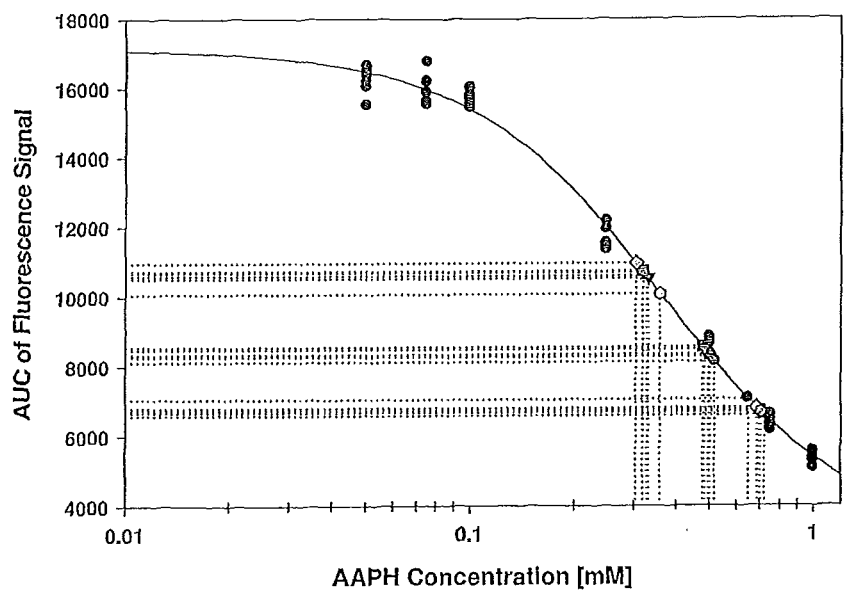
FIG. 24 is a graph of the Expt. 5f07 ROS Assay.

For the purposes of this work, we determined the oxygen radical content of our health benefiting product. In the assay described below, R-Phycoerythrin [an algal protein] is exposed to varying levels of a standard ROS generating compound [AAPH] wherein the level of fluorescence quenching is logarithmically related to ROS content. This provides a standard curve from which to estimate the ROS content of unknown samples. The levels of ROS in the unknown samples are expressed as mM equivalents of AAPH. FIG. 24 shows the concentration of AAPH.

Materials and Methods:

PHYCOERYTHRIN and R-PHYCOERYTHRIN: were purchased from Sigma Chemical Corporation, St. Louis, Mo.

AAPH: 2,2'-azobis(2-amidino-propane)dihydrochloride was purchased from Wako Chemicals USA, Richmond, Va. This compound generates ROS upon contact with water.

FLUORESCENCE READER: an 8 or 16 place fluorescence reader manufactured by Pacific Technologies, Redmond, Wash. was used to detect the fluorescence signal from the phycoerythrins. Temperature was controlled at 37 C during a 12-20 hr. experimental run. The samples were interrogated every 0.5 to 2 min where each sample interrogation was comprised of 1024 lamp flashes from a LED whose emission spectra was appropriate from the excitation spectra of R-Phycoerythrin. Proper cut-off filters were employed to detect the fluorescence emissions of the phycoerythrins.

DATA ANALYSES: All data is captured in real time. The data contained in the worksheet can be manipulated to determine the relative change of fluorescence over the time course of the experiment and subsequently, SigmaPlot Pro v. 7 software [SPSS Software, Chicago, Ill.] is used to determine the area under the curve. Area under the curve [AUC] analysis is appropriate since Cao, Cao et al. Comparison of different analytical methods for assessing total antioxidant capacity of human serum. Clinical Chemistry June 1998 vol. 44 no. 6 1309-1315 which is hereby incorporated by reference in its entirety, and colleagues have demonstrated that in this method both the inhibition time and degree of inhibition of fluorescence by free radicals are considered. The area under the curve [AUC] are plotted against the log 10 mM AAPH concentration to provide a standard curve from which to estimate the levels of ROS in unknown samples.

Detailed Methods:

Step a. 300 uL of phosphate buffer, pH 7.0, 100 mM is added to ½" glass vials.

Step b. 15 ug of R-Phycoerythrin in 15 uL of phosphate buffer is added to the materials in Step a. The vials are capped and placed into the wells of the fluorescence reader for 15 min prior to the addition of a saline control, ASEA or AAPH solutions. During this period, fluorescence values are collected from which to calculate a 100% value. This value is then used in subsequent calculations to determine a relative fluorescence signal value for the standard curves.

1 mg of AAPH is added to 1 ml of phosphate buffer and 10-fold dilutions are made to provide at least a 3 log 10 range of AAPH concentrations. Similarly, ASEA solutions are diluted and added to appropriate vials in Step b.

100 uL of the materials in Step a are added to the appropriate vials in Step b. The vials are mixed and replaced into the reader for up to an additional 12 to 20 hrs of evaluation.

RESULTS: As shown in FIG. 24, as the concentration of AAPH decreased from 1.00 mM to 0.050 mM, there was as concomitant increase in the normalized AUC. Buffer control [not shown] revealed that over time there is a spontaneous loss of fluorescence signal, although this loss represents only ~8% of the original signal.

Figure 25:
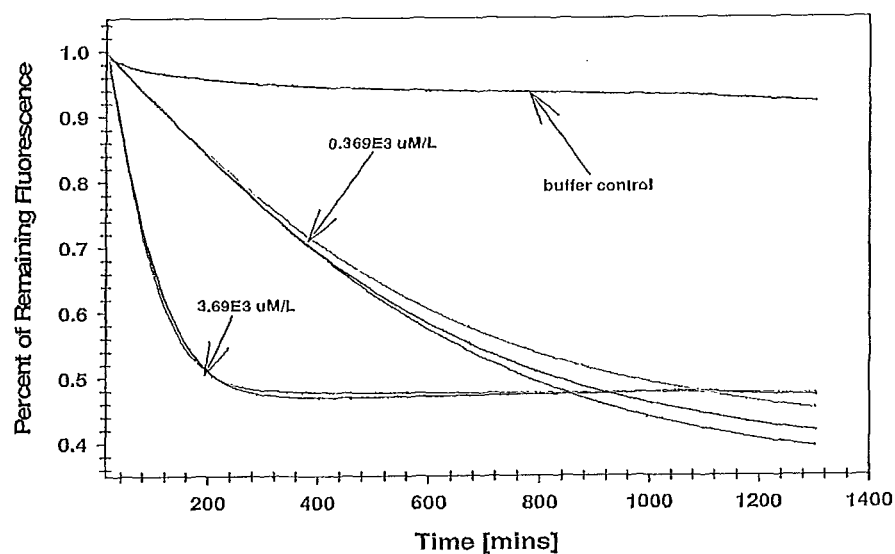
FIG. 25 is a graph of an Intraassay Variation Using Two Levels of AAPH.

The data represented in FIG. 25 shows intra-assay variability of two concentrations of AAPH. Using SigmaStat v 2.01 software, the following mean, Std Deviation and Relative Std Deviation were calculated and are presented in Table 1. The data shows that the variation for each concentration the variation among replicates ranged from ~0.1% to 4% variation [Rel. Std. Dev.]. These data suggest that fluorescence quenching assay is capable of producing small variations among triplicate or quadruplicate samples over a 10-fold range of AAPH concentrations.

TABLE 1

Intraassay Variability

| AAPH Concentration | N | Mean AUC | Std. Dev. | Std. Error | % Rel. Std. Dev. |
|---|---|---|---|---|---|
| 3.69 mM | 3 | 653 | 1.07 | 0.62 | 0.15 |
| 0.369 mM | 4 | 804 | 31.7 | 15.0 | 3.7 |

Table 2 shows the results of the analyses of ASEA solutions prepared by MDI and filtered through 0.2 u Supor membrane to ensure sterility prior to clinical application. It is clear that the ASEA from different production lots are similar in their ROS content. Statistical analysis supported this observation [p=0.272]. The most important point is the observation that filtration through a 0.2 u Supor membrane does not decrease the ROS content of ASEA.

Table 2. ROS Content of ASEA Filtered and Unfiltered Through 0.2 Supor Membrane

TABLE 2

| Treatment | N | Mean AUC | Std. Dev. | Std. Error | % Rel. Std. Dev. |
|---|---|---|---|---|---|
| Unfiltered | 4 | 589.7 | 65.8 | 32.9 | 5.5 |
| Filtered | 4 | 646.3 | 66.3 | 33.1 | 5.1 |

The levels of variance [Rel. Std. Dev.] reported by us is similar to that reported by Cao and colleagues.

In Table 3, data from a typical analysis is illustrated. Saline [negative control] always contained less than 0.1 mM AAPH equivalents of ROS whereas ASEA always contained >1.0 mM ROS.

TABLE 3

ROS Content of ASEA and Saline

| ASEA or Saline Samples | Mean AUC | ROS Content mM AAPH equivalents |
|---|---|---|
| ASEA | 479 | 3.3 |
| ASEA | 543 | 2.2 |
| ASEA | 441 | 4.5 |
| ASEA | 523 | 2.98 |
| ASEA | 516 | 3.2 |
| Saline | 974 | 0.095 |
| Saline | 956 | 0.075 |

The above shows a known concentration of a standard, AAPH, as 653 and 804 when tested at 3.69 mM and 0.369 mM respectively. A compositions comprising RXNs showed a AUC of between 441-543.

The measurement of concentrations of ROS inside the solutions can be done by means of a fluorospectrometer, Nanodrop 3300, and three varieties of fluorescent dyes, R-Phycoerytherin (R-PE), Hydroxyphenyl fluorescein (HPF) and Aminophenyl fluorescein (APF), all of which are commonly used to determine relative ROS concentrations inside active biological systems and cells. The molecules in these dyes change shape, and therefore fluoresce only when exposed to molecular components in ROS. The resulting change in fluorescence can then be detected by the fluorospectrometer and can be related to the concentration of ROS present. ROS concentrations in a compositions comprising RXNs can be verified and detected by either APF or R-PE fluorescent dyes, both of which produce entirely consistent measurements of relative concentrations of ROS in various concentrations and dilutions of RXNs. The ROS measurements in a compositions comprising RXNs have been linked, using R-PE fluorescent dye, to the reaction of this dye to regulated concentrations of 2/2'-Axobis(2-methylpropionamide)dihidrochloride, a molecule that produces known amounts of ROS.

Superoxide Testing

Superoxides were tested with the NanoDrop 3300 and R-PE as the reagent for the three samples.

The intensity of the fluorescence indicates the amount of ROS in the sample. This dye, R-PE, is toxic, expensive, must be kept refrigerated, degrades in strong blue light, such as a fluorescent bulb, and is time sensitive. The following steps were taken:

The ND-3300 software was called up, the "Other Fluorophores" button was clicked and the "R-PE 50 uM Activated" option was selected.

The ND-3300 was blanked: 2 uL (1 drop) of deionized water was placed using a pipette on the measurement pedestal and the arm was carefully closed. The "Blank" button was clicked and the ND-3300 took a "blank" measurement, thereby calibrating the ND-3300.

The samples were prepared by pipetting 10 ml deionized water into each one of the large (15 ml) test tubes required for the test. One test tube will be required for each sample to be tested.

The test tubes were labeled by cutting out squares of sticky-back label stock, large enough to fit over the mouth of the test tubes, and by writing the number "1", "2" and "3" on the label. The labels were placed covering the mouth of the test tubes to both identify them and to keep the liquids from evaporating.

10 ul of the R-PE fluorescent dye was apportioned into each of the test tubes by following these steps: turning off the lights, taking the previously prepared R-PE dye test tube out of the refrigerator [this test tube was previously prepared by putting 2 ul of the concentrate from the commercial R-PE vial inside 5 ml deionized water (a phosphate buffer is not needed)]. The prepared test tube was placed in the rack with the others. This dye is toxic and is sensitive to light so these steps should be done quickly, with lab coat, gloves and goggles. With a clean pipette, 10 ul of the prepared R-PE dye was add into each of the test tubes. The R-PE was placed back in the test tube back in the refrigerator.

The test tubes were mixed well using a mixing pipette which was place into each of the test tubes, 2-3 ml were drawn out and then quickly pushed back in, allowing some bubbles to escape to better agitate the contents of the test tubes. This was repeated three to four times for each tube. At this point, it is necessary to have separate mixing pipette heads for each tube. The test tubes were allowed to sit for least 30 min. after mixing.

The initial pre-sample measurements were taken on all of the test tubes: The ND-3300 was blanked using the procedures outlined above. A folded Kimwipe was used to blot the last sample droplet off the lower and upper pedestals before loading a new drop to be analyzed. A descriptive name for the sample was typed into the Sample ID field in the software. 2 ul of test tube #1 was loaded onto the pedestal, the arm was carefully closed and the "measure" button pressed. Three measurements were taken of the sample in test tube #1. This procedure was repeated for the next two samples. Specifically, the Sample ID field was changed to reflect the descriptive name of the sample in the second test tube. And then three (3) measurements were taken from the second test tube also. This step was done until all test tubes were analyzed. When R-PE was activated, the RFU readings shown were between the 100 and 2000.

A compositions comprising RXNs was added to the test tubes: This procedure was carefully timed. The R-PE dye is only accurate for less than 30 minutes after activation and therefore all measurements must be acquired after the same amount of exposure time. 10 ul of a compositions comprising RXNs sample #1 was added to test tube #1 and immediately thereafter a timer was set for three (3) minutes. Then the test tube #1 was mixed with a pipette. This step was repeated for all three samples.

At 6 hrs post addition of the first a compositions comprising RXNs sample to a test tube, measurements were taken from every test tube in the following manner. The ND-3300 was blanked, the pedestals were blotted and the "Sample ID" for test tube #1 was typed in. After three (3) minutes, using a sampling pipette, a 2 ul drop was taken from test tube #1 and place it on the pedestal and the measure button was pressed. This process was repeated until all of the test tubes were measured.

The data was cleaned up by pressing the "Show Report" button so that all of the data that has been taken so far was displayed. The data was then saved and analyzed.

Hypochlorite Testing

Hypochlorites were tested with the NanoDrop 3300 Fluorospectrometer and APF as the reagent.

The ND-3300 software was called up, the "Other Fluorophores" button was clicked and the "APF 50 uM Activated" option was selected.

The ND-3300 was blanked: 2 uL (1 drop) of deionized water was placed using a pipette on the measurement pedestal and the arm was carefully closed. The "Blank" button was clicked and the ND-3300 took a "blank" measurement, thereby calibrating the ND-3300.

The samples were prepared by pipetting 10 ml deionized water into each one of the large (15 ml) test tubes required for the test. One test tube will be required for each sample to be tested.

The test tubes were labeled by cutting out squares of sticky-back label stock, large enough to fit over the mouth of the test tubes, and by writing the number "1", "2" and "3" on the label. The labels were placed covering the mouth of the test tubes to both identify them and to keep the liquids from evaporating.

10 ul of the APF fluorescent dye was apportioned into each of the test tubes by following these steps: turning off the lights, taking the previously prepared APF dye test tube out of the refrigerator [this test tube was previously prepared by putting 2 ul of the concentrate from the commercial APF vial inside 5 ml deionized water (a phosphate buffer is not needed)]. The prepared test tube was placed in the rack with the others. This dye is toxic and is sensitive to light so these steps should be done quickly, with lab coat, gloves and goggles. With a clean pipette, 10 ul of the prepared APF dye was add into each of the test tubes. The APF was placed back in the test tube back in the refrigerator.

The test tubes were mixed well using a mixing pipette which was place into each of the test tubes, 2-3 ml were drawn out and then quickly pushed back in, allowing some bubbles to escape to better agitate the contents of the test tubes. This was repeated three to four times for each tube. At this point, it is necessary to have separate mixing pipette heads for each tube. The test tubes were allowed to sit for least 30 min. after mixing.

The initial pre-sample measurements were taken on all of the test tubes: The ND-3300 was blanked using the procedures outlined above. A folded Kimwipe was used to blot the last sample droplet off the lower and upper pedestals before loading a new drop to be analyzed. A descriptive name for the sample was typed into the Sample ID field in the software. 2 ul of test tube #1 was loaded onto the pedestal, the arm was carefully closed and the "measure" button pressed. Three measurements were taken of the sample in test tube #1. This procedure was repeated for the next two samples. Specifically, the Sample ID field was changed to reflect the descriptive name of the sample in the second test tube. And then three (3) measurements were taken from the second test tube also. This step was done until all test tubes were analyzed. When APF was activated, the RFU readings shown were between the 100 and 2000.

A compositions comprising RXNs was added to the test tubes: This procedure was carefully timed. The APF dye is only accurate for less than 30 minutes after activation and therefore all measurements must be acquired after the same amount of exposure time. 10 ul of a compositions comprising RXNs sample #1 was added to test tube #1 and immediately thereafter a timer was set for three (3) minutes. Then the test tube #1 was mixed with a pipette. This step was repeated for all three samples.

At 30 min. post addition of the first a compositions comprising RXNs sample to a test tube, measurements were taken from every test tube in the following manner. The ND-3300 was blanked, the pedestals were blotted and the "Sample ID" for test tube #1 was typed in. After three (3) minutes, using a sampling pipette, a 2 ul drop was taken from test tube #1 and place it on the pedestal and the measure button was pressed. This process was repeated until all of the test tubes were measured.

Packaging

The packaging process includes any type of packaging that does not contribute to the decay of the superoxides, hydroxyl radicals and OOH* (for example, containers should not contain metal oxides or ions). Pouches and bottles are preferred for ease of portability and acceptability in the market. However, any suitable packaging is applicable. Containers/packaging can be made of for example glass, polyethylene, polypropylene and the like. Specific examples include Bapolene HD2035, which is a high density polyethylene copolymer and Jade brand CZ-302 polyester. Table 4 shows the relative percentage of superoxides remaining after a 12 month period when the composition is packaged in a polyethylene bottle.

Example 6

The rate of decay for superoxides, from a sample made according to Example 1, was tested over a 12 month period. That is, superoxides present in a sample made when a total of 1,000 gallons of salinated water is electrolyzed with a total of 56 amps running through the electrodes and further wherein the electrolyzing occurred at 4.5-5.8° C., according to Example 1, were tested for their relative amounts over a period of 12 months relative to a standard RFU control.

TABLE 4

1 Year Studies - shows a 3%/month decay rate over a 12 month period

| Sample ID | RFU | RFU Average per sample | RFU minus control | Standard deviation | % error | % Potency/ Stability as compared to reference sample |
|---|---|---|---|---|---|---|
| RFU Control | 1743.7 | 1759.033 | | | | |
| Control | 1814.6 | | | | | |
| Control | 1718.8 | | | | | |
| Sample 1 | 985.6 | 986.1667 | 872.8667 | 6.169549 | 0.706815 | 1 |
| Sample 1 | 980.3 | | | | | |
| Sample 1 | 992.6 | | | | | |
| Sample 2 | 1044.8 | 1003.6 | 855.4333 | 35.68151 | 4.171162 | Baseline |
| Sample 2 | 982.7 | | | | | |
| Sample 2 | 983.3 | | | | | |
| Sample 3 | 981.7 | 988.3 | 870.7333 | 16.23915 | 1.864997 | 1.007618 |
| Sample 3 | 1006.8 | | | | | |
| Sample 3 | 976.4 | | | | | |
| Sample 4 | 1132.9 | 1121.133 | 737.9 | 12.56437 | 1.70272 | 0.853903 |
| Sample 4 | 1107.9 | | | | | |
| Sample 4 | 1122.6 | | | | | |
| Sample 5 | 1189.9 | 1182.2 | 676.8333 | 19.99475 | 2.954161 | 0.783236 |
| Sample 5 | 1197.2 | | | | | |
| Sample 5 | 1159.5 | | | | | |
| Sample 6 | 1269.3 | 1256.267 | 602.7667 | 26.47647 | 4.39249 | 0.697526 |
| Sample 6 | 1225.8 | | | | | |
| Sample 6 | 1273.7 | | | | | |

Figure 22:
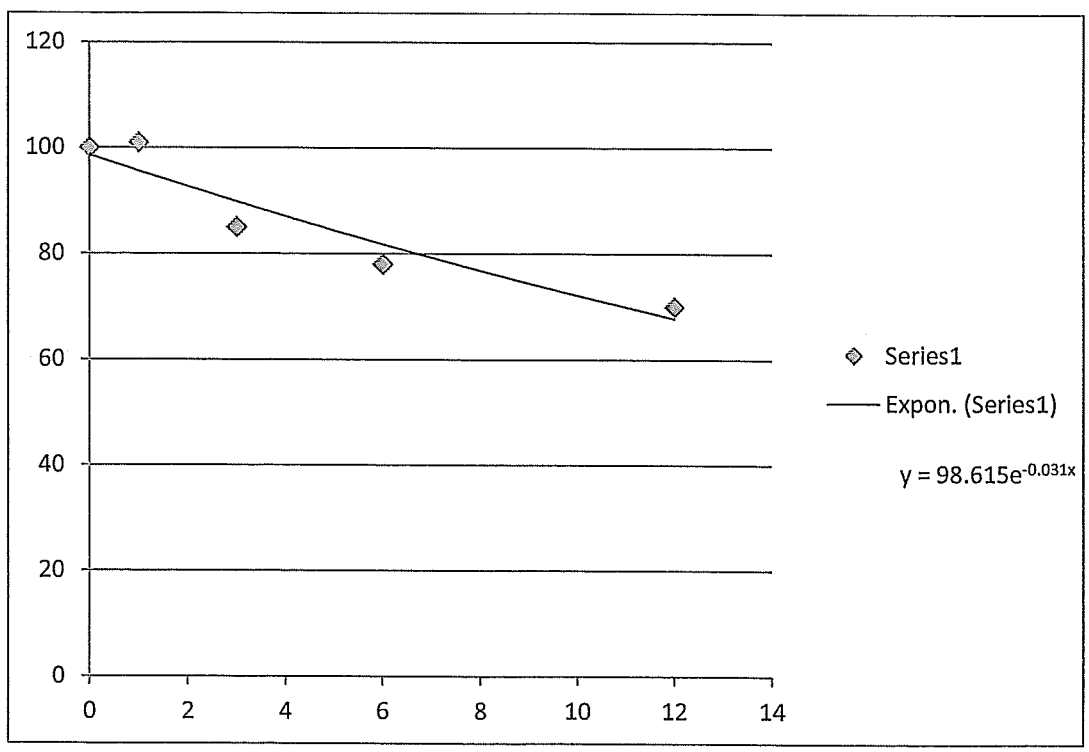
FIG. 22 is a graph of the decay rate of superoxide over a period of 1 year.

Table 4 provides data for the RFU control, Sample 1 which is a reference sample and Samples 2-6 which were taken at 1 month, 3 months, 6 months and 12 months respectively. Table 4A shows the results as a percentage of remaining superoxides at 0, 1, 3, 6 and 12 months. This Table 4 is graphically represented in FIG. 22.

TABLE 4A

| Month | % Potency/Stability |
|---|---|
| 0 | 100 |
| 1 | 101 |

TABLE 4A-continued

| Month | % Potency/Stability |
|---|---|
| 3 | 85 |
| 6 | 78 |
| 12 | 70 |

Example 7

Table 5 shows the relative percentage of superoxides remaining after a 13 month period when the composition is packaged in a polyethylene bottle and polyethylene pouch. In this Example, the composition tested was made according to the process of Example 6.

TABLE 5

13 Month Pouch v. Bottle

| Sample ID | RFU | RFU Average per sample | Standard deviation | % error | RFU minus control | % Potency/ Stability as compared to reference sample |
|---|---|---|---|---|---|---|
| Control | 1687.9 | | | | | |
| 555 | 946.4 | 940.7667 | 9.157693 | 0.973429 | 1325.273 | 1 |
| 555 | 930.2 | | | | 1370.007 | |
| 555 | 945.7 | | | | | |
| 555-1 | 817.5 | 851.3 | 29.27781 | 3.439188 | 1414.74 | 1.067508 |
| 555-1 | 867.6 | | | | | |
| 555-1 | 868.8 | | | | | |
| 525b | 967.2 | 966.0333 | 10.3992 | 1.076484 | 1300.007 | 0.948905 |
| 525b | 955.1 | | | | | |
| 525b | 975.8 | | | | | |
| 524p | 983.1 | 975.7333 | 17.08576 | 1.751069 | 1290.307 | 0.941825 |
| 524p | 956.2 | | | | | |
| 524p | 987.9 | | | | | |
| 480 | 985.9 | 1006.333 | 19.12337 | 1.900302 | 1259.707 | 0.919489 |
| 480 | 1009.3 | | | | | |
| 480 | 1023.8 | | | | | |
| 479p | 1115.2 | 1153.5 | 45.22975 | 3.921088 | 1112.54 | 0.812069 |
| 479p | 1141.9 | | | | | |
| 479p | 1203.4 | | | | | |
| 408p | 1454.2 | 1501.633 | 62.98812 | 4.194641 | 764.4067 | 0.557958 |
| 408p | 1573.1 | | | | | |
| 408p | 1477.6 | | | | | |
| 347p | 1309.4 | 1327.833 | 39.24364 | 2.955464 | 938.2067 | 0.684819 |
| 347p | 1301.2 | | | | | |
| 347p | 1372.9 | | | | | |
| 347p | 1338.1 | | | | | |
| 314 | 1354.4 | 1348.567 | 16.82627 | 1.247715 | 917.4733 | 0.669685 |
| 314 | 1361.7 | | | | | |
| 314 | 1329.6 | | | | | |
| 313p | 1459.3 | 1444.033 | 13.25908 | 0.918198 | 822.0067 | 0.600002 |
| 313p | 1435.4 | | | | | |
| 313p | 1437.4 | | | | | |

Figure 23:
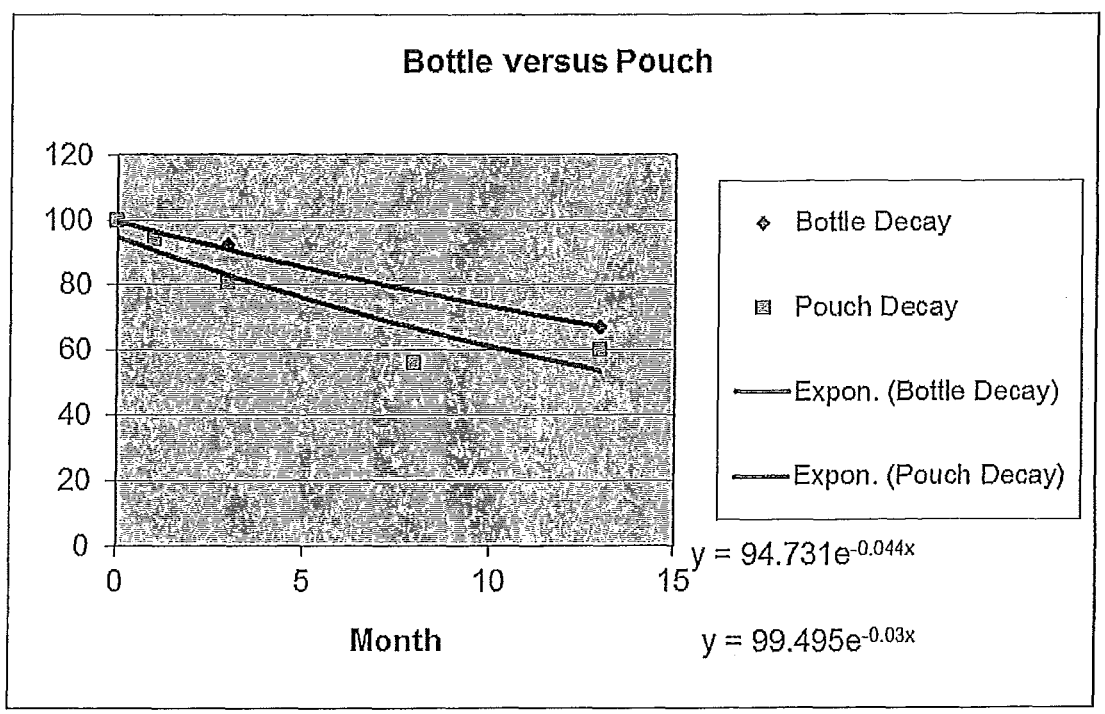
FIG. 23 is a graph showing the comparison of the decay rates of superoxide when the mixture is stored in a bottle and when the mixture is stored in a pouch.

The above graph shows a 4.4% decay rate of the superoxide radical for the pouch and a 3% decay rate for the bottle over a 13 month period. Sample 555 is a reference sample, Sample 555-1 is a baseline sample, Sample 525b is a sample taken from a bottle after 1 month, Sample 524p is a sample taken from a pouch after 1 month, Sample 480 is a Sample taken from a bottle after 3 months, Sample 479p is a sample taken from a pouch after 3 months, Sample 408p is a sample taken from a pouch after 8 months, Sample 374p is a sample taken from a pouch after 11 months, Sample 314 is a sample taken from a bottle after 13 months and Sample 313p is a sample taken from a pouch after 13 months. Table 5A is a chart showing the percentage of remaining superoxides at 0, 1, 3, 8, 11 and 13 months in a bottle and a pouch type container. This Table 5 is graphically represented in FIG. 23.

TABLE 5A

| Month | % Potency/Stability | % Potency/Stability |
|---|---|---|
| 0 | 100 | 100 |
| 1 | 95 | 94 |
| 3 | 92 | 81 |
| 8 | | 56 |
| 11 | | 68 |
| 13 | 67 | 60 |

Example 8

Borosilicate glass, such as those sold under the trade names of Kimax, Pyrex, Endural, Schott, or Refinex for example, are useful for packaging of a compositions comprising RXNs.

The presence of superoxides in a compositions comprising RXNs samples were tested after being stored in borosilicate glass bottles. The samples were made according to the process described in Example 6. Sample 397 had been stored for 24 months and Sample 512 had been stored for 20 months. Reference batch 1256 was made the same day as the test was run on all three samples. The Results are shown in Table 6.

TABLE 6

Glass Bottle ASEA Stability

| Sample | RFU | average RFU | Control − average + control loss | % Potency/ Stability as compared to reference sample |
|---|---|---|---|---|
| 397 | 780.5 | 806.8 | 1193.2 | 93.1169 |
|  | 819.5 |  |  |  |
|  | 820.4 |  |  |  |
| 512 | 676.7 | 682.4666667 | 1317.533333 | 102.8198 |
|  | 682.6 |  |  |  |
|  | 688.1 |  |  |  |
| Reference sample 1256 | 754.8 | 718.6 | 1281.4 | 100 |
|  | 707.2 |  |  |  |
|  | 693.8 |  |  |  |
| Control | 1850 |  |  |  |
| Control after 6 hours | 1700 |  |  |  |

It can be seen from the Tables that the relative concentrations of superoxides do not appreciably degrade while in the borosilicate bottles. Sample 397 had a decayed about 5% and sample 512 had 0% decay. Therefore, the yearly decay of product is no more than about 2.5% decay per year. This gives an estimated half-life of the superoxides at about 24 years.

The stability of any component in the composition can be measured by the amount of the particular composition which remains detectable after a certain amount of time. For example, if the superoxides measured had a decay rate of about 7% over a two year period, this would mean that the stability over the 2 year period was about 93%. In other words, after a two year period, about 93% of the original amount of superoxides, were still present and measured in the composition.

Example 9

Two 1 L 0.9% NaCl solutions were made and three 0.28% 1 L NaCl solutions were made from 0.28% distilled NaCl solutions. Salinity was analyzed with an EC300 conductivity meter and salt was added until the desired salinity (9 g/L or 0.9%) was reached. Samples were then mixed and placed in the freezer. 0.28% samples were collected directly from the saline storage tanks. Salinity was confirmed at 2.8 g/L (or 0.28%) by the EC300 conductivity meter. Samples were placed in the freezer.

Samples were removed from the freezer when the temperature read at 5.5° C. and placed in the fridge. One of the 2.8 g/L sample was run at 3 amps for 3 min at 5.8° C. to rinse the 1 L cell, after which the samples in the following table were run similar to the process of Example 3.

| Sample | Salinity (g/L) | Amps | Time (min) | Temp (C.) |
|---|---|---|---|---|
| 1 | 2.8 g/L | 3 | 3 | 5.8 |
| 2 | 2.8 g/L | 3 | 3 | 5.8 |
| 3 | 9 g/L | 3 | 3 | 5.6 |
| 4 | 9 g/L | 3 | 3 | 4.9 |

Free Chlorine, R-PE, APF and pH were measured for the 0.28 and 0.9% samples and the results were as shown in the following table.

| Sample/NaCl % | Free Chlorine | R-PE | APF | pH |
|---|---|---|---|---|
| 1/0.28% | 31 ppm | 112% | 112% | 7.6 |
| 3/0.9% | 76 ppm | 123% | 35% | 8.3 |
| 2/0.28% |  | 112% | 108% |  |
| 4/0.9% |  | 125% | 48% |  |

*Free Cl was tested using glass cells for 1 in the LR and 3 was measured in plastic cells in the HR.

Example 10

A Composition Made According to Example 1

KI Titration with $Na_2S_2O_3$

A titration was set up to determine the amount of ClO in a composition made according to Example 1 (for this Example 10a composition made according to Example 1 is referred to RXN1) by reacting ClO in RXN 1 with KI and acid to make I2 and Cl—. The I2 is brown in color and becomes clear upon complete reaction with S2O3- and 2I-.

The reagents are KI 42 mM with Glacial acetic acid solution (KIGAA), RXN1 and 0.100 M $Na_2S_2O_3$ solution. The 42 mM KI solution was prepared by adding 1.758 g of KI and 5 mL of GAA to a 250 mL Erlenmeyer flask and bringing the volume to 250 mL with DI H2O. 0.100M $Na_2S_2O_3$ solution was created by adding 2.482 g of $Na_2S_2O_3$ to a 100 mL volumetric flask, then adding DI H2O until 100 mL was reached. RXN1 was taken from batch 1371. Three tests were performed.

TEST 1: 50 mL of RXN1 was added to 50 mL KIGAA and mixed. The buret was rinsed three times with DI H2O then rinsed with $Na_2S_2O_3$ and filled with $Na_2S_2O_3$ to 4 mL. Initial buret reading started at 6 mL and ended at 5.69 mL. A total of 0.31 mL was added to complete the titration. Results indicate about 16 ppm of ClO (3.1×10-4M ClO).

TEST 2: 75 mL RXN1 was added to a 50 mL KIGAA and allowed to mix. Initial buret reading was 14 mL and final was about 13.55. A total of 0.45 mL was added. Results indicate about 16 ppm of ClO (3×10-4M ClO).

TEST 3: 100 mL RXN1 was added to 50 mL KIGAA. Initial buret reading was at 15 mL and the final reading was at about 14.37 mL. Approximately 0.63 mL was added in total. Results indicate about 16 ppm of ClO (3.15×10-4M ClO).

CONCLUSION: After three Tests it appears that the ClO concentration of RXN1 is close to 3.1×10-4M. This corresponds to about 16 ppm which is close to what the colorimeter read on a sample from another batch (batch 1371, which tested at 20 ppm).

Example 11

The AccuTOF-GCv 4G is a highly sensitive (S/N>100 at OFN 1 pg/µL) time-of-flight Gas Chromatography Mass Spectrometer. High resolution and mass accuracy allow for rapid elemental composition determination and target compound identification. To test for water clusters in a composition of the present invention, the composition was run in the MS and injection temperatures were lowered to the point where water clusters were detectable.

Figure 26:
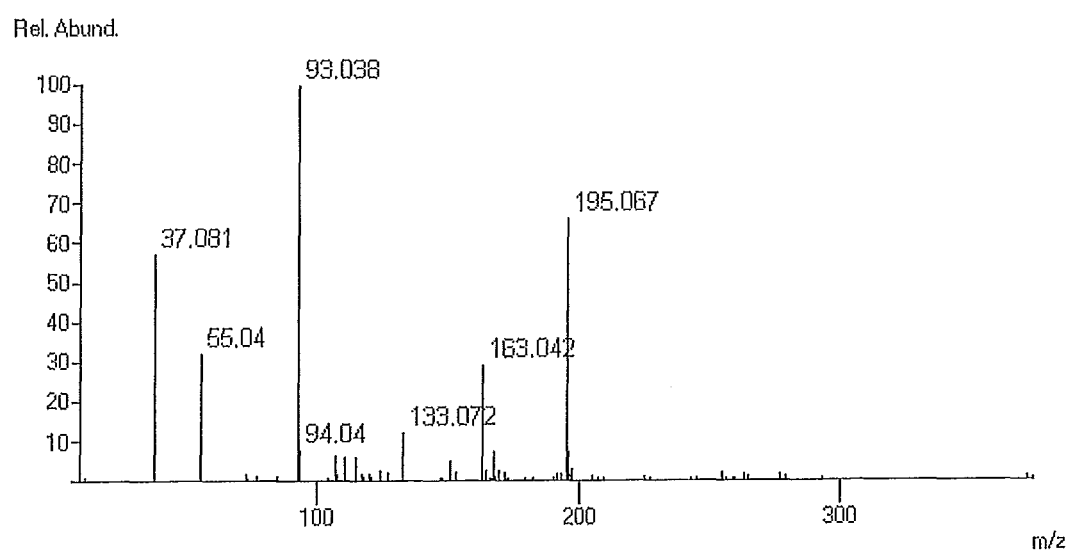
FIG. 26 illustrates a JEOL DART low temperature sample injection TOF Mass Spectrum of a composition of the present invention showing water clusters $[(H2O)n+H]+$ peaks at 37 and 55.
Figure 27:
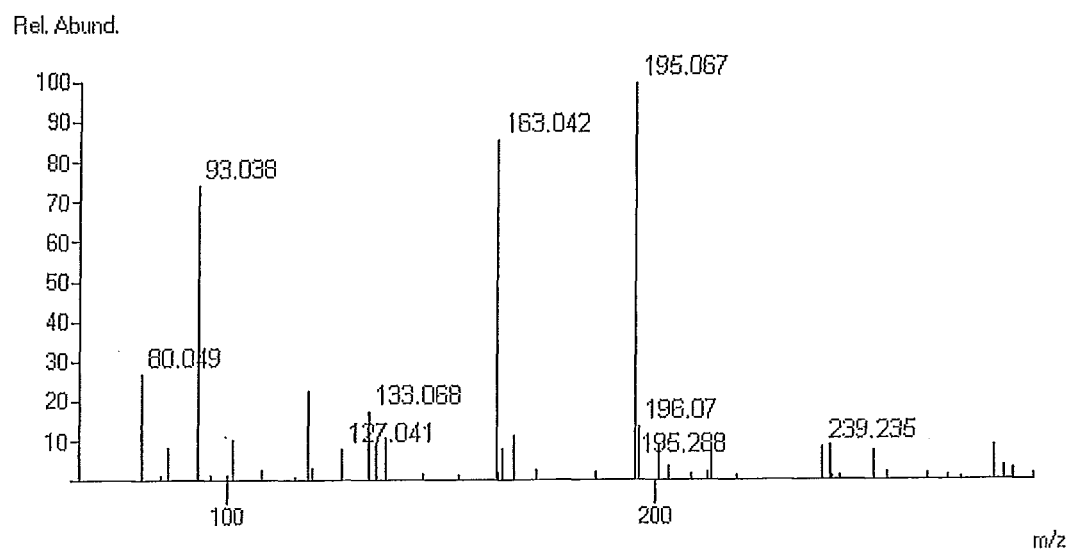
FIG. 27 illustrates a JEOL DART low temperature sample injection TOF Mass Spectrum of a composition of the present invention wherein the positive-ion mass spectrum, masses>m/z 60.
Figure 28:
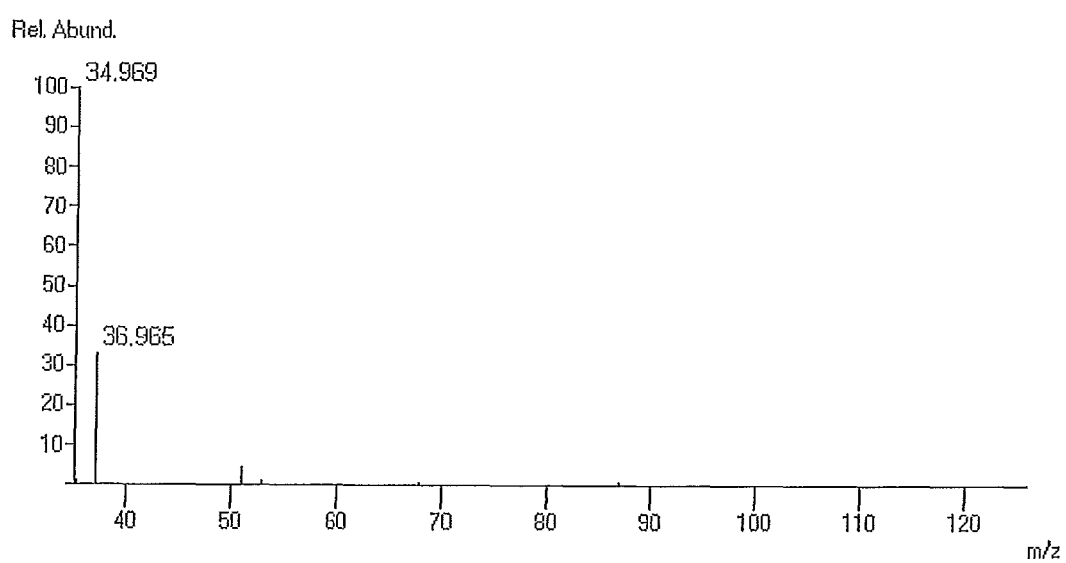
FIG. 28 illustrates a JEOL DART low temperature sample injection TOF Mass Spectrum of a composition of the present invention showing negative ions peaks at 35 and 37.

The spectra showed the existence of several active oxygen complexes, including ClO— and O2 in complexes with ClO— and the existence of the O2*- radical in several forms. These spectra are shown in FIGS. 26-28. At low mass, we see only water clusters [(H2O)n+H]+ at 37 and 55, filament Temperatures are low enough to not break down water.

Example 12

Hydrogen peroxide was tested by ultravioletvisible (UV/VIS) spectroscopy according to Standard Test Protocol (STP) Number STP0163 Rev2 by Nelson Laboratories in Salt Lake City. According to this test, hydrogen peroxide was present in a composition according to the present invention at 1.6 ppm by weight.

Example 13

Evaluation and measurements of pH, Peroxide, Chlorine, free and total, Redox and Ozone were taken from a composition made according to Example 3.

Three initial lots of materials were processed consisting of 15 sublots for run 1, sublots for run 2 and 40 sublots for run 3. During run 3, sublots 1, 15 and 30 were also tested for pH changes and Peroxide productions as intra-assay sublot controls. Starting material was also tested with each lot to determine which parameters changed during processing. Data showed a change in pH, Peroxide, Chlorine, free and total, as well as increased Redox and production of Ozone. There was no change in Osmolarity or Chloride levels but a decrease was seen in Sodium levels.

Samples from run 3 were also tested after 2 weeks storage at room temperature (~25° C.). At this time two samples of the material were removed and treated by freeze thaw and by heating to 100° C. in order to determine stability indicating parameters. This data showed that storage at room temperature for 2 weeks changed the Chlorine free and total levels and ratios from an initial mean value of the three runs of 60 to 60 ppm free to total and decreased to 16 to 52 ppm free to total. Freeze thawing this material gave values of 36 to 77 ppm, but heating further decreased these values to 8 to 32 ppm. The Sodium values after two weeks storage also appeared to be lower then the range (1.5 times standard deviation of the three runs) of 2470 to 4123 ppm down to 2100 ppm. This however did not appear to change (within assay variation) when samples were freeze thawed or boiled. The Chloride, Redox, and Peroxide appeared to be within error of the initial data for all three samples (2 week RT, freeze thawed and boiled). Osmolarity was slightly higher for the freeze thawed and boiled samples but may be within assay error or was due to the concentration of the sample caused by treatment.

Prior to initiation of PQ (Performance Qualification) runs, engineering runs were conducted to determine reproducibility of process and to generate material for determination of specific testing methods and parameters. Additionally, material was used to determine parameters that would be stability indicating. Material was produced using the apparatus and method described in Example 3. Unit has undergone IQ/OQ prior to study. Sublots were prepare using 0.9% sterile injectable Saline at one liter per sublot. Initial run consisted of 15 sublots that were pooled, pH adjusted and 0.2 u filtered. Aliquots were removed for initial testing using the following Steps.

Steps
1. Visual Inspection: Clear colorless liquid
2. Particulate matter: No visual particles under normal lighting
3. pH: Determination of pH was conducted based on United States Pharmacopoeia, USP <791> using GBI SOP EC-855. Instrumentation included a Corning 425 meter and an Accent 13-620-95 combination electrode. System was standardized at 25° C. using NIST traceable buffers that gave a slope of >97%.

4. Osmolarity: Determination of Osmolarity was conducted per USP <785> using an Osmette A model 5002 per GBI SOP AL-872. Unit was standardized with NIST traceable calibration standards and a reference control of 290 mOsm.

5. Peroxide: Generation of Peroxide was measured using a Peroxide test kit from Merckquant and semi quantitative levels were determined per GBI SOP AL-876. This test uses a test strip comparison method to a color scale. Levels of detection are 0.5, 2, 5, 10 and 25 ppm. Higher-level samples can be diluted and measured. Mid color estimates could be done if necessary.

6. Chlorine total and free: Free Chlorine in the sample as hypochlorous acid or hypochlorite ion (free Chlorine or free available Chlorine) immediately reacts with DPD (N,N-diethyl-p-phenylenediamine) indicator to form a magenta color which is proportional to the free Chlorine concentration. Color measurements are made using a Hach Colorimeter model DR850. Reagent kits are also obtained from Hach. It should be note that the presence of Ozone interferes with the accurate measurement of free Chlorine and the presence of Peroxides may interfere also.

Chlorine can be present as free or combined available Chlorine and is measured together as total available Chlorine. Combined Chlorine exits as monochloramine, dichloramine, nitrogen triChloride and other chloro derivatives. The combined Chlorine oxidizes Iodide in the test reagent to Iodine. The Iodine reacts with DPD along with free Chlorine present in the sample to form a red color that is proportional to the total Chlorine concentration. Combined Chlorine can be calculated by subtracting the free from the total Chlorine test result. It should be noted that Ozone and Peroxide in the sample might give inaccurate measurements with these reagents.

7. Redox Potential (ORP): This method measures the oxidizing or reducing capacity of a solution in mV units. A Platinum Redox Electrode (SympHony Electrodes) is utilized with a millivolt pH meter. Redox potential is expressed in terms of a standard electrochemical reduction potential, symbolized as E o, with millivolt (mV) as units. The value is measured against a standard hydrogen couple (2H+, H2), a universally accepted frame of reference. By convention, a positive (+) sign accompanies the reduction potential that has a greater tendency to undergo reduction relative to the hydrogen system. A negative sign is used for solution that have a lesser tendency to undergo reduction. Since the conventional standard is pH 7, measurements are pH dependent and appropriate calculation are required to adjust E o value to a condition applicable to pH (E o/). Example half-reaction couple potentials for water at 20 to 30° C. at pH 7 is 820 mV. (½O2+2H2+2e H2O).

8. Chloride: Chloride is measure using a Chloride combination electrode from Cole-Parmer (27077-04) attached to a IC 7685 Ion controller. Meter is calibrated with a 100 and 1000 ppm Chloride standard and samples are measured in terms of ppm Cl—. A 500 ppm reference standard is also used to determine reproducibility of the readings for Quality purposes.

9. Sodium: Sodium is measure similar to Chloride using a Sodium combination electrode from Cole Parmer (277077-16). Standards of 100 and 1000 ppm are used and a 350 ppm reference standard is also used to determine reproducibility of the readings for Quality purposes.

10. Ozone: Measurements of Ozone levels are made using a HACH colorimeter Indigo method. Method has a detection level of 0.1 ppm. Ozone (O3) is the gaseous form of Oxygen having 3 atoms per molecule rather than the usual 2.

Results: Samples from pre-treated 0.9% Sodium Chloride for injection were measured against post treatment product. Table 1 shows the mean, standard deviation (SD) and percent coefficient of variance (% CV) for the three lots. No trends were present based on the number of sublots prepared from values obtained on the initial lot consisting of 15 sublots, the second lot that had 30 sublots and the third lot consisting of 40 sublots. Assays have not been qualified for intra and inter variability therefore trend analysis and % CV comparison can only be made between starting and treated samples and the contribution of assay variability and operator variability is presently not known. It is known from manufacturer's literature that the presence of Ozone and Peroxide may give inaccurate values for the Chlorine analysis. Also Redox analysis is pH dependent and the starting untreated saline may require adjustment to pH 7 in order to determine if increases in Redox potential are due to treatment or are just related to the differences in the pH of the two products tested at the same time.

Osmolarity is in agreement with the calculated values that should be obtained based on the manufacturer's specification for percentage of Sodium Chloride present. (The freezing point depression at Δ° C. for a 0.89% solution is 0.53. Osmolarity=Δ/1.86 or 0.285 Osm (285 mOsm). These values do not appear to change between non-treated, treated, nor over time, or after stress treatment of freezing or boiling (Table 7).

TABLE 7

| Test Performed | O time (Jul. 23, 2004) treated | RT stored material Aug. 5, 2004 Ctr | Ctr freeze thawed −20° C. | Ctr Boiled 100 C. 1 min |
|---|---|---|---|---|
| PH | 6.99 | 7.1 | 7.0 | 6.52 |
| Osmolarity mOsm | 285 | 287 | 290 | 296 |
| Peroxide Ppm | 10 | 10 | 10 | 10 |
| Chlorine Total mg/L (ppm) | 72 | 52 | 77 | 32 |
| Chlorine Free mg/L (ppm) | 67 | 16 | 36 | 8 |
| Redox mV | 830 | 830 | 840 | 870 |
| Chloride mg/L (ppm) | 4670 | 5180 | 5260 | 4680 |
| Sodium mg/L (ppm) | 2470 | 2100 | 2000 | 2040 |
| Ozone mg/L (ppm) | 0.61 | 0.43 | 0.23 | 0.20 |

Peroxide appears to increase and this increase appears to be stable to stress treatment. Ozone also increased post treatment but unlike Peroxide, appears to decrease over time and appears to be effected by stress treatments.

Levels of Sodium and Chloride in non-treated solutions are in agreement with calculated values. Chloride post treatment appears to be within assay error and appears to remain stable to stress treatment. Sodium appears to decrease when starting concentration is compared to treated samples. The overall net decrease for the three runs gave a mean of 1247+/−227 and appears to be statistically significant from assay variability. These decreased values, however, do not appear to change when samples were stressed.

Levels of free and total Chlorine and calculated combined Chlorine may not be valid due to interference from the presence of Ozone and Peroxide. Untreated starting material appears to have little if any measurable levels of Chlorine. Post treatment values increase to a mean of 60 ppm for free and total indicating no combine Chlorine is present. These values, however, might be influence by the presence of Ozone and Peroxide. It should also be noted that Chlorine has a tendency to be absorbed by plastics and may also be affected by the materials being used to collect and store the sublots and final bulk materials as well as the container used for sampling. Material stored for two weeks showed a change in the ratio of free and total and if calculated gave a value of 36 ppm of combine Chlorine with the values for Ozone and Peroxide being equivalent to the 0 time treated test results that showed values of 60 ppm for both free and total indicating no combined Chlorine present. If should also be noted that when stressed treated by heat, the Ozone values decreased and the total and free values for Chlorine also decreased. The stressed treated samples at initial testing gave a value of 0 for combine Chlorine, 36 ppm at 2 weeks and this sample when boiled gave a values of 24 ppm for combined Chlorine and 41 ppm after freeze thaw.

Determination of Stress Effects of Temperature:Engineering run three was stored at room temperature for two weeks in a PETG bottle. This material was re-tested after this period. Comparison of post treatment material from the 40 L pooled engineering Run #3 was originally performed and tested on Jul. 23, 2004. This material was stored at room temperature and samples taken and treated by freeze thawing and boiling to determine possible stability indicating assays. Data is shown in Table 2.

Sample preparation: Room Temperature sample removed directly from original container. Frozen sample was aliquoted into 50 mL (3×25 mL) conical tubes and frozen overnight. Sample was removed the following day, brought to room temperature and tested.

Boiled sample: 75 mL was placed in a 125 mL flask, covered with tin foil and placed into water bath. Temperature was brought to 1000 C. Sample was boiled for 1 minute and aliquoted into 50 mL conical tubes. (3×25 mL)

Conclusions: Additional testing will be conducted on the PQ runs to determine reproducibility of the values obtain. Stability studies will also be conducted to determine if variations are occurring over time when product is stored at refrigerated, room or elevated temperatures. Other testing by outside sources for biological activity is not yet available, however, storage containers, and time of holding may be important in determination of activity. Other testing for metals and leachable will be done as well as endotoxin and sterility on the PQ pooled filtered samples.

TABLE 8

Table 8; Summary Data of Engineering Runs

| | pre treatment | Post treatment | Parameter |
|---|---|---|---|
| mean | 5.65 | 7.05 | pH |
| SD | 0.84 | 0.04 | pre-4.5 to 7.0 |
| % CV | 14.87 | 0.54 | |
| range | 4.39 to 6.91 | 6.99 to 7.10 | |
| mean | 284.67 | 285.00 | exp277 to 326 |
| SD | 0.44 | 0.00 | Osmolarity |
| % CV | 0.16 | 0.00 | mOsm |
| range | 284 to 285.3 | 285 to 285.00 | |
| mean | 0.00 | 10.00 | ppm |
| SD | 0.00 | 0.00 | Peroxide |
| % CV | #DIV/0! | 0.00 | |
| range | 0 to 0.0 | 10 to 10.00 | |
| mean | 0.02 | 60.00 | Chlorine Total |
| SD | 0.02 | 8.00 | mg/L |
| % CV | 76.19 | 13.33 | |
| range | 0.00 to 0.05 | 48.00 to 72.00 | |
| mean | 0.01 | 59.33 | Free |
| SD | 0.00 | 5.11 | mg/L |

TABLE 8-continued

Table 8; Summary Data of Engineering Runs

| | | | |
|---|---|---|---|
| % CV | 33.33 | 8.61 | |
| range | 0.007 to 0.0 | 51.67 to 67.00 | |
| mean | 320.50 | 860.53 | mV |
| SD | 67.67 | 20.36 | Redox |
| % CV | 21.11 | 2.37 | |
| range | 219 to 422.0 | 830 to 891.07 | |
| mean | 5140.00 | 4776.67 | Chloride |
| SD | 213.33 | 395.56 | ppm |
| % CV | 4.15 | 8.28 | exp 5187 to 5509 |
| range | 4820 to 5460.0 | 4183.333 to 5370.00 | |
| mean | 4140.00 | 3296.67 | ppm |
| SD | 580.00 | 551.11 | Sodium |
| % CV | 14.01 | 16.72 | exp 3360 to 3571 |
| range | 3270 to 5010.0 | 2470 to 4123.33 | |
| mean | 0.01 | 0.49 | ppm (mg/L) |
| SD | 0.01 | 0.12 | Ozone |
| % CV | 66.67 | 24.20 | |
| range | 0 to 0.0 | 0.31 to 0.66 | |

| | Sodium Decrease | Redox Increase |
|---|---|---|
| mean | 1246.67 | 540 |
| SD | 226.67 | 84 |
| % CV | 18.18 | 15.56 |
| range | 906.667 to 1586.7 | 414 to 666.0 |

Example 14

In Vitro Bioactivity Study

Described are a variety of results from in vitro experiments, performed at national research institutions, investigating the bioactivity of a composition disclosed herein, when placed in direct physical contact with living cells. Specific investigations include in vitro toxicity and antioxidant efficiencies of the master antioxidants glutathione peroxidase (GPx) and Superoxide Dismutase (SOD) inside living cells and the translocation of two well-studied transcription factors (NF-kB, NRF2) known to regulate toxic response and antioxidant production in human cells. Some preliminary work on concentration dependence was also done as well as cell proliferation, counts associated with induced oxidative stress in human cells.

The objectives of the investigations were (1) to determine if any signs of toxicity (NF-kB activation) are manifest when varying concentrations of a certain redox signaling compound, ASEA, are placed in physical contact with living cells, (2) to determine if such direct contact affects the antioxidant efficacy of glutathione peroxidase (GPx) and superoxide dismutase (SOD) and (3) to determine if such contact activates translocational transcription (NRF2) associated with increased expression of antioxidants in living human endothelial cells and to verify the expression of such transcription factors by Western Blot analysis, (4) to determine the effect of this redox signaling compound on proliferation cell counts of human cells and associated markers (LDH) for cell viability and health, (5) to determine the effects of this redox signaling compound on cells that were stressed with cytokines (Cachexin), radiation and serum starvation.

The immune-supporting composition contains a redox-balanced mixture of RXNs, both reactive oxygen species (ROS) and reduced species (RS), that are involved in a large variety of pathways and receptor-site activity in human cells. For example, when cells are damaged, for any reason (ex. toxins, DNA breaks or infections), the native redox signaling messengers inside the cells can become imbalanced, most often manifest by the accumulation of intracellular oxidants and ROS (oxidative stress). The cell, so affected, will activate defense and repair mechanisms aimed to restore proper redox-signaling homeostasis and proper cellular function. If repair efforts are unsuccessful and normal homeostatic redox balance is not able to be restored, then within a few hours, the excess oxidants and ROS in such cells will facilitate apoptotic processes to internally digest and destroy the dysfunctional cell. Healthy neighboring cells will then divide to replace it. A complete field of science called "redox signaling" has been founded to study such processes, with literally thousands of references available.

It is the nature of certain redox signaling molecules, when unbalanced or isolated, to elicit immediate recognizable toxic responses in exposed living cells; hydrogen peroxide is one example of such a redox signaling molecule. The first-line cellular response to toxic substances involves the translocation of NF-kB into the nucleus as a precursor to the inflammatory response and other defense mechanisms. The movement of NF-kB into the nucleus can be visibly tracked in a living cell under a fluorescence microscope with the aid of fluorescent tag molecules. The observation of nuclear translocation of NF-kB is a sure marker that a toxic response has been initiated. Even low-level toxicity is detectable with this catch-all method; low-level concentrations of hydrogen peroxide, for example, produce an easily distinguishable positive toxic response.

A separate transcription factor, NRF2, moves into the nucleus in response to low-level oxidative stress and facilitates the increased production of antioxidants. Again, by the use of fluorescent tags, the nuclear translocation of NRF2 can be seen in cells under a fluorescence microscope. NRF2 nuclear translocation is a second-line-of-defense mechanism known to increase the production of protective enzymes and antioxidants such as glutathione peroxidase and superoxide dismutase. NRF2 translocation will often accompany low-level NF-kB activation and NF-kB activation (almost) always precedes NRF2 translocation. Substances that exhibit low-level toxicity, such as trace homeopathic toxins, have long been used to activate the NRF2 pathway in order to stimulate these natural defend-repair-replace mechanisms.

Enzymatic efficacy of antioxidants, such as Glutathione Peroxidase (GPx) and Superoxide Dismutase (SOD), can be determined through standardized ELISA tests that measure the time-related reduction of certain oxidants introduced into cell lysates after the living cells have been exposed to the test substance for a given period of time. The reagents of the ELISA test must be chosen as not to interfere or interact with the test substance. Other critical factors such as the time of exposure and concentration dependence must be experimentally determined.

Western Blot methods also exist to experimentally determine the quantities of GPx or SOD in cell lysates. These well-established molecular separation techniques and can be used to directly verify whether the quantity of such antioxidant enzymes has been increased in the sample. Measured antioxidant efficiency, however, remains the best indication of cellular antioxidant defense.

Monitoring cellular proliferation, cell counts and chemical indicators of cellular death are also commonly used to determine cellular viability and gross response to stressors such as radiation, cytokines and toxins. Cachexin, for example, is a potent toxin, a cytokine, that elicits immediate toxic responses and build-up of oxidative stress in exposed cells. Cells, so stressed, exhibit a greater tendency to undergo apoptosis and die, thereby releasing internal proteins (such as LDH) into the surrounding serum.

Normally, when the introduction of such stressors and toxins elicits oxidative stress conditions in the cell cultures, cell counts will fall, cellular proliferation will subside, and serum LDH levels will rise, indicating that cell death is occurring in the culture. Hydrogen peroxide, radiation and serum starvation can also elicit similar responses. Redox signaling messengers, as outlined above, are intimately involved in cellular reception of and response to such stressors; redox messengers are involved in mediating antioxidant production and action to protect the cells, repair mechanisms necessary to fix DNA and structural damage and also in mediating the apoptotic process that results in cell death.

Increasing the concentration of such redox messengers in the serum may serve to augment the efficiency of these normal cellular processes. The exact action of various redox signaling mixtures must be determined experimentally. Independent unpublished studies, involving Mass Spectroscopy, Florescent Spectroscopy and Electron Spin Resonance, have unmistakably verified the existence of several kinds redox signaling molecules in the composition described herein. Well-established redox electrochemistry also validates the existence of such redox signaling molecules. The stability of this redox-balanced mixture is many orders of magnitude greater than expected. The confirmed preservation of unstable moieties in this supplement might be explained by the existence of certain stable molecular complexes, some of them verified by mass spectroscopy that can shield radical interactions. Intellectual property agreements, however, prevent the disclosure of the details.

The following research was conducted on a best efforts basis by a senior researcher at a national laboratory and is designed to assess basic mode-of-action when a composition of the invention is placed into direct contact with human cells:

1. The initial dose range projected for in vitro studies was extrapolated from a 10 mL of a composition of the invention/kg equivalent oral dose from human trials.

2. Glutathione peroxidase (GPx) and superoxide dismutase (SOD) ELISAs were used to determine whether a composition of the invention alters enzymatic activity in murine epidermal (JB6) cells.

3. LDH (non-specific cellular death) levels and cell proliferation rates were determined for various cell types exposed to a composition of the invention.

4. Human microvascular endothelial lung cells (HMVEC-L) were treated with a composition of the invention and cell lysates were analyzed by GSH-Px and SOD ELISAs to determine whether antioxidant enzyme activities are altered.

5. HMVEC-L cells were treated with a phosphate buffered saline solution (PBS) negative control, 5% and 20% concentrations of a composition of the invention and a Cachexin positive control to determine the nuclear translocation activity of the p65 subunit of NF-kB (cytokine transcription) at 30, 60, 90 and 120 min intervals. Fluorescent microscopy techniques were employed to image cellular response.

6. Step (4) was repeated except nuclear translocation activity of P-Jun was determined as an extension/verification of step 4.

7. Two cultures of HMVEC-L cells, one with normal random cell cycles and another with serum starvation were treated with low <1% concentrations of a composition of the invention to determine the nuclear activity of NRF2 (antioxidant transcription) at 30, 60, 90 and 120 minute intervals compared to a negative (PBS) control.

8. A Western Blot analysis was done on extra-nuclear and intra-nuclear fractions, separated by differential centrifugation, of serum starved HMVEC-L cell cultures exposed to <1% of a composition of the invention compared with a positive hydrogen peroxide control to determine phosphorylation events (oxidant action) in the extra-nuclear fraction and NRF2 (antioxidant transcription) in the intra-nuclear fraction at 0, 30, 60, 90 and 120 min intervals.

9. Normal random cell phases of HMVEC-L cells were exposed to radiation and then treated with a composition of the invention. Cell counts were taken to determine survival.

10. The efficacy of Cachexin reception in confluent-phase and normal-phase HMVEC-L cells was determined through changes in extracellular and intracellular LDH activity in cells exposed to various mixtures of Cachexin, PBS and a composition of the invention solutions.

Experimental Methods used to Assess Toxic Response in Primary Human Lung Microvascular Endothelial Cells (HMVEC-L): HMVEC-L cells (catalog # CC-2527) were purchased from Lonza (Walkersville, Md.) as cryopreserved cells (Lot #7F4273). Cells were thawed and maintained according to manufacturer's directions. Cell culture medium (proprietary formulation provided by Lonza) contained epidermal growth factor, hydrocortisone, GA-1000, fetal bovine serum, vasoactive endothelial growth factor, basic fibroblast growth factor, insulin growth factor-1 and ascorbic acid.

HMVEC-L Cell cultures in normal random cell cycles were exposed to high-concentration ASEA in the serum medium, concentrations of 5% and 20%, and analyzed in conjunction with cultures exposed to phosphate buffered saline solution (PBS) as non-toxic negative control and Cachexin (5 ng/mL) as a positive control (highly toxic). At intervals of 0, 30, 60, 90, and 120 minutes, aliquots of cells from each culture were placed under a fluorescent microscope, stained by fluorescent dyes designed to tag the p65 subunit of NF-kB along with a DAPI fluorescent nuclear stain that aids the computer software to find the nuclei. Computer automated imaging techniques were used to determine the relative degree of translocation NF-kB into the nucleus via fluorescent analysis over several cells. As a reminder to the reader, P65 NF-kB translocation is the first-phase non-specific cellular response to toxicity. Thus the movement of the NF-kB into the nucleus, as seen visually in the microscope images, is a sensitive indicator of general toxic response.

Results of HMVEC-L Cells p65 subunit NF-kB screen for toxicity: Typical cell images are shown below for each culture. Translocation of p65 subunit of NF-kB into the nucleus was not seen in any cell cultures exposed to high-concentration a composition of the invention. Automated analysis confirmed this and indicated no toxic response at 0, 30, 90 and 120 minutes. In contrast, Cachexin exposed cells exhibited an immediate sustained toxic response (FIG. 25).

Cachexin is positive control and induces the translocation of p65 subunit of NF-kB from cytosol into nucleus. DAPI staining shows position of nuclei in these images (see arrow of FIG. 25). A composition of the invention (5 and 20% final v/v) did not induce nuclear translocation of NF-kB at 30, 60 and 120 min time points.

Given this null indication of toxicity after exposure to high concentrations of ASEA, another test was performed to confirm behavior.

Additional Method to Assess Toxic Response of HMVEC-L Cells (P-Jun): A similar methodology as that employed with NF-kB was employed to determine the nuclear translocation of an anti-phospho-Jun (AP-1 P-Jun)

antibody index (P-Jun is another toxicity-related redox-responsive transcription factor). HMVEC-L cells were again exposed to high-concentration ASEA. All procedures were similar to the NF-kB analysis except for the substitution of P-Jun fluorescent indicators and automated measurements taken over 100 cells in order to increase sensitivity. An additional naïve (untouched) culture was also analyzed.

Results for P-Jun screen for toxicity (FIG. 29): AP-1 index determined using anti-phospho-Jun (P-Jun) antibody. AP-1 is nuclear localized and upon activation, the phosphorylation status of P-Jun is increased. Anti-P-Jun antibody binds to the phosphorylated form reflected as an increase in fluorescence intensity (see Cachexin control). A consistent trend reflecting an increase in P-Jun levels was not observed for cells treated with 5% or 20% ASEA at 30, 60 and 120 min time points, while the Cachexin positive control significantly increased nuclear P-Jun levels at 30 min.

Again no toxic response was observed; there was no significant accumulation of P-Jun in the nuclei of cell cultures exposed to high concentrations of a composition of the invention. Automated analysis indicated no toxic response at 0, 30, 90 and 120 minutes, with a slight but non-significant increase for 20% a composition of the invention at the 30 minute time point; at other time points no increase was detected. In contrast, the Cachexin exposed cells (positive control), as expected exhibited an immediate sustained toxic response.

The results of the P-Jun analysis concurred with the response seen in the NF-kB analysis. For both tests, there was no significant difference between a composition of the invention exposure and that of the negative PBS control for healthy random-phase HMVEC-L cells. This confirmed lack of toxicity was somewhat unexpected for this mixture of redox signaling molecules, considering that some of them, if isolated from the mixture, are known to elicit an immediate response.

Since nuclear translocation of NF-kB and P-Jun are typically the first responders to serum toxicity and are known to initiate the inflammatory response, especially in the ultra-sensitive human endothelial cells, healthy human cells when directly exposed to a composition of the invention, are not expected to exhibit defensive behavior nor initiate inflammatory processes (such as the release of inflammatory cytokines). It is not certain from this data whether exposure would suppress or reverse the inflammatory process.

Blood serum levels of such redox signaling molecules, for all in vivo oral applications, would not exceed serum concentrations of 1% and typically would be less than 0.1%. Serum levels are expected to drop over time due to enzymatic breakdown of the components. Independent in vivo pharmacokinetic studies indicate that the active components in ASEA have approximately a 17 minute half-life in the blood and thus would be effectively cleared from the blood within a few hours. Thus no toxic response is expected due to exposure of healthy human cells at such levels. It has been seen in these in vitro studies that direct exposure of human cells to serum concentrations of up to 20% is still well tolerated. The complete lack of toxicity, comparable to the PBS control, is extremely rare and indicates that despite the reactivity of this mixture, it is well tolerated by human tissues and is native to or compatible with the extracellular environments.

Experimental Methods Used to Determine Antioxidant Efficacy of Glutathione Peroxidase (GPx): Cell cultures of standard murine epidermal cells (JB6) were exposed to various small concentrations of a composition of the invention (less than 1%) and PBS solution for 24 hours. Cell lysates were prepared for measurements of GPx enzymatic activity using a commercially available ELISA kit (GPx activity kit, Cat #900-158) according to directions of the manufacturer (Assay Designs, Ann Arbor, Mich.). Decrease of oxidants due to GPx enzymatic activity was monitored over an 11 minute period of time after a chemical agent (cumene hydroperoxide) initiated the reaction. The decrease of oxidants is an indication of antioxidant efficacy. To determine GPx efficacy at various concentrations of PBS or a composition of the invention, three replications of oxidant residual in the samples were read every 2 min to generate the slope, indicating the decrease in relative fluorescence units (RFU)(oxidant residual) per minute.

Results and Observations for GPx Antioxidant Efficacy Test: After activation, the reduction of oxidants over time was closely linear, as seen in the graphs below (RFU units on vertical scale). A well-defined slope was established over the 11 minute interval (FIG. 27). Antioxidant activity is measured by reduction of oxidants over time (FIG. 28).

A significant increase in antioxidant activity was seen in samples infused with ASEA compared to the PBS control (second graph).

Concentration dependency, however, was not seen between the 5 ul, 10 ul and 20 ul infusions. This suggests that GPx antioxidant activity might saturate at concentrations lower than that represented by the 5 ul infusion. Such considerations will be discussed later.

The table below summarizes the data shown on the preceding graphs.

| Sample Infusion Volume (<1% total volume) | Slope for PBS Control (% reduction/minute) | Slope for ASEA (% reduction/minute) |
|---|---|---|
| 0 ul | 0.1% | 0.1% |
| 5 ul | 0.1% | 3.6% |
| 10 ul | 0.2% | 3.6% |
| 20 ul | 0.3% | 3.7% |

The raw data reflects more than a 10 fold increase in antioxidant activity related to ASEA infusion. Taking into account experimental uncertainties, it is 98% certain that the serum infusion of small concentrations (<1%) of a composition of the invention increased antioxidant efficiencies by at least 800%. Further investigations should be done to confirm this increase and explore concentration dependence for these low-level serum concentrations.

Experimental Methods Used to Determine Antioxidant Efficacy of Superoxide Dismutase (SOD): Human HMVEC-L cells were treated with 10% phosphate buffered saline (PBS; vehicle control), 5% or 10% of a composition of the invention for 24 hr at which time cell lysates were prepared for measurements of SOD activity using a commercially available kit (SOD activity, cat #900-157) according to manufacturer's (Assay Designs, Ann Arbor, Mich.) directions. Cell culture medium was assayed for SOD activity in parallel. Limited trials with smaller concentrations of a composition of the invention <1% and murine epidermal cells were also attempted.

Results of First-Attempt Methods to Determine SOD activity for high serum a composition of the invention concentration: Diluted lysates showed a marginal increase in enzymatic activity associated with treatment with a composition of the invention. Changes in enzymatic activity were marginal in the initial range of 5-10% a composition of the invention (final concentration, v/v). The data represent the first attempt to measure SOD activity using primary HMVEC-L cells treated with a composition of the invention. It is feasible that the lack of SOD activity associated with 5-10% a composition of the invention might be related to non-specific inhibition at high dose. The primary concern is that we have little understanding of the primary human HMVEC-L cell model and cannot determine whether these cells are optimal for investigating antioxidant defense regulation induced by a composition of the invention. For example, ascorbic acid, known to break down certain redox signaling complexes in A a composition of the invention, is supplemented into the medium and it is feasible that some modification of the medium formula (such as omission of ascorbic acid for short periods of time defined empirically) could produce more optimal conditions for detecting antioxidant defense regulated by a composition of the invention. Initial efforts to serum-starve these cells, as one approach to increase sensitivity and optimize the model, were unsuccessful and resulted in extensive cell death over 24 hours, indicating that the cells are dependent on the growth factors supplemented in the cell culture medium to maintain cell viability. If we interpret the initial a composition of the invention concentrations (5-10%) to be high (based on inhibition of medium enzymatic activity and cell proliferation), then it is possible that the marginal increase in enzymatic activity associated with cell lysates observed here may not accurately reflect antioxidant defense regulation possibly occurring at lower concentrations. The use of an in vitro model system with a well defined and robust NRF2-regulated antioxidant defense response would help address some of these uncertainties. In retrospect, we have observed that a lower concentration of a composition of the invention (1%) induces the nuclear translocation of the NRF2 transcription factor. In addition, the 24 hr time point was chosen for the initial screen as a general time point for in vitro investigations that would capture transcriptional regulation; however, this time point was not optimal.

Results of Further Investigations into SOD enzymatic activity at low composition of the invention concentrations (<1%): It was found in another investigation that NRF2 nuclear translocation (data and results are in the following sections), took place at low doses of a composition of the invention (less than 1%) and elicited peak SOD antioxidant activity at about 30 to 120 minutes after exposure. Thus when SOD antioxidant activity was measured due to low-concentration composition of the invention exposure at 30 to 120 minute time points, results similar to the GPx enzymatic activity were seen both with murine epidermal (JB6) cells and serum-starved HMVEC-L cells at a time point 90 to 120 minutes. A 500% increase in peak SOD enzymatic activity was estimated over a short 120 minute term, with 95% confidence.

Experimental Methods Used to Determine Nuclear Translocation of NRF2 in HMVEC-L Cells and Western Blot Verification: HMVEC-L cells were again thawed and maintained according to manufacturer's directions. The culture medium contained epidermal growth factor, hydrocortisone, GA-1000, fetal bovine serum, vasoactive endothelial growth factor, basic fibroblast growth factor, insulin growth factor-1 and ascorbic acid in randomly cycling cultures. Ascorbic acid was withheld from serum-starved cultures.

HMVEC-L Cell cultures in both normal random cell cycles and in serum starvation were exposed to high-concentration (5-20%) and low-concentration (1%) ASEA in the serum medium and analyzed in conjunction with cultures exposed only to phosphate buffered saline solution (PBS), as a negative control. At time points of 30, 60, 90, and 120 minutes, aliquots of cells from each of the cultures were placed under a fluorescent microscope, stained by a fluorescent dye designed to tag the NRF2 transcription factor along with the DAPI fluorescent nuclear stain that aids the computer software to find the nuclei. Computer automated imaging techniques were used to determine the relative degree of nuclear accumulation of NRF2 via fluorescent analysis over several cells. NRF2 regulates the transcription of a number of phase II antioxidant defense enzymes and raises the possibility that additional antioxidant defense enzymes, such as glutathione transferase, may be expressed through exposure to ASEA. Thus the accumulation of NRF2 into the nucleus, as seen visually in the microscope images, is an indicator of increased antioxidant expression in the cells.

Results of HMVEC-L Nuclear Accumulation of NRF2: Initial screen of human endothelial cells suggests a subpopulation of cells showed increased nuclear staining pattern (focal) following treatment with high-concentration of a composition of the invention. The positions of nuclei are indicated by DAPI stain in lower panel. Foci appear brighter in a composition of the invention stimulated cells which indicates higher level of NRF2 transcription factor in the nucleus. H2O2 was used as positive control. This effect was difficult to quantify based on nuclear staining pattern. (FIG. 36)

Typical cell images are shown below for indicated cell cultures exposed to low-concentrations of a composition of the invention. Accumulation of NRF2 into the nucleus was clearly seen in serum-starved cell cultures exposed to low-concentrations of a composition of the invention. Automated analysis revealed strong time-dependent nuclear accumulation of NRF2 in serum-starved cells, relative to the negative control, at the 30 and 60 minute time points (FIG. 30).

The nuclear staining profile was qualitatively different from the cells maintained in optimal growth medium (randomly cycling group). There was weak qualitative nuclear accumulation of NRF2 induced by exposure to a composition of the invention in these cells at 30, 60 and 120 minute time points, and yet the effect was not nearly as pronounced as in the serum-starved cultures. However, serum-starvation induced significant cell death complicating interpretation of the data. The trends appeared weak and require validation by Western Blot.

Experimental Methods for Western Blot Validation of NRF2 Nuclear Accumulation: HMVEC-L were treated with 1% of a composition of the invention, nuclear extracts were separated through centrifugal differentiation from the extra-nuclear cytosol at 30, 60 and 120 min and subjected to Western Blot analysis for NRF2. In the Western blot experiment the extra-nuclear fraction was probed for phosphorylated proteins using a combination of anti-phospho serine, threonine and tyrosine antibodies. Virtually all cellular processes are regulated by posttranslational modifications and protein phosphorylation is a prevalent mechanism. Observable changes in protein phosphorylation can lead to a mechanistic understanding of the cellular processes perturbed by compositions of the invention and provide a defined endpoint to better define dose-dependent regulation of cell function by compositions of the invention in vitro, as well as provide a potential candidate molecular marker that may be used to provide in vitro-in vivo correlates. Hydrogen peroxide (H2O2) was included as a positive control for oxidant damage.

Figure 31:
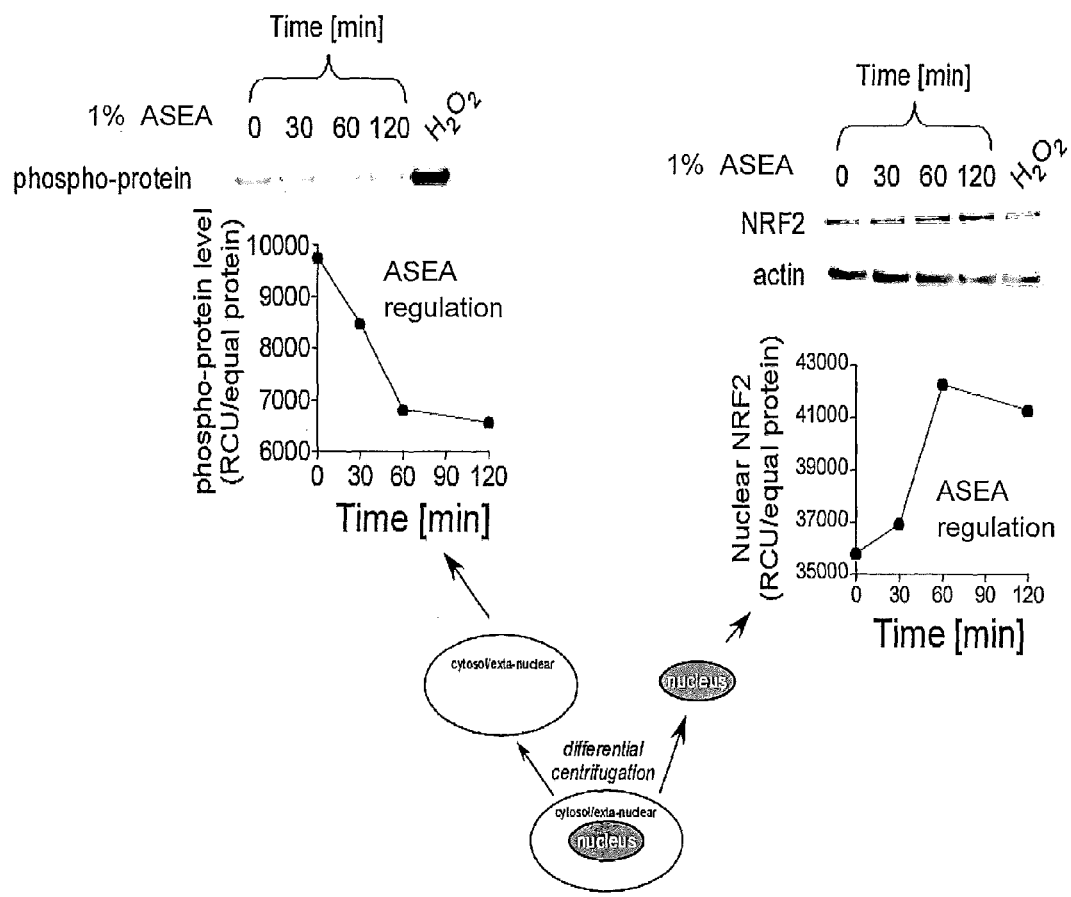
FIG. 31 illustrates a western blot validation of NRF2 nuclear accumulation following ASEA (a composition disclosed herein) treatment.

Results for Western Blot Validation of NRF2 Nuclear Accumulation: NRF2 levels were increased in a time-dependent fashion in nuclear extracts prepared from HMVEC-L cells treated with 1% ASEA. H2O2 (30 min) did not increase nuclear NRF2 levels. In contrast, when protein phosphorylation was examined in the extra-nuclear fraction (separated from nuclei by differential centrifugation) we observed a single band by Western blot analysis and this is likely due to the dilution of the extra-nuclear fraction during the cell fractionation process (other phosphorylated proteins are obviously present but are below detection limits under these conditions) or specificity of the anti-phospho-antibodies used was insufficient to detect a broad range of phosphorylated proteins. However, we did observe a marked increase in the phosphorylation of the protein detected following H2O2 treatment, indicating that this phosphorylation event is highly sensitive to redox regulation or activation of protein kinase/deactivation of protein phosphatase activities subsequent to oxidative damage. Treatment of cells with 1% of a composition of the invention decreased phosphorylation levels associated with this protein in a time-dependent fashion (FIG. 31).

Reductions in phospho-protein regulation in extra-nuclear fractions were seen along with strong time-dependent NRF2 accumulations in the nuclear fractions, indicating clear time-dependent up-regulation of antioxidant expression.

At this point it is worth mentioning that NRF2 activity has been clearly detected in conjunction with exposure to a low-concentration of a composition of the invention without the normal prior NF-kB activity. This suggests that phase II antioxidant defense mechanisms have been stimulated without the normal prior phase I toxic response. This behavior has no precedent or is extremely rare. It appears from the data that compositions of the invention are able to stimulate antioxidant expression without ever eliciting a prior low-level phase I toxic response.

Experimental Methods to Determine Proliferation of Murine (JB6) Cells and HMVEC-L Cells and LDH Activity with Exposure to ASEA: HMVEC-L cells were treated with 5-20% ASEA for 72 hr and cell number was determined using a Coulter Counter. Control (0 concentration group) was treated with 20% PBS. Serum LDH levels were also measured as an indicator of cell culture viability at 0 to 20% concentration of the compositions of the invention/serum concentrations. Recall that lower serum LDH concentrations indicate less cell membrane failure. Similar experiments were performed for murine (JB6) epidermal cells.

Figure 32:
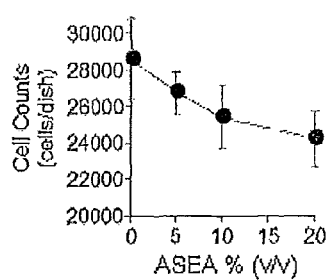
FIG. 32 illustrates results for proliferation of murine and HMVEC-L cells and LDH activity following ASEA (a composition disclosed herein) treatment.

Results for Proliferation of Murine and HMVEC-L cells and LDH activity: The initial in vitro screen indicates that high-concentrations of compositions of the invention in serum may inhibit cell proliferation (for both murine epidermal cells [JB6] and primary human lung microvascular endothelial cells [HMVEC-L]) in the concentration range of 5-20%. In this concentration range we also observed direct inhibition of LDH enzymatic activity. The data are somewhat contradictory as the decreasing cell counts indicate cell death, yet lower serum LDH levels indicate higher cellular membrane integrity. At the highest concentration tested (20% v/v), cell proliferation was inhibited by approximately 20% (FIG. 32).

Figure 33:
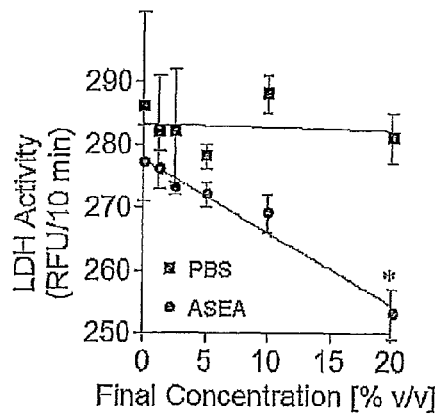
FIG. 33 illustrates that high concentration ASEA (a composition disclosed herein) exposure reduced serum LDH activity in HMVEC-L cells.

The mechanism behind reduced proliferation cannot be deduced and could be related to interference with growth factor responsiveness or other possible interpretations such as enhanced programmed death (apoptotic response) for damaged cells. It is noteworthy that high serum concentrations of composition of the invention for in vitro enzymatic enhancement studies is not optimal, it is possible that the initial screens underestimated or even missed antioxidant defense (SOD) regulation by a composition of the invention and thus indicate that low-concentration (<1%) compositions of the invention and/or short exposure times should be employed for such purpose (FIG. 33).

Further studies were done that investigated the action of stressed cells upon exposure to compositions of the invention; the source of stress resulting from a variety of chemical and environmental stressors. These investigations offer clues for the possible mechanisms.

Experimental Methods to Determine cell viability of HMVEC-L exposed to various mixtures of Cachexin stressor and high-concentration compositions of the invention: HMVEC-L cultures with normal random cell cycles (pS) and cultures approaching confluence (A2), which are generally less sensitive to Cachexin, were infused with escalating concentrations of Cachexin stressor (0-5 ng/mL). These cultures had been pretreated with either a 10% PBS control or 5-10% concentration of a composition of the invention for 24 hours. Two indicators for cell viability were employed. Serum LDH levels were obtained as an indication of membrane integrity and Neutral Red dye was used as an indication of lysosomal integrity. Recall that as cell membranes fail, LDH is released into the serum medium. Lower quantities of LDH indicate higher cell viability. The integrity of lysosomes, necessary for viable cell function, are measured by absorption of Neutral Red dye stain. Higher quantities of Neutral Red absorbance indicate higher cell viability.

Figure 34:
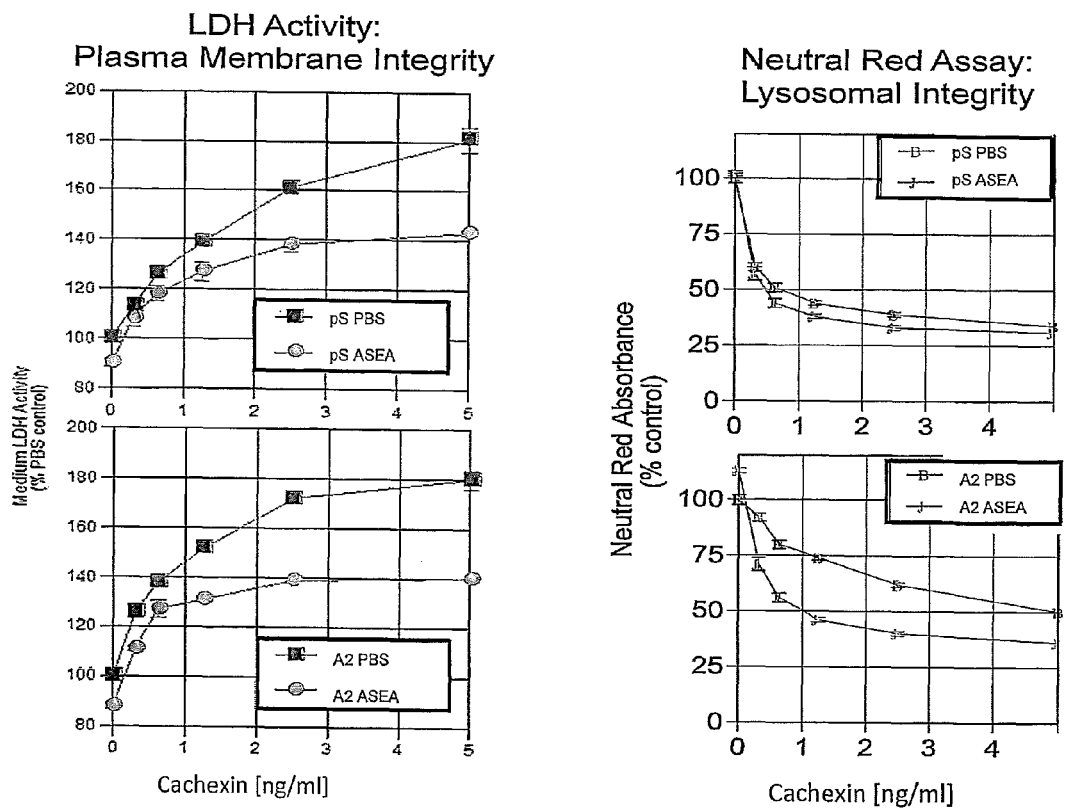
FIG. 34 illustrates results of HMVEC-L viability exposed high-concentration ASEA and to escalating amounts of Cachexin stressor (the composition embodiment used in the protocol is referred-to as "ASEA").

Results of HMVEC-L viability exposed high-concentration composition of the invention and to escalating amounts of Cachexin stressor (FIG. 34): Both confluent (A2) and normal (pS) HMVEC-L cultures exhibited up to 30% improvement (relative to PBS controls) in LDH levels related to exposure to compositions of the invention after acute (up to 5 nm/mL) Cachexin insult. The LDH data suggest that HMVEC-L cells stressed by Cachexin are less likely to die due to cell membrane failure after being exposed to compositions of the invention.

Behavior of lysosomal integrity in HMVEC-L cells as measured by Neutral Red absorption exhibited behavior dependent on cell culture phase. As expected, the confluent (A2) cells in the PBS control were much less sensitive to Cachexin insult than cells in the PBS control normal random phase (pS) culture; this is evidenced in the 5 ng/mL Cachexin data: Lysosomal levels in A2 cells dropped only 50% compared to 70% in the pS culture. Exposure of the normal (pS) cultures to compositions of the invention made little difference in lysosomal integrity under similar Cachexin insult, yet exposure of confluent (A2) cell cultures to ASEA made them much more sensitive to Cachexin insult, regressing to behavior similar to that exhibited by the normal more sensitive (pS) cells.

This is the first evidence presented that suggests that exposure of abnormal (Cachexin-insensitive) HMVEC-L cells to compositions of the invention can make them more sensitive. The data suggest that confluent (A2) cells stressed by Cachexin are more likely to die when exposed to compositions of the invention, these abnormal cells when exposed to ASEA exhibit closer to normal behavior in the presence of Cachexin. This behavior was initially unexpected as the hypothesis of the experiment was that compositions of the invention would help cells protect themselves against toxic insult. As it turns out, it appears that compositions of the invention exposure only helps normal healthy cells to protect themselves against oxidative insult and yet seems not to help cells protect themselves against Cachexin. Exposure to compositions of the invention may even help facilitate the death of the stressed cells that are close to the end of their normal life cycle. Incidentally, the normal role of Cachexin in the tissues is to facilitate the death and replacement of damaged cells.

Experimental methods to determine the compositions of the invention concentration-dependent response of A2 and pS phase HMVEC-L cells to Cachexin insult: HMVEC-L cell cultures, prepared in two phases, in the confluent end-of-life-cycle A2 phase (a phase typically insensitive to Cachexin insult) and in the normal random cycle pS phase were exposed for 24 hours to serum concentrations (v/v of 2.5%, 5%, 10%, 15% and 20%) of either the PBS control or a composition of the invention. Cachexin responsiveness was then determined by monitoring LDH activity in both the intracellular cytosol and in the surrounding growth media. Recall that increased LDH activity in the growth media indicates cell membrane rupture and death (LDH release) and the decrease of intracellular LDH activity indicates loss of cellular integrity. Thus the cell cultures that are responsive to Cachexin insult would experience an increase in medium LDH activity and a decrease in intracellular LDH activity.

LDH activity in untouched cell culture controls were compared to that of cell cultures insulted with 5 ng/mL Cachexin for each composition of the invention concentration considered. The concentration dependence of compositions of the invention was then graphed against LDH activity for each insulted culture and control.

Results of concentration-dependent response of HMVEC-L cells to Cachexin insult (FIG. 35): Relative to the PBS control, the Cachexin response for the normal pS cells was much smaller than expected. Only slight decreases in cell membrane integrity were seen in the PBS control cultures and the intracellular LDH activity remained the same. With exposure to compositions of the invention, by itself, the normal pS cell cultures suffered a slight decrease in overall cellular integrity and increase in cell death. It should be noted that since the large expected response of the control pS cells to Cachexin was not manifest, it is probable that the pS cell cultures used in this investigation were nearing a confluent or non-responsive state.

There was, however, a clear response when Cachexin insult was added to the pS cell cultures exposed to various composition of the invention concentrations, cultures demonstrated a clear loss of intracellular LDH function and integrity. However, the accompanying indication of cell death was not seen. This seems to indicate that the "normal pS" cells were made more sensitive to Cachexin reception by composition of the invention exposure, yet not brought completely to the point of cell death.

The A2 cell culture response was very clear. Composition of the invention exposure, even without Cachexin, seemed to cause loss of intracellular LDH integrity, though it did not affect cell death. However, when Cachexin insult was applied to such A2 cultures, composition of the invention exposure clearly amplified the Cachexin reception rapidly decreasing cellular function and there were also clear indications of concentration-dependent cell death. There is strong evidence that exposure to compositions of the invention increases Cachexin responsiveness in the A2 cell cultures.

The results imply that exposure to compositions of the invention significantly increases Cachexin responsiveness in A2 and borderline pS HMVEC-L cell cultures. Of possible interest, exposure to compositions of the invention alone might decrease integrity of cellular LDH activity in A2 type cells; recall that zero toxic response was detected in randomly cycling cells even under large concentrations, so effects due to toxicity are not expected in normal cells. It appears that exposure to composition of the invention may tend to accelerate the removal of non-responsive confluent cells. This is evidently true when Cachexin is present. These results might also bear on the observations that exposure to compositions of the invention seemed to diminish cell proliferation in high concentrations. No such trend was tried for low-concentration exposure. Note that it is difficult to discount the possibility that high-concentration effects might simply be artifacts due to the interference of compositions of the invention with the growth medium.

Experimental methods to determine effects of 5-10% composition of the invention exposure to cells stressed by radiation and serum starvation: Murine (JB6) cell cultures were subjected to high-level radiation exposure (X-rays) and, in a separate investigation, cultures were subject to serum starvation of growth factors for 24 hours. The cells were then exposed to 5-10% ASEA exposure as means to determine the effect of composition of the invention exposure on such stressed cells. Cell counts were taken before and after composition of the invention exposure.

Results of effects of 5-10% composition of the invention exposure on radiation and serum-starved murine cells: Quantitative analysis was not compiled for these experiments. Qualitative analysis, however, reveals results that might be of some interest. For the radiation-damaged culture, immediate cell death was observed for more than half of the culture upon exposure to composition of the invention. No further cell-death was seen thereafter. Upon inspection under a microscope, the remaining living cells appeared normal and healthy. It appears that exposure to a composition of the invention may have helped accelerate cell death among the more seriously damaged cells and allowed for the survival of healthy or repairable cells.

For serum-starved cell cultures similar observations were made, except the cell death was not nearly as severe, amounting to less than roughly a 20% loss. Surviving cells appeared to be very robust and viable. Similar losses, however, were also seen in serum-starved cultures that were not exposed to compositions of the invention in later experiments.

A better understanding of the bioactivity of a certain mixture of redox signaling molecules has been determined from in vitro studies involving direct contact of compositions of the invention with viable living HMVEC-L human cells and murine epidermal JB6 cells. Five specific objectives were pursued to determine:

1) In vitro toxicity (based on NF-kB, P-Jun translocation)
2) Effects on antioxidant efficacy (for GPx and SOD)
3) Effects on antioxidant transcriptional activity (NRF2)
4) Effects on cell proliferation and viability (cell counts)
5) Effects on stressed cells (Cachexin, radiation, starvation)

No toxic response was observed for any healthy cell culture in normal random phases (HMVEC-L or JB6) upon exposure to high concentration compositions of the invention (up to 20%) of serum. Two methods were used to determine toxic response, the translocation and accumulation of NF-kB and P-Jun in the nuclei. Both of these methods are known to be sensitive to low-levels of toxicity, as verified by the positive control. A complete lack of toxic indication and/or inflammatory cytokines was observed.

An 800% increase in GPx antioxidant efficacy in HMVEC-L cells was seen after 24 hours exposure from low-concentration composition of the invention (no concentration dependence seen). A transitory increase of up to 500% was seen in SOD antioxidant efficacy between 30 to 90 min. again after exposure to a low-concentration of a composition of the invention (<1%). In both cases, the low concentrations of compositions of the invention were comparable to blood concentrations possible from oral dosing, though data is not available to confirm this. Concentration dependence at very low concentrations might be seen if such was carefully investigated.

Exposure to high-concentration compositions of the invention, in comparison, elicited only a small relative increase in GPx antioxidant efficacy that was not concentration dependent. An increase in SOD efficacy was not seen for either high-concentration compositions of the invention or after long (24 hr) exposures. In subsequent investigations, this information will be used to determine optimal concentrations and time points to study concentration dependence (<0.1% and 0-120 minutes).

Studies examining the nuclear translocation of redox responsive transcription factors suggest that compositions of the invention at a lower concentration (less than 1%) induces a 20-30% increase in the nuclear translocation of the NRF2 transcription factor in HMVEC-L cells that appears to be transient (30-60 min). We also observed that a composition of the invention induced a parallel decrease in the phosphorylation of an extra-nuclear protein whose phosphorylation status is clearly increased in response to hydrogen peroxide treatment, consistent with an antioxidant mode of action.

Serum-starving HMVEC-L cells, as an approach to increase sensitivity, significantly increased the nuclear NRF2 signal induced by composition of the invention (1%). However, serum-starvation induced significant cell death complicating interpretation of the data.

Cellular proliferation for both HMVEC-L and JB6 cell types (determined from cell counts) was inhibited by high concentrations (5-20% v/v) of exposure to compositions of the invention. The HMVEC-L inhibition was clearly concentration dependent, with a 20% loss of cell count at 20% ASEA concentration. In contrast to decreased proliferation, serum LDH levels significantly decreased with compositions of the invention concentration between 5-20%, indicating increased cell membrane integrity. The results seem to indicate that cellular proliferation is decreased while cell membrane viability is increased at high concentrations. The mechanism behind such behavior cannot be deduced from the data, yet further evidence will be seen in the next section.

The response of HMVEC-L cells when stressed with Cachexin depends upon cell phase. Normal randomly cycling HMVEC-L cells (pS) exhibited typical behavior when stressed with Cachexin: exhibiting decrease in cell viability accompanied by cell death. Confluent end-of-life-cycle (A2) and borderline HMVEC-L cells, as expected, were less sensitive to Cachexin insult, exhibiting less pronounced decreases in cell viability and less cell death.

Exposure to compositions of the invention caused no significant change in the response of the normal random cycling pS cells to Cachexin (showing similar loss of cell viability and cell-death). However, A2 cell cultures exposed to a composition of the invention exhibited increased sensitivity to Cachexin, restoring behavior similar to that of normal cells. This behavior was reinforced as concentration dependence was examined. Borderline A2 cells, exhibiting a relatively small Cachexin response, and A2 cells that are normally insensitive to Cachexin insult, exhibited a much stronger response to Cachexin when exposed to compositions of the invention, both in decrease in viability and increased cell death.

It appears that exposure to compositions of the invention causes increased rates of A2 cell death, enhancing the natural reception of Cachexin in such end-of-life-cycle cells. Yet exposure to composition of the invention is not expected to cause any change in normal cell viability.

Cachexin is normally secreted to instigate cell death in damaged or dysfunctional tissues, allowing surrounding healthy cells to divide and fill in voids. Thus, increasing the sensitivity to Cachexin in dysfunctional cells may help accelerate such a process and is not always deleterious.

Acceleration of cell death was also seen in tissues that were stressed with radiation and serum-starvation associated with exposure to compositions of the invention.

The infusion of a certain balanced mixture of redox signaling molecules using compositions of the invention into viable HMVEC-L and JB6 cell cultures has been seen to elicit distinct bioactivity. No indications of toxicity or the expression of inflammatory cytokines were observed and yet there was increased antioxidant and protective enzyme expression (as evidenced by increased nuclear NRF2) and greatly increased efficacy for the two master antioxidants, GPx and SOD. This behavior suggests that infusion with compositions of the invention might tend to induce and enhance oxidative defense mechanisms without inducing toxic or inflammatory responses in such cells. Such action is unprecedented or extremely rare. Normally, low-level toxicity induces slight oxidative stress and inflammatory response which in turn induces oxidative defense and cell repair mechanisms. It would be of interest to determine concentration dependency of this effect with ultra-low-concentration infusions of compositions of the invention.

The induction of cell death in cultures of dysfunctional, stressed or damaged cells by infusion of compositions of the invention should also be explored. Natural healing processes involve a repair or replace mechanism by which marginally damaged cells are repaired, when possible, or undergo apoptosis, programmed death, if they cannot be repaired and then are replaced through mitosis of healthy neighboring cells. It is fairly evident that infusion of composition of the invention, of itself, is not causing direct stress to exposed cells, however, it might tend to increase the efficiency of certain cytokine "death domain" messengers (Cachexin) that are designed to induce cell death in dysfunctional or damaged cells. The nuclear translocation of NRF2 can be considered part of the phase II oxidative defense response which includes expression of antioxidants, DNA repair molecules and other known repair mechanisms.

Apoptosis is part of the replace mechanism when cells have undergone unrepairable damage and must be removed and replaced. Both antioxidant defense and apoptotic mechanisms are central to normal tissue repair and regeneration. Redox signaling is involved in several of the pathways, such as p53 gene expression, that can determine whether a cell undergoes apoptosis or not. Chronic oxidative stress tends to favor cell death. Certainly the presence of Cachexin and other death domain messengers favor cell death. The observation that infusion with compositions of the invention enhances Cachexin reception might indicate that infusion with compositions of the invention also might serve to enhance reception of messengers in the signaling process that determines whether defense, repair or replace mechanisms are activated.

Example 15

Delivery of Beverage to Exercising Mice

The effect of ASEA ingestion on treadmill endurance capacity, fuel substrate utilization, tissue inflammation, and tissue oxidative stress in mice was studied. If ASEA causes increased fatty acid mobilization then endurance capacity can be improved in mice taking ASEA (compared to placebo). Sparing of muscle glycogen can be seen when taking ASEA. Mice were given the equivalent of about half the human ASEA dose.

Figure 39:
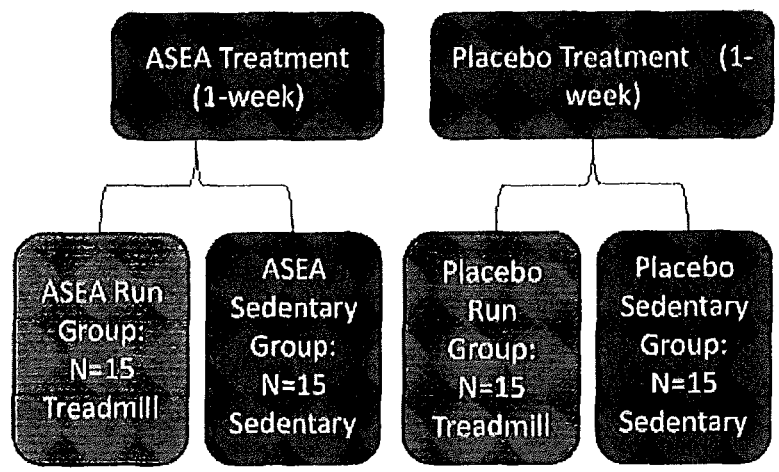
FIG. 39 is a flow chart showing an overview of a mouse study protocol to determine increase in athletic ability.

Six-month old male specific pathogen-free C57BL/6 laboratory mice (n=60) were purchased from Jackson Laboratory. Mice were randomly assigned to each of four treatment groups (n=15 each). A total overview of the mouse preparation and study is illustrated in FIG. 39.

This particular strain and model of mouse has been used in previous studies involving both exercise and nutritional intervention studies. Thus, the use of this strain allowed comparison to data from other studies. Mice can be a suitable substitute for humans for this type of study because mice are genetically similar to humans and thus data obtained in this study will be translatable to human intervention studies.

All animal procedures took place in the Center for Laboratory Animal Sciences (CLAS) at the North Carolina Research Campus and protocols were reviewed and approved by the Institutional Animal Care and Use Committee (IACUC).

ASEA or placebo (same ingredients as ASEA beverage without the proprietary signaling molecules) was administered to the mice via gavage once per day for 1-week. The average body mass of all the mice at the start of the study and the volume of ASEA used for the gavaging were determined, but the volume did not exceed 0.3 mL per mouse. Guidelines for gavage are as the follows: "the volume should not exceed 1-2% of body weight (=0.2-0.4 ml for a 20 g Mouse)". Thus, a volume of 0.3 mL for a 6 month old 30 g mouse is well below this volume suggestion.

The dosage of 0.3 mL for each mouse is equivalent to 48% of the recommended human dose according to body surface area conversion published in FASEB J. 22, 659-661 (2007).

The beverage was not palatable and the mice did not drink it willingly. Gavage was an acceptable alternative to ensure the mice did not become dehydrated simply because they would not drink the study beverage. The gavaging was performed by the animal husbandry staff at CLAS.

Based on a similar study the effect size was calculated to be 1.647. Using p=0.0125 for significance during a priori power analysis. Using G-Power the following calculation was made and a least significant number of animals is assumed to 12/group. We propose 15 animals per group (with estimated power of 0.95) to account for any loss of power if any animals do not make it through the protocol. Analysis: A Priori: Compute Required Sample Size

| Input | Tail(s) | Two |
|---|---|---|
| | Effect size d | 1.6470588 |
| | α err prob | 0.0125 |
| | Power (1-β err prob) | 0.95 |
| | Allocation ratio N2/N1 | 1 |
| Output | Noncentrality parameter δ | 4.5106563 |
| | Critical t | 2.6694793 |
| | Df | 28 |
| | Sample size | 15 |
| | Actual power | 0.9604227 |

Following the 1-week (7 days) treatment period mice were euthanized and tissues harvested for further analysis of outcome measures. The four groups of mice were phased into the 1-week protocol each day. For example, if Group 1 started the protocol on a given day, Group 2 would begin the protocol on the following day, Group 3 would be begin the following day, and Group 4 the day after that. Mice from Group 1 would then be euthanized following the final treadmill test (7th day of treatment), Group 2, Group 3, and Group 4 each on subsequent days. Thus, total time for the mouse protocol was 11 days. There was overlap of orientation treadmill days, with maximal treadmill testing and euthanasia days. As stated, prior to euthanasia, mice from Group 1 and Group 3 underwent a maximal endurance capacity test to exhaustion on the treadmill using the protocol summarized in the following Table.

| Time (min) | Speed (m/min) | Notes |
|---|---|---|
| 1 | 0 | Adjustment to treadmill |
| 5 | 10 | "warm up" period |
| 2 | 12 | |
| 2 | 14 | |
| 2 | 16 | |
| 2 | 18 | |
| 2 | 20 | |
| 2 | 22 | Speeds between 20-24 m/min correspond to roughly 80% $VO_{2max}$ for mice |
| 2 to end | 24 | Mice stay at this speed until they reach exhaustion (e.g., sit on shock grid for 5 full seconds) |

During the three day period preceding the maximal endurance test, mice were oriented (trained) to the treadmill for 15 min/day. Speeds for the training days were about 10 m/min, 15 m/min, and 18 m/min respectively. Then, on the final day of treatment mice underwent a maximal endurance capacity test on the treadmill (preceding Table).

Mice from Group 2 and Group 4 were not submitted to an endurance capacity test and were euthanized at the end of 1-week treatment. Tissues harvested from these mice were collected to assess the chronic effects of the test beverage in absence of an exercise intervention. All blood/plasma and tissues were snap-frozen in liquid nitrogen and stored at −80° C. until assayed.

For the treadmill orientation and endurance protocols, mice were run on a multi-lane rodent treadmill (Columbus Instruments, Columbus Ohio) equipped with a shock grid at the back. Once each mouse was placed in a treadmill lane, a 1 minute resting period was initiated. At this point, the mouse was able to adjust to the inside of the treadmill chamber. Following the 1 minute rest period, the treadmill belt was started at a speed of about 10 m/min, and the protocol described in the above Table was followed.

Some form of motivation was needed to make the mice run on the treadmill, particularly in the orientation sessions. A variety of forms of motivation can be used. The three most common techniques are, use of shock grid, use of air puffs, and manually tapping a mouse's tail. Use of air puffs have the potential to be ineffective and possibly confounding to data analysis. Given the standard rodent treadmill that is used in this type of testing that encloses the treadmill, manually tapping the tail was not ideal. Thus, shock grids were the best method of motivation for exercise on the treadmill.

The shock grid was positioned at the back of the treadmill. The shock grid delivered pulsed shock at an average current of 1.0 milliamperes at 150 volts (the shock grid was adjustable within a range of 0-3.4 mA). The shock grid was regularly checked with an ampmeter to ensure proper functioning. The shock levels used were 22 times less than that accepted in the literature. Also, the amperage of the system was 167-500 times less than lethal levels for mice, and the total power of the system was 60 times less than lethal levels for mice. No new data or guidelines existed to suggest that the use of a shock grid with our proposed settings was anything but appropriate.

Mice were allowed to run until they were no longer able to keep up with the belt and the hind limbs stayed on the shock grid for more than about 5 seconds. When the mouse was no longer running (as assessed by sitting on the shock grid with all 4 paws off of the belt for more than 5 seconds), the mouse was removed from the shock grid immediately and placed back into the home cage. The mice were then monitored for recovery for a period of at least 20 minutes following the orientation bouts.

The maximal endurance test occurred only once per mouse, and mice were euthanized following the test.

The signs of exhaustion used included a mouse sitting on the shock grid for more than 5 seconds, rapid breathing, and/or increased heart rate. It has been our experience that mice that are not fatigued do not show these signs and will continue to run within 5 seconds of stopping. These procedures follow national recommendations (American Physiological Society's, Resource Book for the Design of Animal Exercise Protocols, 2006) based on research in the area. If at any point during the test a mouse got its foot caught between the shock grid and the treadmill the test was immediately terminated. If the mouse was injured and needed treatment, proper procedures were followed and vivarium staff was notified. If the mouse was deemed not injured, it was allowed to recover and placed back in its home cage and re-tested the following day. Once the mouse completed the protocol the mouse was placed back into its home cage. Generally, mice are usually back up and jumping around the cage within 30 seconds of re-exposure to the home cage following an endurance test. However, mice were still monitored several times during the 20-60 minutes following the procedure and notes were taken of any abnormalities such as apathy or decreased food consumption.

Figure 40:
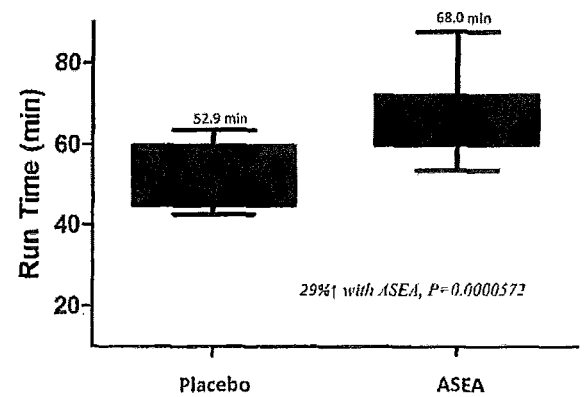
FIG. 40 is a bar graph showing the running endurance time to exhaustion of mice after one week on placebo and one week on ASEA (a composition disclosed herein).

Based on the results from the mouse study, mice which were administered the ASEA increased a run time by almost 30%. In particular, the mice that were taking the placebo ran for about 52 minutes whereas the mice that were administered ASEA ran for about 68 minutes. The results are illustrated in FIGS. 37-45. FIG. 40 illustrates that mice who were administered ASEA had an increased run time to exhaustion. As such, ASEA can be used to increase time to exhaustion in athletes when exercising.

Figure 41:
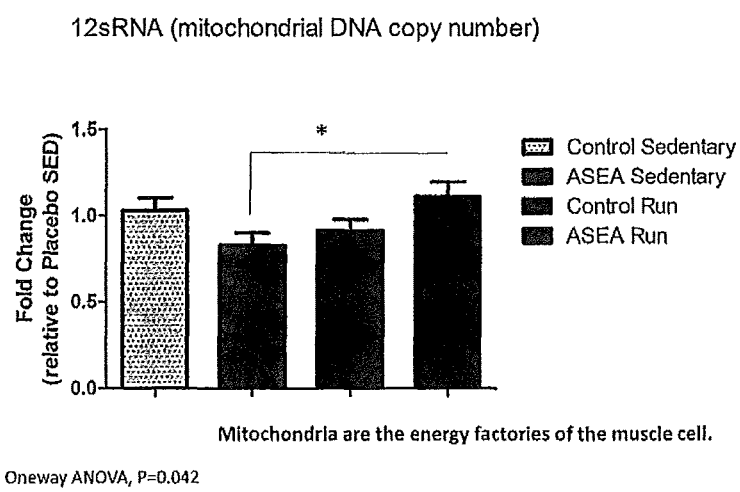
FIG. 41 is a bar graph of the fold change difference between ASEA sedentary (non-running) and ASEA (a composition disclosed herein) running groups as compared to a control group.

FIG. 41 illustrates the fold change relate to ASEA of different mouse groups; P=0.042. This measurement tracks 12sRNA (mitochondrial DNA copy number). One week ASEA consumption in sedentary mice did not increase muscle mitochondria density. An interaction between one long endurance exercise bout to exhaustion was observed with ASEA vs. ASEA sedentary (P<0.05). Fold change increased when ASEA was delivered along with exercise, but fell when exercise was not present. This supports that ASEA helped decrease the level of oxidative stress in the muscle.

Figure 44:
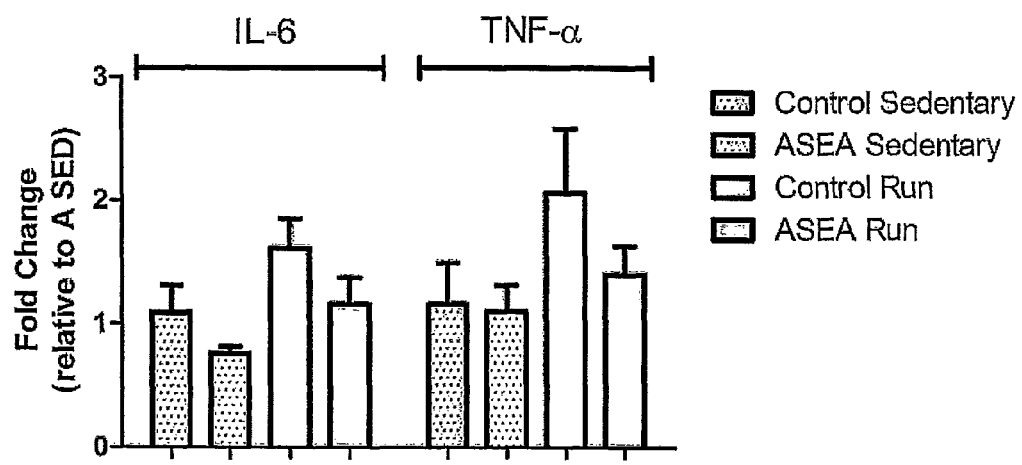
FIG. 44 is a bar graph of the differences in liver SOD between ASEA (a composition disclosed herein) sedentary (non-running) and ASEA running groups as compared to a control group.
Figure 45:
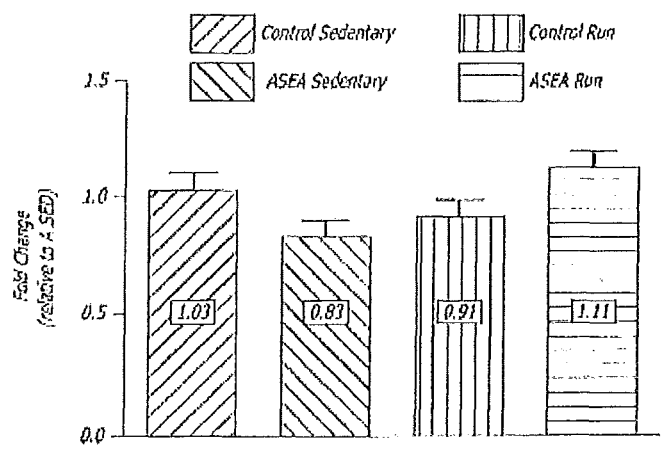
FIG. 45 is a bar graph of the fold change between ASEA (a composition disclosed herein) sedentary (non-running) and ASEA running groups as compared to a control group.

FIG. 44 illustrates that SOD produced in the liver decreases in mice when administered ASEA and subjected to exercise. U is the amount of enzyme needed to inhibit 50% dismutation of the superoxide radical. An acute bout of exercise activates CuZnSOD activity, but most studies reported no change in its mRNA and enzyme protein levels, suggesting that the increased activity was due to increased $O_2$— concentration. This result can indicate that ASEA linked to exercise can reduce oxidative stress.

Figure 42:
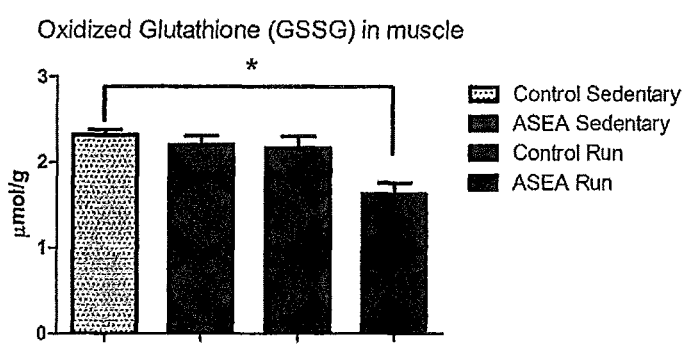
FIG. 42 is a bar graph of the differences in oxidized glutathione (GSSG) in muscle cells between ASEA (a composition disclosed herein) sedentary (non-running) and ASEA running groups as compared to a control group

FIG. 42 illustrates that oxidized glutathione decreases in mice when administered ASEA and subjected to exercise. This result can indicate that ASEA linked to exercise can reduce oxidative stress.

Figure 43:
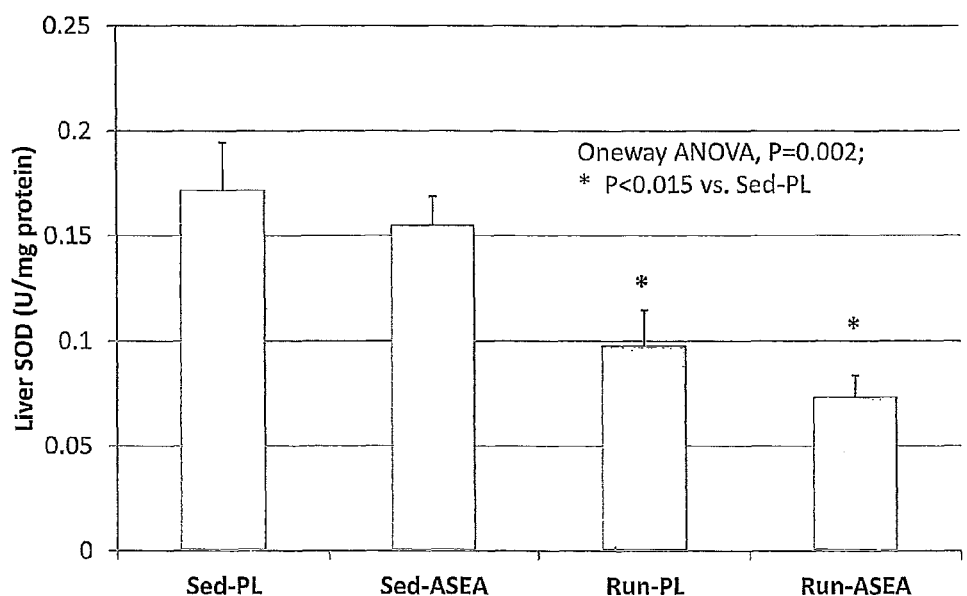
FIG. 43 is a bar graph of the fold change in IL-6 and TNF-α between ASEA (a composition disclosed herein) sedentary (non-running) and ASEA running groups as compared to a control group.

FIG. 43 illustrates that exercise increased mRNA (gene expression) for IL-6 and TNF-α alpha, indicating the typical pro-inflammatory response. ASEA tended to reduce gene expression for these inflammatory cytokines.

Figure 37:
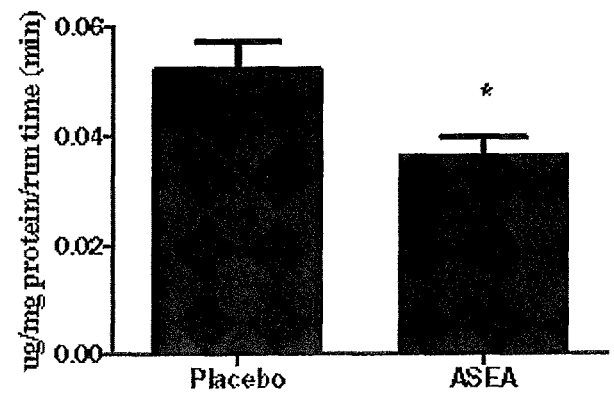
FIG. 37 illustrates the Rate of muscle glycogen depletion in exercised mice.

FIG. 37 illustrates the difference in the rate of muscle glycogen depletion between the study and control groups. The estimated rate of muscle glycogen depletion in the ASEA Run group is significantly different than Placebo Run group (p=0.017).

Figure 38:
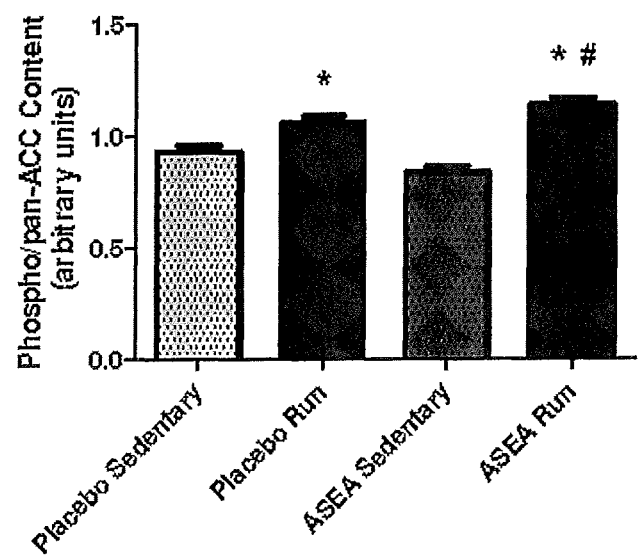
FIG. 38 illustrates the difference in the phosphorylated ACC content between the study and the control groups.

FIG. 38 illustrates the difference in the phosphorylated ACC content between the study and the control groups. The measurements were done by Western Blot analysis in muscle tissue. The asterisk '*' makes reference to significant difference from the sedentary group with the same treatment (p=0.02) and the pound sign '#' shows that the ASEA Run group is significantly different from the Placebo Run group (p=0.045).

Example 16

The efficacy of ingesting ASEA on disease risk factor changes in overweight/obese women was evaluated during a 12-week randomized trial. The disease risk factors included arterial stiffness, inflammation, cholesterol, blood pressure, oxidative stress and capacity, fasting serum glucose and metabolic hormones. 106 subjects were evaluated and these subjects were scrutinized by the following inclusion criteria: healthy, non-smoking female between the ages of 18 and 75 years; overweight (25 or more pounds above recommended levels); non-diseased; not on NSAID medications; not pregnant; not currently on a weight reducing plan or using weight-loss medications; and agree to follow all study procedures and to be randomized to either ASEA or placebo groups.

The following table summarizes the subject baseline characteristics wherein BMI is body mass index, SBP is systolic blood pressure, Chol is cholesterol, CRP is C-reactive protein, A1C is the average glucose over the study period and AIX is the augmentation index:

| | Subject Characteristics | | | | |
|---|---|---|---|---|---|
| | ASEA (N = 53) | | PLACEBO (N = 53) | | |
| | Mean | SD | Mean | SD | P-Value |
| Age (yr) | 50.6 | 12.2 | 49.5 | 12.1 | 0.644 |
| BMI | 34.2 | 6.7 | 33.5 | 5.4 | 0.568 |
| SBP (mm Hg) | 126.0 | 16.8 | 123.0 | 15.7 | 0.414 |
| Chol (mg/dL) | 205.0 | 36.2 | 195.0 | 36.7 | 0.199 |
| CRP (mg/dL) | 6.3 | 5.9 | 6.7 | 8.2 | 0.773 |
| Glucose (mg/dL) | 98.0 | 21.0 | 95.4 | 18.4 | 0.389 |
| Insulin (μIU/mL) | 16.8 | 12.1 | 14.8 | 8.8 | 0.339 |
| A1C (%) | 5.6 | 0.5 | 5.5 | 0.6 | 0.562 |
| AIX (%) | 30.3 | 7.5 | 28.8 | 8.4 | 0.710 |

Figure 46:
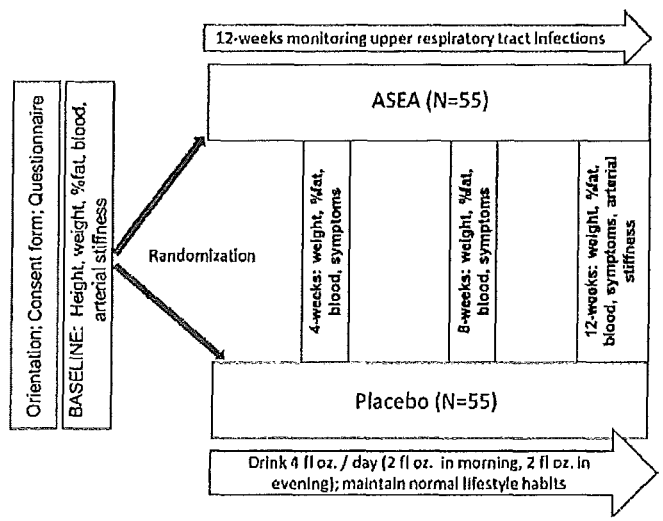
FIG. 46 is a flow chart showing an overview of the protocol for disease risk factor for overweight women study.

The overall study design is shown in FIG. 46 and begins with an orientation, consent forms and questionnaires. After baseline measurements were taken of height, weight, % fat, blood chemistries and arterial stiffness, 55 subjects were randomized into either the study group (ASEA group) or the control group (Placebo group). The placebo was a saline beverage having the same concentration of salt as the ASEA. The subjects ingested a total of 4 fl. oz. of either ASEA or placebo each day of the 12 week study. The 4 fl. oz. was taken as 2 fl. oz. twice a day with one dose in the morning and the other dose in the evening. All subjects were monitored every 4 weeks for different factors such as weight, % fat, blood chemistries, any side effect and arterial stiffness.

Figure 47:
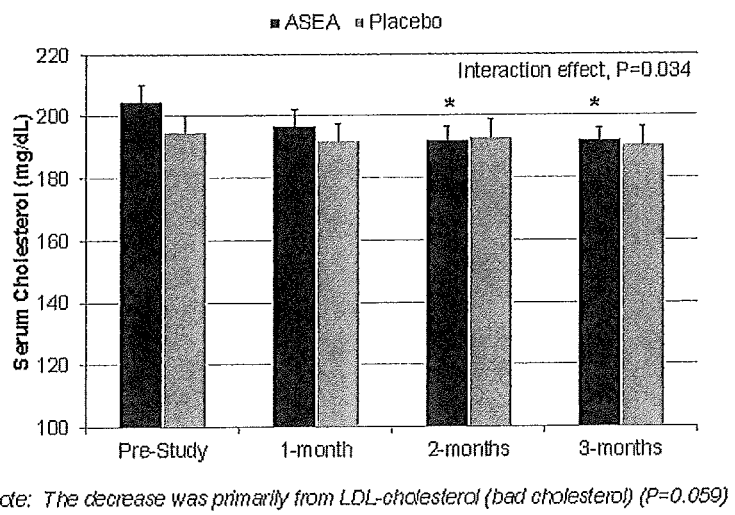
FIG. 47 is a bar graph of the serum cholesterol levels of study subjects as compared to a control group over a 3 month period.
Figure 48:
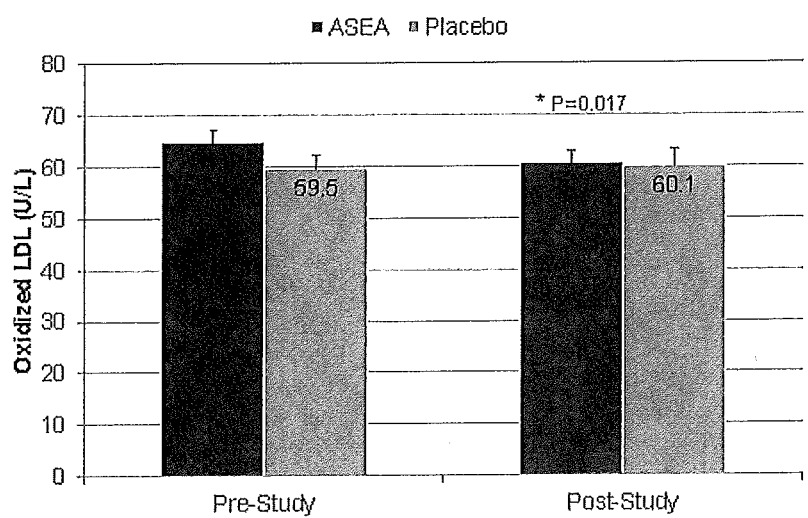
FIG. 48 is a bar graph of the oxidized LDL levels of study subjects as compared to a control group over a 3 month period.
Figure 49:
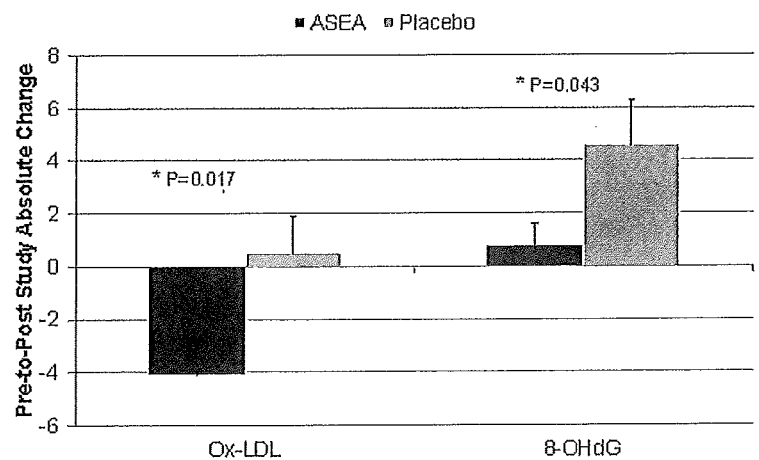
FIG. 49 is a bar graph representing group changes in oxidized LDL and 8-OHdG.
Figure 50:
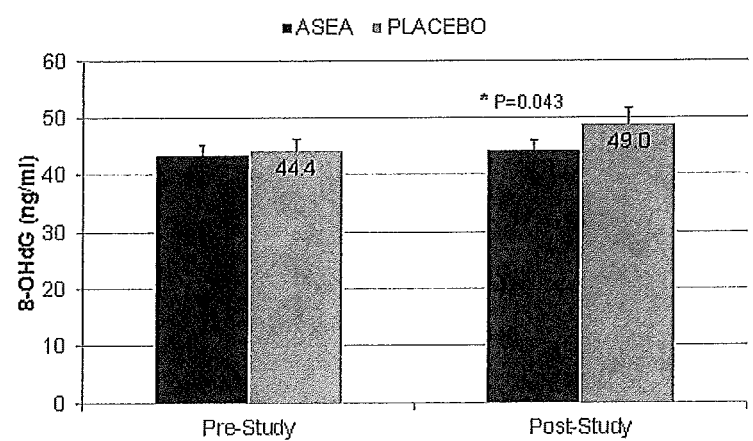
FIG. 50 is a bar graph of the 8-hydroxydeoxyguanosine (8-OHdG) levels of study subjects as compared to a control group over a 3 month period.

After the 12 week study protocol, subjects taking ASEA had a significantly lower LDL-cholesterol value as well as a significantly lower oxidized LDL. FIG. 47 reveals the decrease in LDL-cholesterol (p=0.059) and FIG. 48 shows that the subjects in the ASEA group had significantly lower levels of oxidized LDL. A summary graph representing group changes in oxidized LDL and 8-OHdG is shown in FIG. 49. Additionally, at the end of the study, the placebo group had higher levels of 8-hydroxydeoxyguanosine (8-OHdG) as shown in FIG. 50. 8-OHdG is an oxidized nucleoside of DNA and is a biomarker of generalized, cellular oxidative stress and a risk factor for cancer, atherosclerosis and diabetes. Finally, no adverse symptoms or negative effects on liver, kidney and metabolic function were associated with the study group.

Example 17

Methods and Procedures

Figure 51:
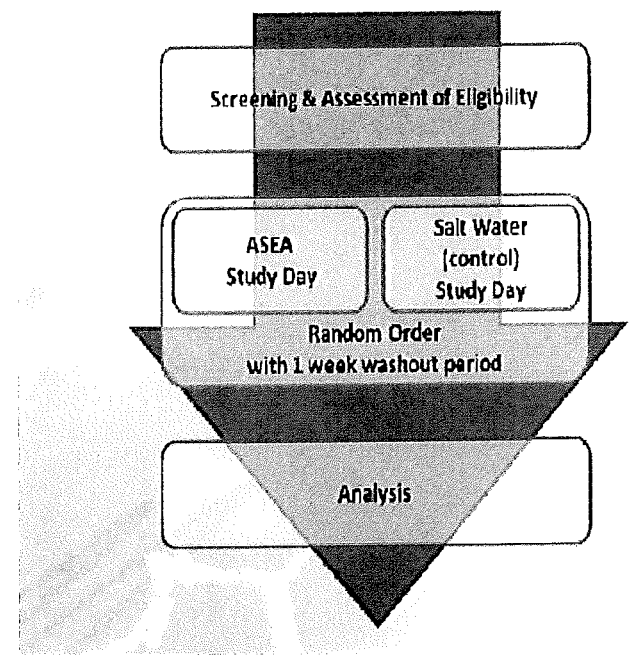
FIG. 51 is an overview of the study design for measuring energy expenditure in a 24 hour period in subjects administered a composition of the present invention.

Study Design: This was a randomized, double-blind, cross-over trial of a composition made according to Example 1 (for this Example 17 such composition is called "Composition A or Composition (A)") versus a salt water control (Composition A & B, respectively) in overweight post-menopausal women. The study consisted of two 24-hour study periods spent in the indirect room calorimeter at the University of North Carolina Chapel Hill Nutrition Research Institute (UNC NRI), each one week apart. The basic study design is shown in FIG. 51. Primary outcome measures were differences in 24-hour energy expenditure (EE) and substrate utilization (RQ) following Composition (A) compared with salt water control (B). Secondary outcome measures were changes in fasted versus postprandial (90 minutes after breakfast) gut peptides GLP-1, PYY, and ghrelin, as well as norepinephrine, epinephrine, dopamine and non-esterified fatty acids (NEFA).

Following recruitment and eligibility assessment, subjects were randomly assigned to first complete either the Composition (A) or the salt water control (B) study day. After a one week wash-out, subjects crossed over and completed the alternative treatment. A method of randomly permuted blocks was generated using web-based randomization software (www.randomization.com) resulting in seven subjects receiving Composition A their first week, and eight subjects receiving the salt water control their first week. Subjects consumed two 4-oz portions of water (Composition A or B); once in the morning before breakfast at 9:05 am and another at 10:15 pm just before bed time at 10:30 pm. During both study days, subjects were fed in energy balance.

Experimental subjects: This study was conducted according to guidelines laid down in the Declaration of Helsinki and all procedures were approved by the Institutional Review Board (IRB) of The University of North Carolina, Chapel Hill. Written informed consent was obtained from all 23 subjects. Using data generated previously in a metabolic chamber (NRI Whole-Room calorimeter), a sample size calculation with 24 80% power revealed that 15 subjects would be needed to detect a 50 kcal difference in EE. To account for attrition, 23 post-menopausal women were recruited via mass advertisement throughout the local area. Post-menopausal women were chosen due to the prevalence of overweight and obesity in this group, and their hormonal status which reduces variability in EE. Inclusion criteria were: age between 50-65 years; body mass index (BMI) between 25 & 35 kg/m2; exercise <150 minutes/week; no history of drug or alcohol abuse; not taking herbal supplements or medications that could influence EE; and willingness to follow all study protocols, including consuming all provided foods. Post-menopausal status was ascertained by self-report. Subjects were excluded if they did not meet the inclusion criteria, or had a thyroid hormone profile that was clearly above or below the normal range (normal reference ranges: T3, 90-178 ng/dL; T4, 6.1-12.2 mcg/dL; and thyroid stimulating hormone (TSH), 0.3-3 3.0 ulU/L).

Eligibility was determined in the outpatient clinical suite at the UNC NRI. Body composition (fat mass and fat free mass (FFM)) was determined via dual energy x-ray absorptiometry (DXA) (GE Lunar 7 iDXA; Milwaukee, Wis.) and body mass index (BMI; kg/m2) was calculated. Resting Metabolic Rate (RMR) was estimated using a FFM-based equation [418+(20.3 FFM)]7. This estimated RMR was used to calculate total dietary energy intake while in the metabolic chamber: RMR×physical activity level (PAL) of 1.3, and then adjusted using measured data (details provided below). A small blood sample was obtained at this time and T3, T4, and TSH levels were assessed.

Indirect calorimetry: The metabolic chamber at the Nutrition Research Institute in Kannapolis, N.C. was modeled on chambers at the National Institute of Diabetes and Digestive and Kidney Diseases, Bethesda, Md.8, and is an open-circuit, pull-type, whole room indirect calorimeter built with 'walk-in cooler' panels. This chamber and data reproducibility has been previously described. Briefly, an air conditioning system mixes chamber air, maintaining a pre-set temperature of approximately 24° C. and a relative humidity of <70%. Fresh, conditioned air is passively drawn from an adjacent buffer zone. Mixed, expired air is drawn through a centralized sampling apparatus designed with evenly spaced sectors to ensure equal sampling throughout the chamber, via a fan. Flow was set to a constant rate of 60 L/min. Air samples were cooled to 1° C., dried, drawn by a diaphragm pump and filtered. The CO2 and O2 analysers are differential, with full scale readings set for 0%-1%. O2 consumption, CO2 production, EE and RQ were recorded each minute. EE was calculated using an abbreviated Weir's formula (VO2×3.941)+(VCO2×1.106), where VO2 is the volume of oxygen consumed in L/minute and VCO2 is the volume of carbon dioxide released in L/minute. RQ was calculated as VCO2/VO2. Area under the curve (AUC) was calculated using RQ data for the four hours following breakfast, lunch and dinner as well as sleeping hours between midnight and 6:00 am. A passive infrared motion sensor measured the percentage spontaneous physical activity each minute. To calculate resting Confidential metabolic rate (RMR), EE was plotted against the activity motion sensor output (each averaged over 30 minutes), and the y-intercept of the linear regression taken as EE in the inactive state, (kJ/minute). RMR was multiplied by 1440 minutes to extrapolate to 24 hours. Twenty four hour sleeping metabolic rate (SMR) was determined as the lowest mean EE (kJ/minute) measured over 3 consecutive hours between midnight and 6:30 am and multiplied by 1440 minutes. Diet induced thermogenesis (DIT) was calculated by subtraction of SMR from RMR. Activity induced EE (AEE) was calculated as the difference between 24 hour EE and RMR.

Metabolic chamber study day protocol: At 7:30 am subjects reported to the metabolic chamber following an overnight fast (no food from 10 pm). Subjects were instructed to avoid exercise, caffeine and alcohol for two days prior to entering the chamber. Subjects were instructed on expectations of their stay and were weighed in scrubs without shoes. At 8:00 am subjects were sealed in the chamber. Except for a 2-minute interval each hour during which subjects were requested to stand, stretch and take their temperature, subjects were asked to remain seated or reclined, but awake throughout the day. Subjects were asked to perform necessary daily activities during these 2-minute intervals. To minimize variation in activity, subjects were requested to complete an hourly activity log on visit, and requested to mimic this log closely on visit 2. Breakfast (9:15 am), lunch (1:15 pm), and dinner (7:00 pm), were served through an air-lock passage. Meals were completed within 20 minutes of serving. Four ounces of Composition A or B (salt water control) were consumed at 9:05 am just before breakfast and at 10:15 pm just prior to bed time. At 9:00 am and 11:00 am subjects were asked to place one of their arms through an iris port for blood sampling. At 10:30 pm, subjects were asked to lie down for sleep. Subjects were woken at 6:30 am and were allowed to move about the chamber to gather their belongings. At 7:15 am subjects exited the chamber and were weighed.

Design of Metabolic Diets: Eucaloric diets were designed to provide approximately 35% fat, 49% carbohydrates and 16% protein, reflecting current recommendations for this population group. Menus were designed using the nutrient calculation and food management software ProNutra (Vio-Care, Princeton, N.J.), and consisted of bagel, peanut butter, apple juice, whole-wheat bread, turkey, cheese, mayonnaise, buttery spread (10% kcal as fat), potato chips, lasagna, carrots, broccoli, rolls and peach muffins. The same foods were served at both chamber visits. A baseline menu for each subject was prepared based on calculated RMR×1.3, reflecting the sedentary nature of the study day. To ensure energy balance conditions, the baseline menu of the first visit was modified according to measured EE data at 3 hours (includes breakfast) and 7 hours (includes breakfast and lunch). Subsequent meals were adjusted accordingly with 100 kcal peach muffins containing the same proportion of fat, carbohydrate and protein as the meals. Subjects were fed an identical amount of the same meal at their second visit.

Biochemical Analyses: Ghrelin, GLP-1 and PYY were analysed using a magnetic bead-based multiplex assays (Millipore, Billerica, Mass.) on a Luminex FlexMap3D™ (Luminex, Austin, Tex.). Samples were run in duplicate, and intra-assay CVs. were <10%. Catecholamines (epinephrine, norepinephrine) were measured by HPLC with electrochemical detection (HPLC-EC). TSH was measured using a two-site immune-enzymatic (sandwich) assay while T3 and T4 were measured using a competitive binding immune-enzymatic assay. All thyroid hormone tests were run on a Beckman Unicel DXI 800 Immunoassay System (Beckman Coulter, Brea, Calif.). Glucose was measured by electro-chemiluminescence assay on a DXC 800 (Beckman Coulter, Brea, Calif.). Insulin was measured by electrochemiluminescence assay on a Roche E170 (Roche Diagnostics, Indianapolis, Ind.). Plasma fatty acids were measured by ELISA (ZenBio, Inc., Research Triangle Park, N.C.).

Statistical Analysis: Data were analysed using SAS (Cary, N.C.), and are expressed as mean±SD unless otherwise stated. To guard against any carryover effect from visit 1 to visit 2, a repeated measures regression with an unstructured correlation matrix within subject was run with treatment (A and B) and visit (1 and 2) in the model along with an interaction term. If the interaction term proved non-significant then it was removed and the model was re-run. $p<0.05$ was considered statistically significant. For the NEFA, Ghrelin, GLP1, PYY, norepinephrine, epinephrine and dopamine data, to compare the change from 9:00 am to 11:00 am for A or B, or to compare the difference at 11:00 am between A and B, a paired t-test was used. For 9:00 am to 11:00 am comparisons, there were n=13 samples; for A to B comparisons at 11:00 am, there were n=14 samples. $p<0.05$ was considered statistically significant.

Results

Description of the study cohort: 23 women were recruited for the study. Following screening and eligibility assessment, 17 subjects were deemed eligible. Sixteen subjects completed all study days. One subject was excluded due to poor compliance with the study protocol, leaving a total of subjects taken forward to the final analysis. Clinical characteristics of the study population are detailed in the following Table.

|  | Mean | SD |
| --- | --- | --- |
| Age (years) | 56.7 | 3.8 |
| BMI (kg/m$^2$) | 28.9 | 2.2 |
| FFM (%)[1] | 44.0 | 4.4 |
| Body Fat (%)[1] | 45.6 | 4.9 |
| T3 (ng/dL)[2] | 118 | 15.6 |
| T4 (meg/dL)[3] | 8.6 | 1.6 |
| TSH (uIU/mL)[4] | 1.3 | 0.7 |

BMI, body mass index
FFM (%), % fat free mass
[1] as determined by dual x-ray absorptiometry
[2] Normal laboratory reference range: 90-178 ng/dL
[3] Normal laboratory reference range: 6.1-12.2 meg/dL
[4] Normal laboratory reference range: 0.3-3.00 µIU/mL
TSH, thyroid stimulating hormone Subjects were non-Hispanic white or African-American women. The average age was 56.7 years (range 51.3-62.9 years), with an average body mass index (BMI) of 28.9 kg/m2 (25.1-31.4 kg/m2). No significant differences in age, body weight, BMI or % body fat were identified between groups previously randomized to complete the Composition (A) study day first versus those who completed the salt water control (B) study day first (data not shown).

Composition A affected components of the 24-hour EE and substrate utilization compared with salt water control in overweight, post-menopausal women. Subjects were weight stable between study days A and B (79.3±9.3 versus 79.5±9.6 (kg); p=0.18), respectively. RMR was significantly increased in subjects receiving Composition A vs. control water (6.16±0.69 versus 5.84±0.82 MJ/day; p=0.02), respectively as can be seen in the following table (RMR, resting metabolic rate; SMR, sleeping metabolic rate; DIT, diet induced thermogenesis; AEE, activity induced thermogenesis; B, breakfast; L, lunch; D, dinner; AUC, area under the curve; RQ, respiratory quotient (liters CO2/liters O2). *paired t-test; <0.05 considered significant):

|  | Composition (A) (n = 15) Mean ± SD | Salt Water Control (B) (n = 15) Mean ± SD | p-value * |
| --- | --- | --- | --- |
| 24-hour EE (MJ/day) | 7.07 + 0.64 | 6.91 + 0.76 | 0.2 |
| RMR (MJ/day) | 6.16 + 0.69 | 5.84 + 0.82 | 0.02 |
| SMR (MJ/day) | 5.30 + 0.722 | 5.05 + 0.813 | 0.11 |
| DIT (MJ/day) | 0.882 + 0.270 | 0.833 + 0.299 | 0.44 |
| AEE (MJ/day) | 0.908 + 0.307 | 1.07 + 0.432 | 0.02 |
| 24 h % Activity | 10126 + 4507 | 10579 + 4768 | 0.36 |

| | Composition (A) (n = 15) Mean ± SD | Salt Water Control (B) (n = 15) Mean ± SD | p-value * |
|---|---|---|---|
| Temperature (F.) | 98.0 + 0.53 | 97.9 + 0.36 | 0.72 |
| 24 h RQ | 0.872 + 0.016 | 0.881 + 0.017 | 0.01 |
| Post B AUG RQ | 211 + 4.97 | 214 + 6.34 | 0.07 |
| Post L AUG RQ | 208 + 4.62 | 209 + 5.19 | 0.6 |
| Post D AUG RQ | 206 + 5.11 | 209 + 4.10 | 0.03 |
| Midnight to 6am RQ | 205 + 4.64 | 208 + 4.40 | 0.008 |

Figure 52:
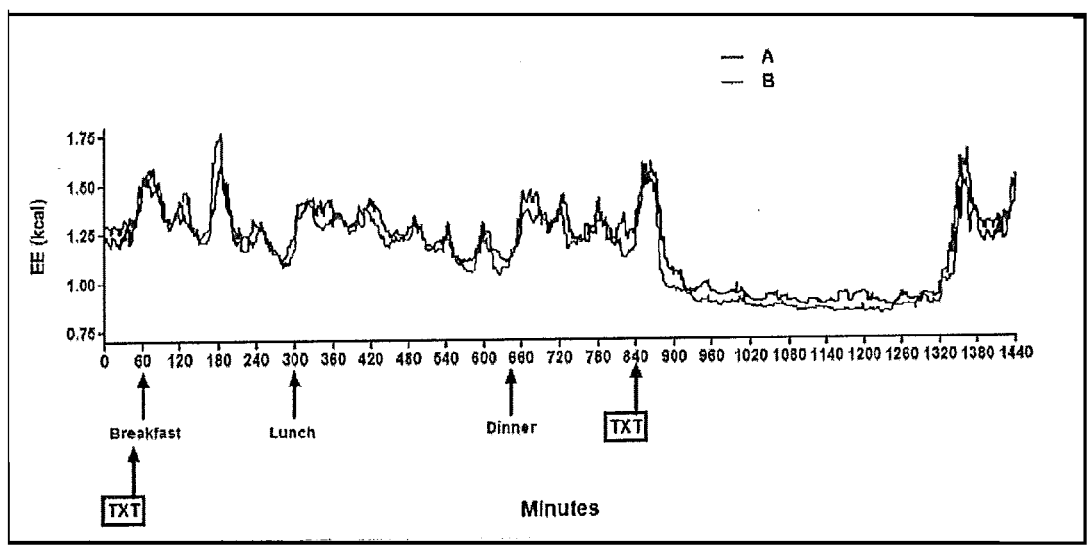
FIG. 52 is a graphed comparison of the effect of ASEA (A) (a composition disclosed herein) and Salt Water Control (B) on 'minute by minute' Energy Expenditure over 24 hours.
Figure 53:
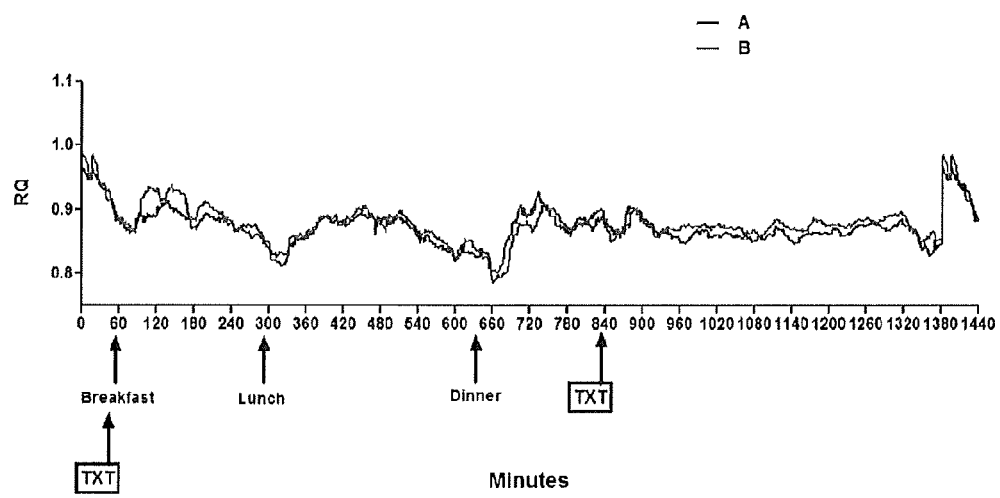
FIG. 53 is a graphed comparison of the effect of ASEA (A) (a composition disclosed herein) and Salt Water Control (B) on RQ (respiratory quotient, liters CO2/liters O2) over 24 hours.

The above table shows that administration of Composition A to a number of subject increases the caloric burn of those subjects. The above table shows that RMR increased by about 76 calories/day. The calculation shows a difference of 0.32 MJ/day (6.16 MJ/day-5.84 MJ/day) which is equal to 76.431 calories/day. The results are graphed in FIG. 52 which shows the amount of energy expenditure (EE) in kJ over a 1440 min (24 hr) period of subjects in A (Composition A) and B (Control) groups. SMR (5.30±0.722 versus 5.05±0.813 (MJ/day); p=0.11) and diet-induced thermogenesis (DIT) (0.882±0.270 versus 0.833±0.299 (MJ/day); p=0.44) trended higher on the Composition A study day vs. salt water control, respectively, but the differences were not statistically significant. Interestingly, activity induced EE (AEE) was significantly reduced in subjects receiving Composition A vs. control water (0.908±0.307 versus 1.07±0.432 (MJ/day); p=0.02), respectively. Twenty-four hour RQ was slightly but significantly decreased on Composition A versus control study days (0.872±0.016 versus 0.881±0.017; p=0.01) respectively, indicating a shift toward increased fat oxidation. Areas under the curve (AUC) for RQ were significantly decreased on Composition A versus control during the 4 hours post-dinner period (206±5.11 versus 209±4.10; p=0.03) and from midnight to 6:00 am (205±4.64 versus 208±4.40; p=0.008), but not during the 4 hours post-breakfast (211±4.97 versus 214±6.34; p=0.07) or post-lunch (208±4.62 versus 209±5.19; p=0.6) periods (FIG. 53). Body temperature was not significantly different between the A and B study days (98.0±0.53 versus 97.9±2 0.36; p=0.7), respectively.

Example 18

A study was conducted to evaluate the impact of ingestion of a composition made according to Example 1 (which for this Example 18 will be referred to as ASEA in some instances and as a composition of the current invention in others), during a two week period, on run time to exhaustion and metabolic phenotype. Global biochemical profiles were determined in 24 human plasma samples, comparing across the treatment groups shown below. All participants completed the placebo and ASEA arms of the cross-over study, were randomly assigned a cross-over order, and completed a two week wash out period between the different supplementation arms of the study. The treatment groups can be categorized as shown in the table below:

| Treatment Group | Pre-Supplementation (PreS) | Post-Supplementation/ Pre-exercise (PreE) | Post-exercise (PostE) |
|---|---|---|---|
| Placebo | N = 24 | N = 24 | N = 24 |
| ASEA | N = 24 | N = 24 | N = 24 |

Figure 54:
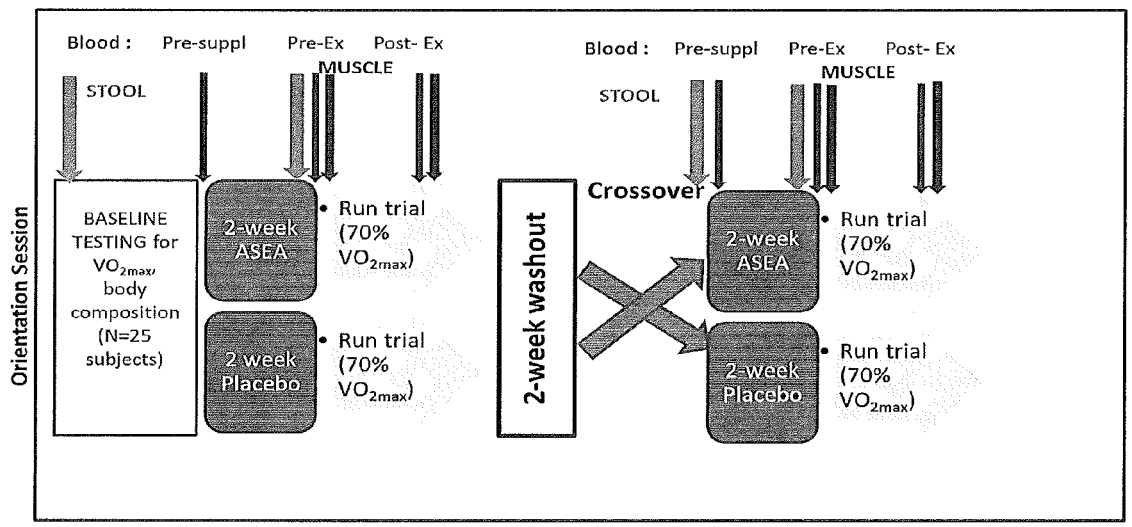
FIG. 54 is an overview of the study design for an evaluation of the impact of the ingestion of a composition made according to the invention, during a two week period, on run time to exhaustion and metabolic phenotype.

A double-blind cross-over study on twenty four (N=24) male long-distance runners was performed. Blood, fecal and muscle biopsy samples were collected before and after a run to exhaustion (at constant power, 70% VO2max) on two randomized groups (N=12 for each), the placebo group drank saline water and the study group drank ASEA, 4 oz. in the morning per day for two weeks preceding the run trial. There was a two week washout period before the cross-over, groups were swapped and the procedure was repeated as indicated in FIG. 54.

Physiological Explanation of Metabolomic Measurements: In humans, ingested nutrients are digested into simple blood-borne sugars (monosaccharides, mostly glucose and fructose) along with a balance of amino acids (about 20 kinds of them) and a huge variety of fatty acids (strings of carbon atoms with hydrogen atoms attached). Fatty acids are classified by the length of the carbon strings, the distribution of hydrogen (H) and carbon double-bonds along the carbon strings and the way they are bundled together by the carboxyl (COOH) attachment points on one end of the carbon strings; this affords many different combinations. Unbundled fatty acids are called free fatty acids. In cells, the metabolism involves admitting glucose/fructose into the cells where they are converted into pyruvate, then inside the mitochondria pyruvate is converted into Acetyl CoA fuel, the universal fuel of the mitochondria. Also, free fatty acids are admitted into the mitochondria and undergo beta-oxidation to be converted into 85% (during rest) of the Acetyl CoA fuel. The Acetyl CoA fuels the mitochondrial aerobic (oxygen utilizing) respiration cycles including the citric acid (TCA) cycle that squeezes out the high energy electrons into NADH electron carriers that are used to provide electrons to the electron transport chain to produce ATP fuel for the cells. All of these metabolic pathways involve hundreds of chemical intermediates. Metabolomics is a methodology to measure the blood-borne sugars, amino acids and metabolic intermediates that provide a "fingerprint" of what is happening inside the complex metabolic process. Special attention is placed on the various fatty acids, they can serve in various roles inside and outside cells. The lipid membranes that enclose cells, nuclei, mitochondria and other structures are composed of bundles of fatty acids stuck together in a bi-layer sheet called a bilipid membrane. Side chains attached to fatty acids and the position of carbon double bonds along the carbon strings in fatty acids also carry messages and provide structural support. Interpreting where these fatty acids are synthesized also gives us clues as to what might be happening with them in the body.

Some 382 blood-borne biochemical markers were analyzed in the three blood draws surrounding each of the run trials. The Pre-supplementation sample (PreS) was taken before each two-week supplementation period, the Pre-Exercise sample (PreE) was taken 30 minutes before each run trial and the Post-Exercise sample (PostE) was taken just minutes after each run trial. Following log transformation and imputation with minimum observed values for each compound, ANOVA contrasts were used to identify biochemical markers that differed significantly between experimental groups.

Figure 55:
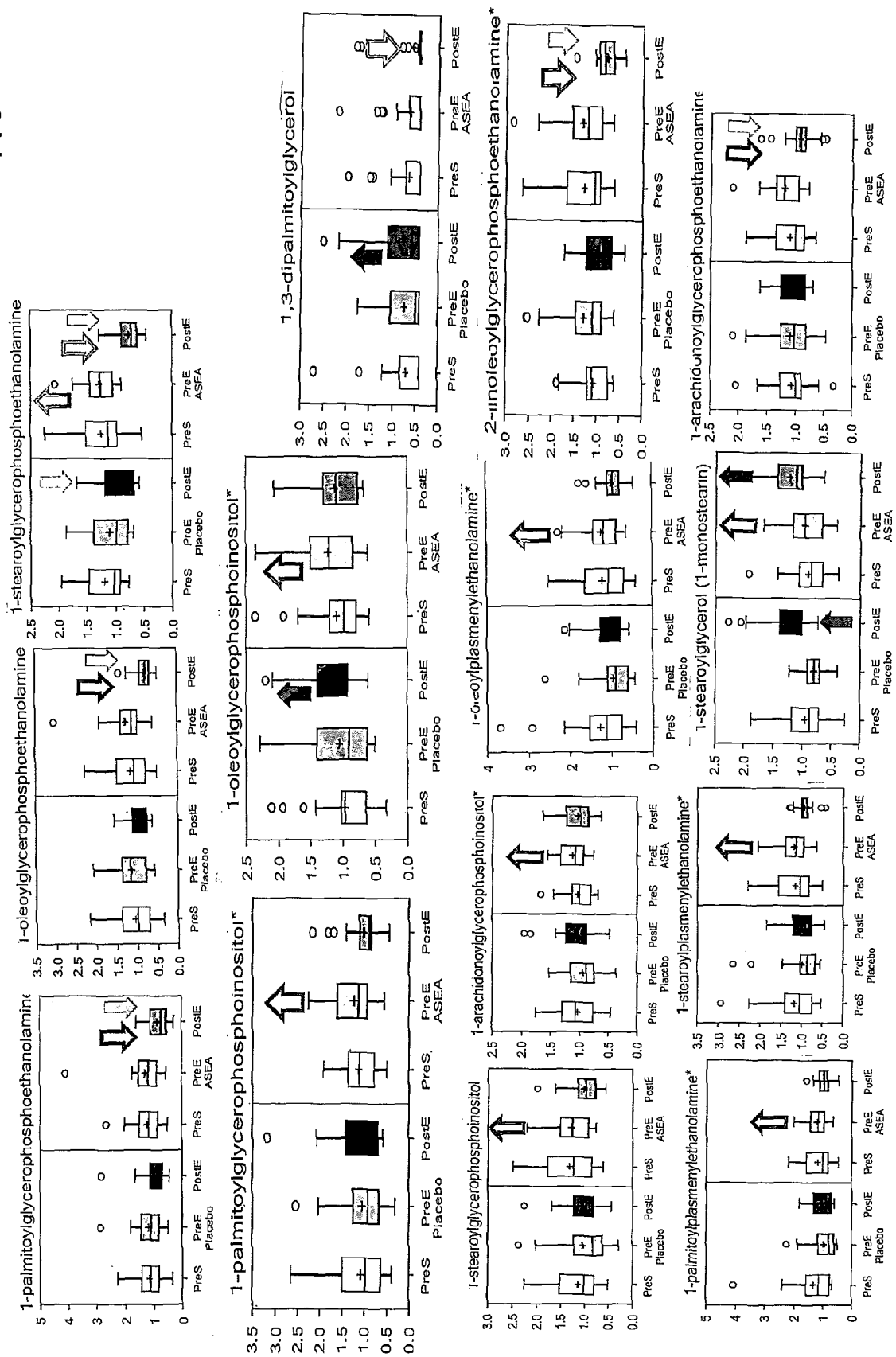
FIG. 55 displays the measurements of certain fatty acids that were mobilized as a result of the study design for an evaluation of the impact of the ingestion of a composition made according to the invention, during a two week period, on run time to exhaustion and metabolic phenotype.

FIG. 55 displays the measurements of certain fatty acids that were mobilized. In particular, the table below explains the graphs in FIG. 55 and shows that post exercise decreases in concentrations certain structural lipids in the LysoPE classification were observed. These types of lipids are often utilized in the break-down of certain bilipid structures that constitute cell walls and platelets. These are generally needed during cell reconstruction efforts. Additionally, pre-exercise increases in certain lipids classified under LysoPI were observed. These lipids also have a role in the reconstruction of lipid membranes, especially liposomes employed by immune cells (macrophages).

| Fatty Acid | PreS Placebo | PreE Placebo | PostE Placebo | PreS ASEA | PreE ASEA | PostE ASEA |
|---|---|---|---|---|---|---|
| A | | | | | Approaching significance (higher or lower) compared to placebo group at the same time point | Significantly lower compared to respective PreS baseline |
| B | | | | | Approaching significance (higher or lower) compared to placebo group at the same time point | Significantly lower compared to respective PreS baseline |
| C | | | Significantly lower compared to respective PreS baseline | Significantly higher compared to placebo group at the same time point | Significantly lower compared to placebo group at the same time point | Significantly lower compared to respective PreS baseline |
| D | | | | | Approaching significance (higher or lower) compared to placebo group at the same time point | Significantly lower compared to respective PreS baseline |
| E | | | | | Approaching significance (higher or lower) compared to placebo group at the same time point | |
| F | | Approaching significance (higher or lower) compared to PreS baseline | | | | Significantly lower compared to placebo group at the same time point |
| G | | Significantly higher compared to respective PreS baseline | | | Significantly higher compared to placebo group at same time point | |
| H | | | | | Approaching significance (higher or lower) compared to placebo group at the same time point | Significantly lower compared to respective PreS baseline |
| I | | Significantly higher compared to respective PreS baseline | | | | Significantly higher compared to respective PreS baseline |
| J | | Significantly higher compared to respective PreS baseline | | | Approaching significance (higher or lower) compared to placebo group at the same time point | Significantly higher compared to respective PreS baseline |
| K | | Significantly higher compared to respective PreS baseline | | | Significantly higher compared to respective PreS baseline | Significantly higher compared to respective PreS baseline |

For the above table, the following definitions A through K, inclusive, apply to the first column entitled Fatty Acid and relate to the same named fatty acid in the corresponding FIG. 55:

"A" means 1-palmitoylglycerophosphoethanolamine
"B" means 1-oleoylglycerophosphoethanolamine
"C" means 1-stearoylglycerophosphoethanolamine
"D" means 1-arachidonoylglycerophosphoethanolamine
"E" means 1-palmitoylglycerophosphoinositol
"F" means 1,3-dipalmitoylglycerol
"G" means 1-oleoylglycerophosphoinositol
"H" means 2-linoleoylglycerophosphoethanolamine
"I" means 1-palmitoylglycerol(1-monopalmitin)
"J" means 1-stearoylglycerol(1-monostearin)
"K" means glycerol Significantly higher means $p \leq 0.05$, significantly lower means $p \leq 0.05$, and approaching significance means $0.05 < p < 0.1$.

Figure 56:
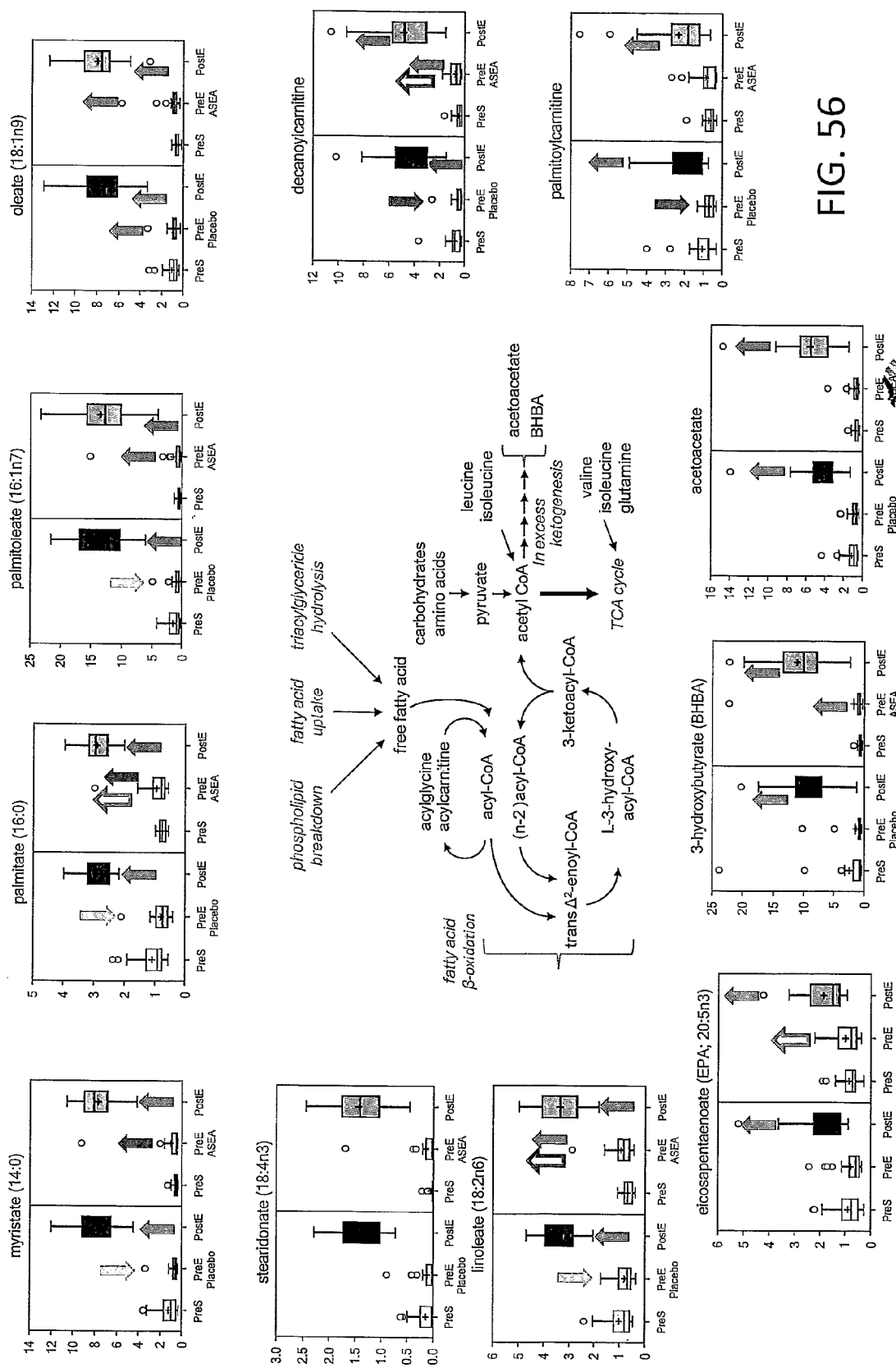
FIG. 56 shows graphs detailing the fatty acid oxidation increase by exercise and perhaps by a product of this invention and shown as a result of the study design for an evaluation of the impact of the ingestion of a composition made according to the invention, during a two week period, on run time to exhaustion and metabolic phenotype.

FIG. 56 shows graphs detailing the fatty acid oxidation increase by exercise and perhaps by ASEA. The table below details the information in FIG. 56. Significantly higher means $p \leq 0.05$, significantly lower means $p \leq 0.05$, and approaching significance means $0.05 < p < 0.1$.

| Component | PreS Placebo | PreE Placebo | PostE Placebo | PreS ASEA | PreE ASEA | PostE ASEA |
|---|---|---|---|---|---|---|
| Myristate | | Significantly lower compared to respective PreS baseline | Significantly higher compared to respective PreS baseline | | Approaching significance (higher or lower) relative to PreS baseline | Significantly higher compared to respective PreS baseline |
| Palmitate | | Significantly lower compared to respective PreS baseline | Significantly higher compared to respective PreS baseline | | Significantly higher compared to placebo group at the same time point AND approaching significance (higher or lower) compared to PreS baseline | Significantly higher compared to respective PreS baseline |
| Palmitoleate | | Significantly lower compared to respective PreS baseline | Significantly higher compared to respective PreS baseline | | Significantly higher compared to respective PreS baseline | Significantly higher compared to respective PreS baseline |
| Oleate | | Significantly higher compared to respective PreS baseline | Significantly higher compared to respective PreS baseline | | Significantly higher compared to respective PreS baseline | Significantly higher compared to respective PreS baseline |
| Decanoylcarnitine | | Approaching significance (higher or lower) relative to PreS baseline | Significantly higher compared to respective PreS baseline | | Significantly higher compared to respective PreS baseline AND approaching significance (higher or lower) compared to placebo at same time point | Significantly higher compared to respective PreS baseline |
| Palmitoylcarnitine | | Approaching significance (higher or lower) relative to PreS baseline | Significantly higher compared to respective PreS baseline | | | Significantly higher compared to respective PreS baseline |
| Acetoacetate | | | Significantly higher compared to respective PreS baseline | | | Significantly higher compared to respective PreS baseline |
| 3-hydroxybutyrate (BHBA) | | | Significantly higher compared to respective PreS baseline | | Significantly higher compared to respective PreS baseline | Significantly higher compared to respective PreS baseline |
| Eicosapentaenoate | | | Significantly higher compared to respective PreS baseline | | Significantly higher compared to placebo group at the same time point | Significantly higher compared to respective PreS baseline |

-continued

| Component | PreS Placebo | PreE Placebo | PostE Placebo | PreS ASEA | PreE ASEA | PostE ASEA |
|---|---|---|---|---|---|---|
| Linoleate | | Significantly lower compared to respective PreS baseline | Significantly higher compared to respective PreS baseline | | Significantly higher compared to respective PreS baseline AND approaching significance (higher or lower) compared to placebo at same time point | Significantly higher compared to respective PreS baseline |
| Stearidonate | | | | | | |

Figure 57:
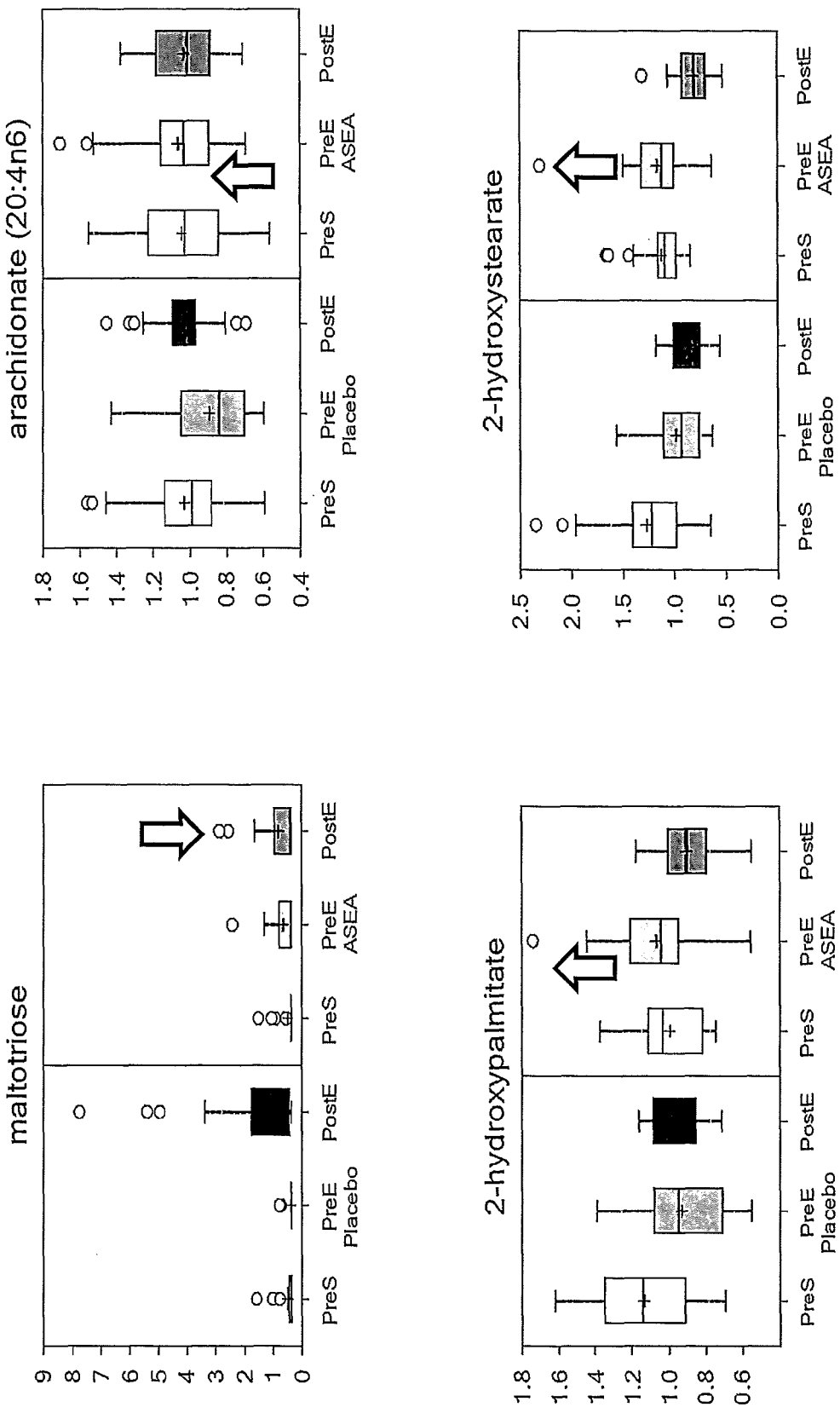
FIG. 57 is a graphed analysis of certain physiological changes after administration of a product of this invention and shown as a result of the study design for an evaluation of the impact of the ingestion of a composition made according to the invention, during a two week period, on run time to exhaustion and metabolic phenotype.

FIG. 57 is a graphed analysis of certain changes wherein p<0.05, q<0.25 for changes after the administration of a product of this invention. In particular, there was a significantly lower measurement for maltotriose PostE in subjects administered ASEA as compared to the placebo group at the same time point, a significantly higher measurement for arachidonate PreE in subjects administered ASEA compared to the placebo group at the same time point, a significantly higher measurement for 2-hydroxysearate PreE in subjects administered ASEA compared to the placebo group at the same time point, and a significantly higher measurement for 2-hydroxypalmitate PreE in subjects administered ASEA compared to the placebo group at the same time point.

Figure 58:
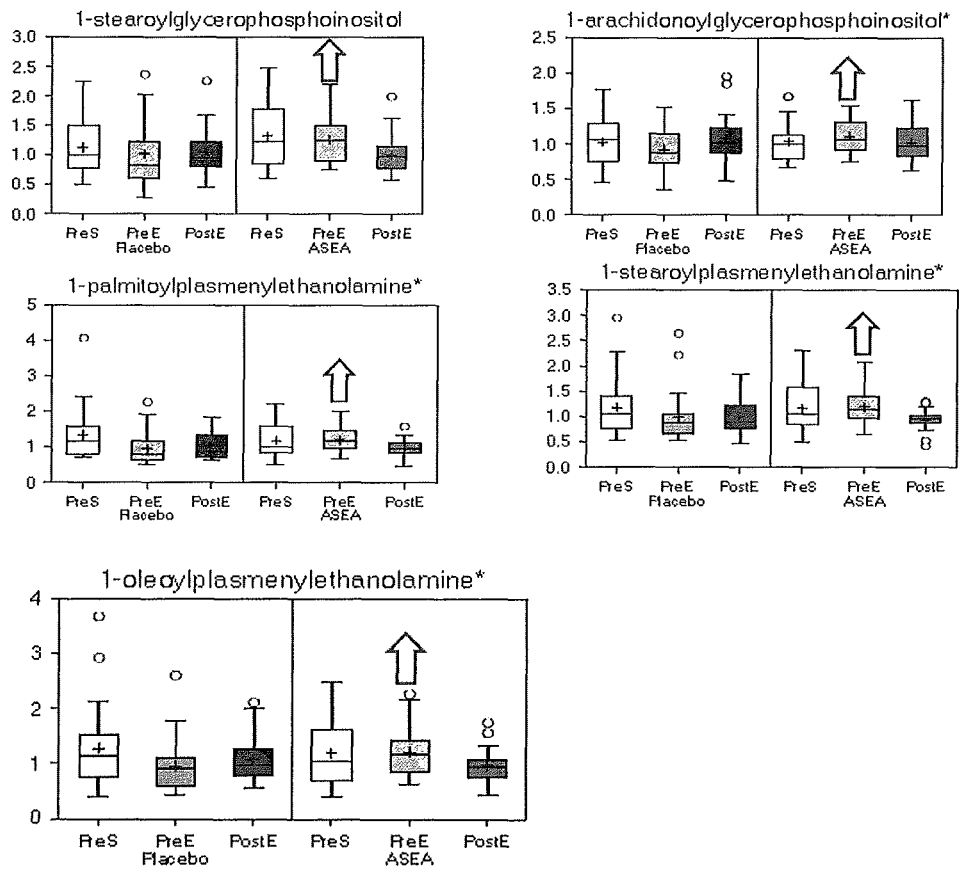
FIG. 58 is a graphed analysis of certain physiological changes after administration of a product of this invention and shown as a result of the study design for an evaluation of the impact of the ingestion of a composition made according to the invention, during a two week period, on run time to exhaustion and metabolic phenotype.

FIG. 58 is a graphed analysis of certain changes wherein p<0.05, q<0.25 for changes after the administration of a product of this invention. In particular, there was a significantly higher measurement for 1-stearoylglycerophosphoinositol PreE in subjects administered ASEA compared to the placebo group at the same time point, a significantly higher measurement for 1-arachidonoylglycerophosphoinositol PreE in subjects administered ASEA compared to the placebo group at the same time point, a significantly higher measurement for 1-palmitoylplasmenylethanolamine PreE in subjects administered ASEA compared to the placebo group at the same time point, a significantly higher measurement for 1-stearoylplasmenylethanolamine PreE in subjects administered ASEA compared to the placebo group at the same time point, and a significantly higher measurement for 1-oleoylplasmenylethanolamine PreE in subjects administered ASEA compared to the placebo group at the same time point.

Physiological responses differentially modified by ASEA supplementation were focused in a few areas. ASEA and placebo groups displayed modest differences in lipid metabolism. Many lysophosphatidylethanolamine lipids—including 1-palmitoylglycerophosphoethanolamine, 1-stearoylglycerophosphoethanolamine, and 2-linoleoylglycerophosphoethanolamine (2-LGPE)—showed a differential reduction in the ASEA group, relative to the placebo group, following exercise and, with the exception of 2-LGPE, shared the same stereochemical configuration with the acyl chain attached at the sn-1 position. Similarly sn-1 lysophosphatidylinositols (lysoPIs), such as 1-palmitoylglycerophosphoinositol, and sn-1 lysophosphatidylethanolamine plasmalogen, such as 1-palmitoylplasmenylethanolamine, all showed differential elevations in the ASEA group relative to the placebo group before exercise but not after.

Phospholipase A2 (PLA2) catalyzes the release of fatty acids, such as arachidonic acid, phosphatidylethanolamine and lysophosphatidylinositols from the glycerol or diacyl glycerol backbones. PLA2 recognizes the sn-2 acyl bond of phospholipids and releases arachidonic acid (AA) and lysophopholipids. What is shown from this Example is that ASEA causes a post exercise decrease in certain phospholipids and a pre-exercise increase in phosphoinositols.

Arachidonic acid (AA) and its derivatives, collectively known as the eicosanoids, are key mediators of a wide variety of physiological states. AA is liberated from its phospholipid storage sites (PE and PI) by the action of one or various phospholipase A2 (PLA2) enzymes. AA is the precursor of a large family of bioactive compounds called the eicosanoids. Sensitive to redox processes, they exert complex control over many bodily systems, mainly in inflammation or immunity, and as messengers in the central nervous system. The networks of controls that depend upon eicosanoids are among the most complex in the human body.

Eicosanoids are derived from either omega-3 (ω-3) or omega-6 (ω-6) fatty acids. The ω-6 eicosanoids are generally pro-inflammatory; ω-3s are much less so. The amounts and balance of these fats in a person's diet will affect the body's eicosanoid-controlled functions, with effects on cardiovascular disease, triglycerides, blood pressure, and arthritis. Anti-inflammatory drugs such as aspirin and other NSAIDs act by downregulating eicosanoid synthesis. There are at multiple subfamilies of eicosanoids, including the prostaglandins, prostacyclins, the thromboxanes, lipoxins and the leukotrienes.

Phospholipase A2 (PLA2) isoforms that target phosphatidylethanolamine (PE) and PE plasmalogen have been characterized from a variety of sources including heart, brain, neutrophils, and endothelial cells. The action of a PLA2 family member is strongly implicated in the pre-exercise increases of lysoPls and lysoPE plasmalogens, given their sn-1 configuration, since the products of these enzymes are free fatty acids and sn-1 lysolipids. The diacylglycerol sn-1,3-dipalmitoyglycercol was increased in the placebo group but decreased in the ASEA group following exercise. Interestingly, a lysosomal PLA2 has been identified that has a second activity to transacylate monoacylglycerols to produce 1,3-diacylglycerols. This lysosomal PLA2 is highly expressed in macrophages and appears to play an important role in macrophage function and innate immune cell activation. Based on the data here, it is proposed that ASEA may modulate the activity of this PLA2 enzyme or the function of macrophages that produce it.

A limited number of highly significant changes associated with ASEA clustered into a few metabolic areas. In addition to changes in maltotriose, lysoPls, lysoPE plasmalogens already discussed, ASEA treatment had a significant impact on pre-exercise levels of arachidonate and 2-hydroxy fatty acids such as 2-hydroxypalmitate. Arachidonate (AA) tends to be enriched at the sn-2 of phosphatidylinositols and the pre-exercise increase of sn-1 lysoPls in the ASEA group, such as 1-oleoylglycerophoshoinositol, could be an indication that AA and lysoPls are co-generated by a PLA2 isoform. 2-Hydroxy fatty acids are conventional lipid components and are important constituents of sphingolipids. The hydroxyl group is believed to add to the hydrogen-bonding capacity of the sphingolipids, helping to stabilize membrane structures and strengthen the interactions with membrane proteins.

Figure 59:
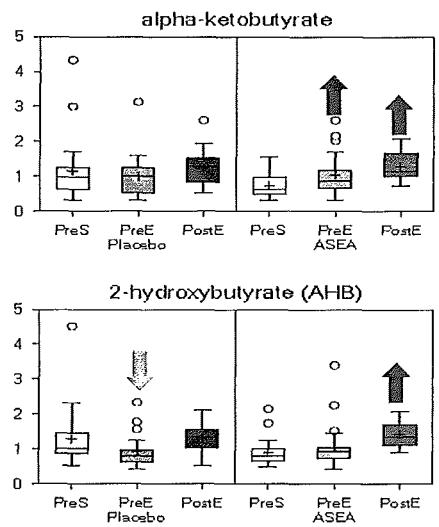
FIG. 59 is a graphed analysis of certain physiological changes after administration of a product of this invention and shown as a result of the study design for an evaluation of the impact of the ingestion of a composition made according to the invention, during a two week period, on run time to exhaustion and metabolic phenotype.

Regarding insulin resistance, a key marker of insulin resistance, 2-hydroxybutyrate (AHB), and its precursor alpha-ketobutyrate were significantly elevated in the ASEA treatment group following exercise but not the placebo group. AHB and alpha-ketobutyrate started from different pre-supplementation baselines, for unknown reasons. Thus, the changes in AHB and alpha-ketobutyrate are pointed out as potential metabolic adaptations that are more sensitive to ASEA. FIG. 59 graphically shows the results of a significant increase in alpha-ketobutyrate PreE and PostE in the subjects which received ASEA. This same figure shows a significant decrease of AHB compared to PreS baseline of PreE in the subjects receiving placebo and a significant increase of AHB in the subjects receiving ASEA as compared to respective PreS baseline measurement.

Figure 60:
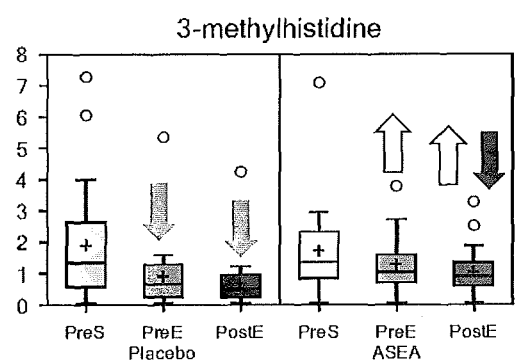
FIG. 60 is a graphical representation of the measurement of 3-methylhistidine after administration of a product of this invention and shown as a result of the study design for an evaluation of the impact of the ingestion of a composition made according to the invention, during a two week period, on run time to exhaustion and metabolic phenotype.

3-Methylhistidine (3-MH) and trans-4-hydroxyproline—markers of myofibrillar protein and collagen breakdown, respectively—decreased following exercise relative to their pre-supplementation baseline for the respective treatment groups. 3-MH was elevated in the ASEA group relative to the placebo group at both the PreE and PostE time points which suggests a greater level of muscle protein turnover following ASEA consumption. However, the decrease of 3-MH in both groups is somewhat surprising given that this marker generally increases following exercise. However, most studies have reported on 3-MH levels in urine so it is possible that the urinary levels of 3-MH were higher in the subjects. The results indicating a significantly lower PreE and PostE measurement of 3-MH in the placebo group, a significantly higher measurement of 3-MH PreE and PostE in the ASEA group, and a lower measurement approaching significance compared to PreS baseline for the 3-MH in the PostE ASEA group are shown in FIG. 60.

Xanthine and hypoxanthine, which are derived from the catabolism of purine nucleotides, were elevated following exercise. Interestingly, both of these biochemicals are substrates for the hydrogen peroxide-generating enzyme xanthine oxidase (XO), which can create a pro-oxidative environment. However, urate, the product of XO catalysis of xanthine is a potent free radical scavenger whose production is often increased to neutralize reactive oxygen species. While not clearly linked to hypoxanthine or xanthine production, two guanine-containing purines, 7-methylguanine and N2,N2-dimethylguanosine, were elevated after exercise were relatively higher in the ASEA group compared to the placebo group following exercise. 7-methylguanine is derived from the breakdown of methylated DNA whereas N2,N2-dimethylguanosine is largely derived from the turnover of tRNAs. These changes suggest that oxidative stress was experienced by both treatment groups following exercise and hinted at a slightly greater level of purine catabolism following ASEA treatment.

Figure 61:
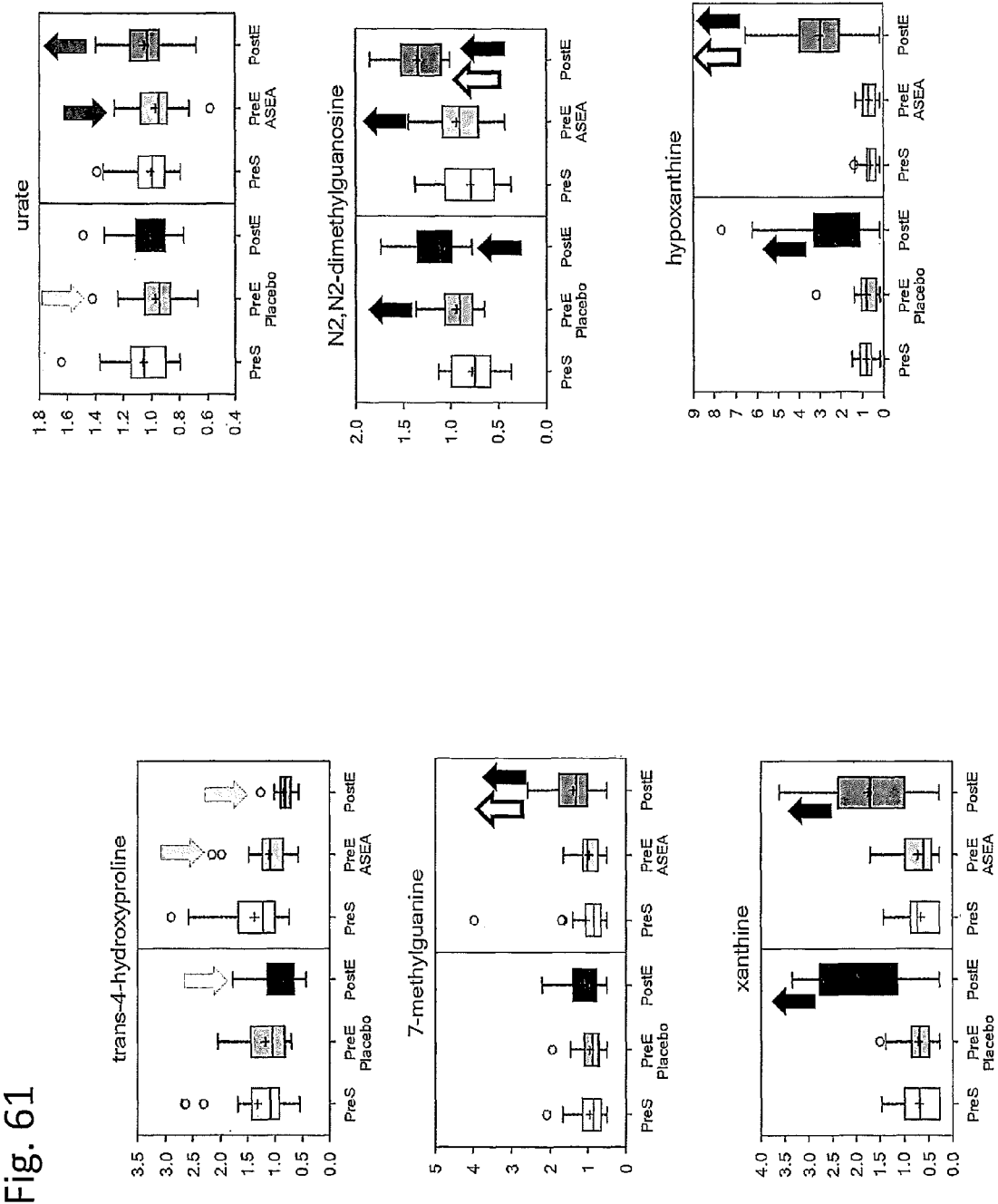
FIG. 61 is a graphical representation of this trend of purines and urate after administration of a product of this invention and shown as a result of the study design for an evaluation of the impact of the ingestion of a composition made according to the invention, during a two week period, on run time to exhaustion and metabolic phenotype.

FIG. 61 is a graphical representation of this trend of purines and urate as noted above and can be summarized in the following table:

| Component | PreS Placebo | PreE Placebo | PostE Placebo | PreS ASEA | PreE ASEA | PostE ASEA |
| --- | --- | --- | --- | --- | --- | --- |
| Trans-4-hydroxyporoline | | | Significantly lower compared to PreS baseline | | Significantly lower compared to PreS baseline | Significantly lower compared to PreS baseline |
| Urate | | Significantly lower compared to PreS baseline | | | Approaching significance (higher or lower) compared to PreS baseline | Approaching significance (higher or lower) compared to PreS baseline |
| 7-methylguanine | | | | | | Approaching significance (higher or lower) compared to placebo at the same time point AND significantly higher compared to PreS Baseline |
| N2,N2-dimethylguanosine | | Significantly higher compared to PreS Baseline | Significantly higher compared to PreS Baseline | | Significantly higher compared to PreS Baseline | Significantly higher compared to PreS Baseline AND significantly |

-continued

| Component | PreS Placebo | PreE Placebo | PostE Placebo | PreS ASEA | PreE ASEA | PostE ASEA |
|---|---|---|---|---|---|---|
| | | | | | | higher compared to placebo group at same time point |
| Xanthine | | | Significantly higher compared to PreS Baseline | | | Significantly higher compared to PreS Baseline |
| hypoxanthine | | | Significantly higher compared to PreS Baseline | | | Significantly higher compared to PreS Baseline AND approaching significance (higher or lower) compared to placebo group at same time point |

Figure 62:
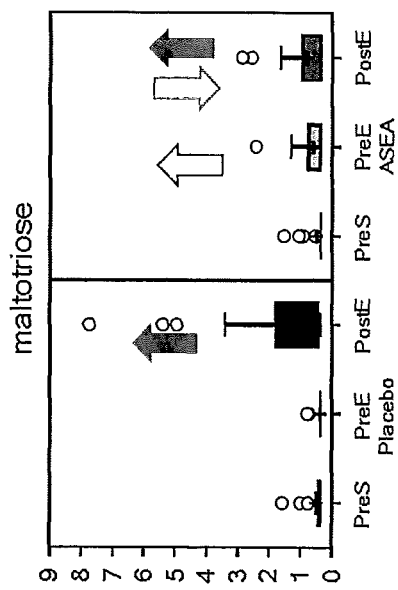
FIG. 62 graphically represents the differences in maltotriose levels after administration of a product of this invention and shown as a result of the study design for an evaluation of the impact of the ingestion of a composition made according to the invention, during a two week period, on run time to exhaustion and metabolic phenotype.

FIG. 62 graphically represents the differences in maltotriose levels between the ASEA and placebo group such that there was a significantly higher level of maltotriose in the placebo group PostE as compared to PreS baseline, a measurement approaching significance in the measurement of maltotriose in the ASEA group PreE as compared to the placebo group at the same time point, a significantly lower measurement of maltotriose in the PostE ASEA group as compared to placebo group at the same time point, and a significantly higher level of maltotriose in the ASEA group PostE as compared to PreS baseline.

The clearest distinctions between the ASEA and placebo groups were suggestions of altered glycogen metabolism, without being bound by theory a potentially increased hydrolysis of phosphatidylinositols and phosphatidylethanolamine plasmalogens by PLA2 before exercise and less hydrolysis of non-plasmalogen phosphatidylethanolamines after exercise.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

It is contemplated that numerical values, as well as other values that are recited herein are modified by the term "about", whether expressly stated or inherently derived by the discussion of the present disclosure. As used herein, the term "about" defines the numerical boundaries of the modified values so as to include, but not be limited to, tolerances and values up to, and including the numerical value so modified. That is, numerical values can include the actual value that is expressly stated, as well as other values that are, or can be, the decimal, fractional, or other multiple of the actual value indicated, and/or described in the disclosure.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

We claim:

1. A method for mobilizing fatty acids in a subject with a composition comprising redox-signaling molecules, the method comprising:
   providing a subject;
   preparing a composition comprising a mixture of reduced species (RS) and reactive oxygen species (ROS) by electrolyzing a circulating saline solution to produce the mixture of reduced species (RS) and reactive oxygen species (ROS) wherein the mixture of reduced species and reactive oxygen species mobilizes the fatty acids in a subject;
   administering the composition to the subject;
   exercising the subject; and
   verifying increased mobilization of fatty acids in the subject by measuring biochemical markers related to mobilization of fatty acids in the subject.

2. The method of claim 1, wherein the biochemical markers comprise one or more of 1-palmitoylglycerophosphoethanolamine, 1-oleoylglycerophosphoethanolamine, 1-stearoylglycerophosphoethanolamine, 1-arachidonoylglycerophosphoethanolamine, 1-palmitoylglycerophosphoinositol, 1,3-dipalmitoylglycerol, 1-oleoylglycerophosphoinositol, 2-linoleoylglycerophosphoethanolamine, 1-palmitoylglycerol (1-monopalmitin), 1-stearoyl glycerol (1-monostearin), glycerol, myristate, palmitate, palmitoleate, oleate, decanoylcarnitine, palmitoylcarnitine, acetoacetate, 3-hydroxybutyrate (BHBA, eicosapentaenoate, linoleate, stearidonate, trans-4-hydroxyporoline, urate, 7-methylguanine, N2,N2-dimethylguanosine, xanthine, and hypoxanthine.

3. The method of claim 1, wherein administering the composition comprises administering four ounces of the composition daily to the subject for at least two weeks prior to exercising the subject.

* * * * *